(12) United States Patent
Filho et al.

(10) Patent No.: US 10,889,624 B2
(45) Date of Patent: Jan. 12, 2021

(54) PROTEINS FROM THE WEBS OF NEPHILENGYS CRUENTATA, A VICULARIA JURUENSIS AND PARAWIXIA BISTRIATA SPIDERS ISOLATED FROM BRAZILIAN BIODIVERSITY

(71) Applicants: Empresa Brasileira de Pesquisa Agropecuaria—EMBRAPA, Brasilia (BR); Fundacao Universidade de Brasilia, Brasilia (BR)

(72) Inventors: Elibio Leopoldo Rech Filho, Brasília (BR); Natalia Cristina Verza Ferreira, Brasília (BR); Giovanni Rodrigues Vianna, Brasília (BR); Felipe Rodrigues da Silva, Brasília (BR); Francisco José Lima Aragão, Brasília (BR); Luiz Alberto Colnago, São Carlos (BR); Alan Carvalho Andrade, Brasília (BR); Daniela Matias de Carvalho Bittencourt, Brasília (BR); Pedro Ismael da Silva Junior, São Carlos (BR); Betúlia de Morais Souto, Brasília (BR); Luisa de Moraes Madeira, Brasília (BR); Paulo César Motta, Brasília (BR)

(73) Assignees: Empresa Brasileira de Pesquisa Agropecuaria-Embrapa, Brasilia (BR); Fundaçao Universidade de Brasilia, Brasilia (BR)

( * ) Notice: Subject to any disclaimer, the term of this patent is extended or adjusted under 35 U.S.C. 154(b) by 0 days.

(21) Appl. No.: 13/749,601

(22) Filed: Jan. 24, 2013

(65) Prior Publication Data
US 2014/0206851 A1 Jul. 24, 2014

Related U.S. Application Data

(63) Continuation of application No. 12/531,664, filed as application No. PCT/BR2008/000072 on Mar. 13, 2008, now abandoned.

(30) Foreign Application Priority Data

Mar. 16, 2007 (BR) ..................................... 0701826

(51) Int. Cl.
*C07K 14/435* (2006.01)
*A61K 38/00* (2006.01)

(52) U.S. Cl.
CPC ........ *C07K 14/43518* (2013.01); *A61K 38/00* (2013.01)

(58) Field of Classification Search
None
See application file for complete search history.

(56) References Cited

U.S. PATENT DOCUMENTS

| 2004/0102608 A1 | 5/2004 | Rathore et al. |
| 2005/0019297 A1 | 1/2005 | Philippe et al. |

FOREIGN PATENT DOCUMENTS

| WO | WO 2003/020916 A2 | 3/2003 |
| WO | WO 2006/008163 A2 | 1/2006 |

OTHER PUBLICATIONS

Bittencourt et al ("Spidroins from the Brazilian spider Nephilengys cruentata (Araneae: Nephilidae)," Comparative Biochemistry and Physiology, Part B 147 (2007) 597-606).*
Basic Local Alignment Search Tool, pp. 1-36, Apr. 13, 2015.*
NCBI report Apr. 13, 2015.*
Arcidiacono S et al.: "Purification and characterization of recombinant spider silk expressed in *Escherichia coli*." Appl Microbiol Biotechnol. Jan. 1998;49(1):31-8. PMID: 9487707 [retrieved on Jun. 20, 2008 (Jun. 20, 2008)].
Lazaris A et al.: "Spider silk fibers spun from soluble recombinant silk produced in mammalian cells."Science. Jan. 18, 2002;295(5554):472-6. PMID: 11799236 [retrieved on Jun. 20, 2008 (Jun. 20, 2008)].
Lewis RV et al. : "Expression and purification of a spider silk protein: a new strategy for producing repetitive proteins." Protein Expr Purif. Jun. 1996; 7(4): PMID: 8776759 [retreived on Jun. 20, 2008 (Jun. 20, 2008)].

(Continued)

*Primary Examiner* — Nancy J Leith
(74) *Attorney, Agent, or Firm* — Arent Fox LLP

(57) ABSTRACT

The Present invention relates to molecules isolated from the nucleic acid that encodes spider web proteins or fragments of these or other derivatives of these. The invention also refers to a chimerical gene and an expression vector containing molecules isolated from the nucleic acid that codes for proteins related to the webs of *Nephilengys, cruentata, Avicularia juruensis* and *Parawixia bistriata* spiders. Another embodiment of the present invention are transformed cells containing a chimerical gene or an expression vector of the present invention. Yet another embodiment of the present invention relates to a method for obtaining genetically modified organisms containing inventive chimerical genes or expression vectors and a method for obtaining recombinant proteins from the silks of *Nephilengys, cruentata, Avicularia juruensis* and *Parawixia bistriata* spiders. Finally, the invention describes products, such as biofilaments and compositions, using the recombinant proteins of the present invention. The discovery of new spider silk proteins, as well as their characterisation and expression in different heterologous systems shall be of great use in numerous areas, such as medicine and industry.

32 Claims, 8 Drawing Sheets
Specification includes a Sequence Listing.

(56) References Cited

OTHER PUBLICATIONS

Scheller J et al.: "Production of spider silk proteins in tobacco and potato." Nat Biotechnol. Jun. 2001;19(6):573-7. PMID: 11385464 [retreived on Jun. 20, 2008 (Jun. 20, 2008)].
Wong Po Foo C and Kaplan DL: "Genetic engineering of fibrous proteins: spider dragline silk and collagen." Adv Drug Deliv Rev. Oct. 18, 2002;54(8): 1131-43. PMID: 12384311 [retrieved on Jun. 20, 2008 (Jun. 20, 2008)].

* cited by examiner

SEQUENCE LISTING

<160> NUMBER OF SEQ ID NOS: 40

<210> SEQ ID NO 1
<211> LENGTH: 3277
<212> TYPE: DNA
<213> ORGANISM: Nephilengys cruentata

<400> SEQUENCE: 1

```
agcgggaggt tcaggtggaa caacagtcat agaagatttg acataacag ttaatggtcc      60 aggaggcccg ataacaatct cagaagagct aacaattggt ggtccaggtg ctggaggttc    120
aggacctggt ggtgctggac caggaggcgc aggacccggt ggtgcaggac caggaggcgc    180
aggacctggt ggtgcaggac caggaggagt aggacctggt ggtgctggag ccctggtgg    240 tgctggagga cctttcggtc caggtggttc cggacccgga ggtgcaggcg cgctggagg    300 accttatgga cctggtggag cttacggacc tggtggacct ggagggcctg gtggtcctgg    360
aggacccggt tctggcggac cttacggacc tggtggtgct acggacctg gtggtgctta    420 cggacctggt ggtgcttatg gtcctggtgg agctggtgga ccaggtggag ctggtggacc    480
atatggaccc ggtggacctt acggaccagg tggtccatac ggacctggtg agctggtgg    540 accaggtggt gctggtggac cttatggacc aggaggtgct ggacctggcg gatacggacc    600
tggaggcgct ggacctggtg gatacggacc tggcggttct ggacctggag cgctggacc    660 tggtggatac ggacctggcg ttctggacc tggtggtgct ggacccggtg gatatggacc    720
tggtggtgct ggacccggtg gatacggacc tggtggtgct ggacctggcg gtgctggacc    780
tggtggtgct ggtcctggtg gatacggacc tggcggttct ggaccaggtg gtcctggatc    840
tggtggccca ggcggagcgg gaggttcagg tggaacaaca gtcatagaag atttggacat    900
aacagttaat ggtccaggag cccgataac aatctcagaa gagctaacag ttggtggtcc    960
aggtgctgga ggttcaggac ctggtggtgc tggaccagga ggcgcaggac ccggtggtgc   1020
aggaccagga ggagtaggac ctggtggtgc tggaggccct ggtggtgctg gaggacctttt   1080 cggtccaggt ggttccggac ccggaggtgc aggcggcgct ggaggacctt atggacctgg   1140
tggagcttac ggacctggtg gacctggagg gcctggtggt cctggaggac ccggttctgg   1200
cggaccttac ggacctggtg gtgcttacgg acctggtggt gcttacggac ctggtggtgc   1260
ttatggacct ggtggagctg gtggaccata tggacccggt ggaccttacg gaccaggtgg   1320
tccatacgga cctggtggag ctggtggacc aggtggtgct ggtggacctt atggaccagg   1380
aggtgctgga cctggcggat acggacctgg aggcgctgga cctggtggat acggacctgg   1440
cggttctgga cctggaggcg ctggacctgg tggatacgga cctggcggtt ctggacctgg   1500
tggtgctgga cccggtggat atggacctgg tggtgctgga cccggtggat acggacctgg   1560
tggtgctgga cctggcggtg ctggacctgg tggtgctggt cctggtggat acggacctgg   1620
cggttctgga ccaggtggtc ctggatctgg tggcccaggc ggagcgggag gttcaggtgg   1680
aacaacagtc atagaagatt tggacataac agttaatggt ccaggaggcc cgataacaat   1740
ctcagaagag ctaacagttg gtggtccagg tgctggaggt tcaggacctg gtggtgctgg   1800
accaggaggc gcaggacccg gtggtgcagg accaggaggc gcaggacctg gtggtgcagg   1860
accaggagga gtaggacctg gtggtgctgg aggccctggt ggtgctggag gacctttcgg   1920
tccaggtggt tccggacccg gaggtgcagg cggcgctgga ggaccttatg gacctggtgg   1980
agcttacgga ccaggtggac ccggaggacc tggagggcct ggtggtcctg gaggacccgg   2040
ttctggcgga ccttacggac ctggtggtgc ttacggacct ggtggtgctt acggacctgg   2100
tggtgcttat ggacctggtg gagctggtgg accaggtgga gctgctggac catatggacc   2160
cggtggacct tacgaccag gtggtccata cggacctggt ggagctggtg gaccaggtgg   2220
tgctggtgga ccttatggac caggaggtgc tggacctggc ggatacggac ctggaggcgc   2280
tggacctggt ggatacggac ctggcggttc tggacctgga ggcgctggac ctggtggata   2340
```

```
cggacctggc ggttctggac ctggtggtgc tggacccggt ggatatggac ctggtggtgc    2400
tggacccggt ggatacggac ctggtggtgc tggacctggc ggtgctggac ctggtggtgc    2460
tggtcctggt ggatacggac ctggcggttc tggaccaggt ggtcctggat ctggtggccc    2520
aggcggagcg ggaggttcag gtggaacaac agtaatagaa gatttggaca taacacttaa    2580
tggtccagga ggcccgataa caatctcaga agagctaaca gttggtggtc caggtgctgg    2640
aggttcagga cctggtggtg ctggaccagg aggcgcagga cccggtggtg caggaccagg    2700
aggcgcagga ccaggaggag taggacctgg tggtgctgga ggaccttatg gttctggtgg    2760
tttcggattc ggaggtgcag gcggctctgg aggaccttat gtacctggtg gagcatatgg    2820
agctggttct ggtacaccat cttatagtgg atctcgtgtt cctgatttgg tgaatggtat    2880
aatgcgttcg atgcaaggct ctggtttcaa ctatcaaatg tttggcaaca tgttatcgaa    2940
atatgcctcc ggatcaggtg catgcaattc aaatgatgtt aatgttttaa tggatgctct    3000
tcttgcggct ttgcactgtc tcagtagcca tggatcccca tcatttgggt cttctccaac    3060
cccttctgca atgaatgcat attccaactc tgttcgaaga atgttccaat tctaaggtta    3120 tactcctta aacttgaatt tattttcaaa tcattttgat gaaccttagt tactcatttg      3180
aagaaaaaaa taaatatctt tttagcagaa aaaaaaaaaa aaaaaaaaaa aaaaaaaaa      3240 aaaaaaaaaa aaaaaaaaaa aaaaaaaaaa aaaaaa                                3277

<210> SEQ ID NO 2
<211> LENGTH: 1636
<212> TYPE: DNA
<213> ORGANISM: Nephilengys cruentata

<400> SEQUENCE: 2
gcaagccaga gcgctagcag cagcagtgct tcggcctctg cattcgcaca acagtcctct     60
gcttcccttg cagcctcctc ttctttcagc caggccttcg cttcggccgc ttccgcctct    120
gccgtcggaa acgttgctta ccagctaggc ttatccgcag cacaatctct cggaatagcc    180
aatgctggag cactcgctag tgctttagct cagtctgttt cttctgtagg cgttggagcc    240
agttcaagtg cctacgccaa tgcagtcgcc ggtgccgttg acagttctt agccaatcag    300 ggtattttga acacaggcaa tgcatcttcc ctagcctcct cgttctccag tgccctctcc    360
gcctcggcag cagccgcgca atcccaatca ttcgcacaga gtcaagcagc agcttcggcc    420
ttccaacaag cagcatcaca gagtgctagc cagagtgctg cccaatctgg ttctcagtcc    480
tcttccacca ctaccaccac ctcggcctca ggaagtcaat ccgcaagcca gagcgctagc    540
agcagcagtg cttcggcctc tgcattcgca caacagtcct ctgcttccct tgcagcctcc    600
tcttctttca gccaggcctt cgcttcggcc gcttccgcct ctgccgtcgg aaacgttgct    660
taccagctag gcttatccgc agcacaatct ctcggaatag ccaatgctgg agcactcgct    720
agtgctttag ctcagtctgt tcttctgta ggcgttggag ccagttcaag tgcctacgcc    780
aatgcagtcg ccggtgccgt tggacagttc ttagccaatc agggtatttt gaacacaggc    840
aatgcatctt ccctagcctc ctcgtttct aatgcgcttt cgtcatccgc cgctaattca     900
gttggttctg gattgttatt gggtccttca caatacgttg gaagtattgc tccaagtata    960
ggaggtgctg ctggaatatc aatcgctggt cctggaattt tatcatactt acctcctgtt    1020
tctccgctga atgcacagat aatctcctct ggtttacttg cttctttggc accagtatta    1080
tcatcttccg gcttagcatc atccagtgcg acttctagag ttggcagttt agctcaatct    1140
ttggcatccg cattgcaatc ttcgggaggt acactggatg tttcgacctt cttgaatctt    1200
```

```
ctgtctccca tttctacaca aattcaagcc aatacttctc taaatgcatc acaggcgatt    1260
gtccaagttt tacttgaagc tgtagctgct ctgctgcaaa ttatcaacgg agctcaaata    1320
acttctgtca attttggcag tgtctccagc gtaaacacag ccttggcaac tgctctcgct    1380
ggttgatttt tatgtcccct ttgaagaatt ctttgcctac tggaaactta taaaatgtat    1440
aatctttatt ttatttctga tttcaactca atattgcatt cgttatcttt gcttgtctgt    1500
gcaattattg attttaaaa ttatattatg aaccctgaaa ttttcctgat aataaatatt    1560
cttgaatgcc aaaaaaaaa aaaaaaaaa aaaaaaaaa aaaaaaaaa aaaaaaaaa        1620 aaaaaaaaaa aaaaaa                                                    1636
```

<210> SEQ ID NO 3
<211> LENGTH: 1700
<212> TYPE: DNA
<213> ORGANISM: Nephilengys cruentata
<220> FEATURE:
<221> NAME/KEY: modified_base
<222> LOCATION: (1616)..(1616)
<223> OTHER INFORMATION: a, c, t, g, unknown or other
<220> FEATURE:
<221> NAME/KEY: modified_base
<222> LOCATION: (1618)..(1618)
<223> OTHER INFORMATION: a, c, t, g, unknown or other

<400> SEQUENCE: 3

```
gacaaggtgc cggagcagca gcagcagcag cagccgcagg tggagctgga caaggcggat      60
atggaggtct tggtggccaa ggagctggag ccgcagctgc agcagctggt ggtgctggac     120
aaggaggata tggaggtcaa ggtgctggac aaggtgcagc cgcagcagca gctagtggtg     180
ccggacaagg aggatatgaa ggtccaggtg ccggacaagg tgcaggtgca gccgcagcag     240
cagctggtgg tgccggacaa ggaggatatg gaggtcttgg tggccaagga gctggacaag     300
gagctggagc cgcagctgca gcagctgtg gtgccggaca aggaggatat ggaggtcttg     360
gtggccaagg agctggacaa ggagctggag ccgcagctgc agcagctggt ggtgccggac     420
aaggaggata tggaggtcaa ggtgctggac aaggtgcagc agcagcagca gctggtggtg     480
ctggacaagg aggatatgga ggcctaggtt ctggacaagg cggatatggt agacaaggtg     540
ccggagcagc agcagcagca gccgcag gtggagctgg acaaggcgga tatggaggtc      600
ttggtggcca aggagctgga gccgcagctg cagcagctg tggtgctgga caaggaggat      660
atggaggtca aggtgctgga caaggtgcag ccgcagcagc agctagtggt gccggacaag     720
gaggatatga aggtccaggt gccggacaag gtgcaggtgc agccgcagca gcagctggtg     780
gtgccggaca aggaggatat ggaggtcttg gtggccaagg agctggacaa ggagctggag     840
ccgcagctgc agcagctggt ggtgccggac aaggaggata tggaggtcaa ggtgctggac     900
aaggtgcagc agcagcagca gctggtggtg ccggacaagg aggatatgga ggcctaggtt     960
ctggacaagg cggatatggt ggacaaggtg ccggagcagc agcagccgca ggtggagctg    1020
gacaaggcgg atatggaggt cttggtggcc aaggagctgg acaaggtgct ggagccgcag    1080
ctgcagctgc tggtggttcc ggaagaggag gatatggaag tcaaggtgct ggacaaggag    1140
cagcagcagc agcagctggt ggtgcaggtc aaggtggata tggtggtgca ggttctggag    1200
ctgctgcggc ctctgcagct gcttcccgtt tgtcttctcc tgaagctagt tcgagagttt    1260
catctgcagt ttctaatttg gtttcaagtg gtcctactaa ttcggctgcc ttgtcgaata    1320
ccatcagtag tgttgtctcc caaattagcg caagcaatcc tggtctctct ggatgtgatg    1380
```

| | |
|---|---|
| tccttgttca agctcttttg gaagtcgttt ctgctcttat ccatattttg ggatcttcta | 1440 |
| gcatcggccc agttaactat ggctcagcta gccaatccac tcaaatcgtt ggtcaatcgg | 1500 |
| tttaccaagc tctaggttaa ttatgaaatc aaatttcctc aaaattattt tgatagaatt | 1560 |
| actaagtttt tgtaataatt ttgtaaaatt ggttttcaat aaatagtatg catatnanaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa | 1700 |

<210> SEQ ID NO 4
<211> LENGTH: 3487
<212> TYPE: DNA
<213> ORGANISM: Nephilengys cruentata

<400> SEQUENCE: 4

| | |
|---|---|
| gagctggtgg tgctggagga tatggcgttg acaaggcta tggtgcaggt gcaggagctg | 60 |
| gggctgccgc cggtgcagga gctggtggtg ctggaggata tggcgctgga caaggctatg | 120 |
| gtgcaggtgc aggagttggt gctgccgccg ctgctggagc aggtgcagga gttggtggtg | 180 |
| ctggaggtta cggaagaggt gctggagccg agctggagc tggagctgga gctgctgccg | 240 |
| gagctggagc tggagctgct gctggagcag gagctggtgg tgctggagga tatggcgctg | 300 |
| gacaaggcta tggtgcaggt gcaggagttg gtgctgccgc cgctgctgga gcaggtgcag | 360 |
| gagttggtgg tgctggaggt tacgaagag gtgctggagc tggagctggt gctggtgctg | 420 |
| gtggtgcagg aggttacgga agaggtgctg gtgctggagc tggagctggt gcaggagctg | 480 |
| gtggtgctgg aggatatggc gctggacaag gctatggtgc aggtgcagga gctggtgcag | 540 |
| ccgccgctgc tggagccggt gcaggtgctg gtggtgctgg aggttacgga agaggtgctg | 600 |
| gtgctggagc tggagctggt gcaggagctg gtggtgctgg aggatatggc gctggacaag | 660 |
| gctatggtgc aggtgcagga gctggtgcag ccgccgctgc tggagccggt gcaggtgctg | 720 |
| gtggtgctgg aggttacgga agaggtgctg gtgctggagc tggagctggt gcaggagctg | 780 |
| gtggtgctgg aggatatggc gctggacaag gctatggtgc aggtgcagga gctggtgcag | 840 |
| ccgccgctgc tggagccggt gcaggtgctg gtggtgctgg aggttacgga agaggtgctg | 900 |
| gtgctggagc tggagctggt gcaggtgctg gtggtgctgg aggttacgga agaggtgctg | 960 |
| gagctggagc tggggctgga gctgctgcag gagcaggagc tggtggtgct ggacgatatg | 1020 |
| gcgctggaca aggctatggt gcaggtgcag gagctggggc tgccgccggt gcaggagcag | 1080 |
| gtggtgctgg aggatatggc gctggacaag gctatggtgc aggtgcagga gctggtgctg | 1140 |
| ccgccgctgc tggagcaggt gcaggagttg gtggtgctgg aggttacgga agtggtgctg | 1200 |
| gagccggagc tggagctgga gctggagctg cttctggagc tgctgctgga gctgctgctg | 1260 |
| gagcaggagc tggtggtgct ggaggatatg gcactggaca aggctatggt gcaggtgcag | 1320 |
| gtgctggagc tggtgctggt gctggtggtg caggaggtta cggaagaggt gctggagctg | 1380 |
| gagctggtgc aggagctggt ggtgctggag gatatggcgc tggacaaggc tatggtgcag | 1440 |
| gtgcaggagc tggtgcagcc gccgctgctg agacggtgc aggtgctggt ggtgctggag | 1500 |
| gttacggaag aggtgctgga gctggagctg ggctggagc tgctgcagga gcaggagctg | 1560 |
| gtggtgctgg aggatatggc gctggacaag gctatggtgc aggtgcagga gctggggctg | 1620 |
| ccgccggtgc aggagcaggt ggtgctggag gatatggcgc tggacaaggc tatggtgcag | 1680 |
| gtgcaggagc tggtgctgcc gccgctgctg agcaggtgc aggagttggt ggtgctggag | 1740 |
| gttacggaag aggtgctgga gccggagctg gagctgctgc cggagctgga gctggagctg | 1800 |

```
ctgctggagc aggagctggt ggtgctggag atatggcac tggacaaggc tatggtgcag      1860
gtgcaggtgc tggagctggt gctggtggtg caggaggtta cggaagaggt gctggtgctg      1920
gagctggagc tggtgcagga gctggtggtg ctggagaata tggcgctgga caaggctatg      1980
gtgcaggtgc aggagctggt gcagccgccg ctgctggagc cggtgcaggt gctggaggtg      2040
ctggaggtta cggaagaggt gctggagctg agctggggc tggagctgct gcaggagcag      2100
gagctggtgg tgctggagga tatggcgcta gacaaggcta tggtgcaggt gcaggagctg      2160
gggctgccgc cggtgcagga gctggaggtg ctggaggata tggcgctgga caaggctatg      2220
gtgcaggtgc aggagctggt gcagccgccg ctgctggagc cggtgcaggt gctggtggtg      2280
ctggaggtta cggaagaggt gctggagctg agctggagc tggggctgga gctgctgcag      2340
gacaaggcta tggttcaggt gcaggtgctg agctggtgc cagtgctggt ggtgcaggaa      2400
gttacggaag aggtgccgga gctggtgctg ccgccgcttc tggagccggt gctggaggat      2460
atggcgctgg acaaggctat ggtgcaggtg caggagctgt tgcttctgcc gctgctggag      2520
ccggttcagg agctggtggt gctggaggtt acggaagagg tgccgttgct ggttctggag      2580
ctggtgccgg agcaggagct ggtggtgctg gaggatatgg tgcaggagct ggtgctggtg      2640
ccgctgctgg agcagttgct ggtggttctg gaggatatgg cggcagacaa ggcggttata      2700
gcgcaggtgc gggagctggt gcggcggctg ctgctggagc aggtgcaggt ggaactggag      2760
gctacggaag aggttctggt gctggagccg cagctggtgc tgctgctgga gctggtgctg      2820
ctggaggata tggtggctat ggcgcaggtg ctggagctgg tgccggtggt gctagaggtt      2880
acggaggagg tgctggtgct ggagcaggtg ccgctgctgg aggttatgga agaagagcag      2940
gtggatccat tgtaggaact ggaataagtg caattctctc tggaactggt tctagctatt      3000
ccgtttcttc cggcggttac gcctctgcgg gtgtaggtgt tggatccact gttgcatcta      3060
ccacatctcg tttgagttca gcacaagcat cttctagaat atctgctgct gcttctactt      3120
taatatctgg aggttacttg aatacatctg ccttaccatc agtcatttct gatttgtttg      3180
cccaagtcag tgcttcatcc cctggtgtat cagatagtga agttttgatt caagttttgt      3240
tggaaattgt ttcttccctt atccatattc tcagttcttc cagtgtaggg caagttgact      3300
tcaattctgt tggttcgtct gctgcagctg ttggacagtc catgcaagtt gtcatgggtt      3360
aattaaaatg gctgtctctc cccaattaat tcttttaaata cagttaagca tttaaaaata      3420
aaaaataatg taaaatttc tgcataaata aaaatatttt cctgcttgga aaaaaaaaa      3480 aaaaaaa                                                                3487
```

<210> SEQ ID NO 5
<211> LENGTH: 1163
<212> TYPE: DNA
<213> ORGANISM: Nephilengys cruentata

<400> SEQUENCE: 5

```
ggaaccagct ccagcacctg cgccatagcc accatatcct ccagcagcac cagctccagc       60
agcagcacca gctgcggctc cagcaccaga acctcttccg tagcctccag ttccaccagc      120
acctgctcca gccgccgccg ccgcaccagc tcccgcacct cgctataac caccttgtct       180 gccgccatat cctccagaac caccagcacc tactccagca gcggcaccag ctcctgcacc      240
atatcctcca gcaccaccag ctcctgctcc ggcaacagca ccggcacctc ttccgtaacc      300
tccagcacca ccagctcctg aaccggctcc agcagcggca gaagcaacag ctcctgcacc      360
```

| | |
|---|---|
| tgcaccatag ccttgtccag cgccatatcc tccagcaccg gctccagaag cggcggcagc | 420 |
| accagctccg gcacctcttc cgtaacctcc tgcaccacca gcacgggcac cagctccagc | 480 |
| acctgcacct gaaccatagc cttgtctggc gccatatcct ctagcaccac cagctcctgc | 540 |
| accggcggca gccccagctc ctgcacctgc accatagcct tgtccagcgc catatcctcc | 600 |
| agcaccacca gctcctgctc ctgcagcagc tccagcccca gcccagctc cagcacctct | 660 |
| tccgtaacct ccagcaccac cagcacctgc accggctcca gcagcggcgg ctgcaccagc | 720 |
| tcctgcacct gcaccatagc cttgtccagc gccatatcct cctgcaccag ctccagctcc | 780 |
| agcaccagca cctcttccgt aacctcctgc accaccagca ccaacaccag ctccagcacc | 840 |
| tgcaccttca ccatagcctt gtccagtgcc atatcctcca gcaccaccag ctcctgctcc | 900 |
| agcagcagct ccagctccag ctccggcagc agctccagct ccagctccag cacctcttcc | 960 |
| gtaacctcca gcaccaccag cacctgcccc ggctccagca gcggcagcag caccagctcc | 1020 |
| tgcaccatag ttttgtccac cgccatatcc tccagcacct ccagctcctg caccagctcc | 1080 |
| ggctccagca cctacacctc ttccgtaacc tccagcacca ccagtaccgg caccagctcc | 1140 |
| tgcacctgca ccatagcctt gtc | 1163 |

<210> SEQ ID NO 6
<211> LENGTH: 1292
<212> TYPE: DNA
<213> ORGANISM: Nephilengys cruentata

<400> SEQUENCE: 6

| | |
|---|---|
| ggaaccagct ccagcacctg cgccataacc accttgtctg ccgccatatc ctccagaacc | 60 |
| accagctcct gctccagcag ccgcaccagc accagctcct gcaccatatc ctccagcacc | 120 |
| accagctcca gcaccacttc cgtatcctcc agcgccacct gcacctgctc cagcagcggc | 180 |
| tgcagcacca gctccagcac ctcttccgta aaatacggct ggcccataag atgtcaatgt | 240 |
| tgttgtaacc gacgaagcag cactcgaagc agcggaagat gcggtacttt cattaataga | 300 |
| accagtgtta gctaaaacat tgccaatagc tgaagatatt gcatttgcat aagctgcagc | 360 |
| atctgcaaca gcaccaccca atgatgaaac atacccacca acagcagcca gtaaattgtt | 420 |
| catagcattg gcatcgaggc caagttgatt tccaacattt tgagcaacgc tcgttgcaac | 480 |
| gctcacagcc tgatcagtag aagttgtggt ggagatcatt tgaacaaaat ctcctgatga | 540 |
| gaggagattg gatgagaggg attgtgcgaa agcgttttca gctgcacttc ctgctccagc | 600 |
| accagctcca gcacctgcac catagccttg tccgacgcca tatcctccag caccaccagc | 660 |
| tcctgctccg gccccagctc cagcaccagc acctcttccg taacctccag caccaccagc | 720 |
| accggcacca gctccagcac ctgcaccagc tccagcacct gcaccatagc cttgtcctgc | 780 |
| accatatcct ccagcaccac cagttcctgc accggctcca gcagcggcgg cagcaccagc | 840 |
| tcctgcacct gcaccatagc cttgtccagc gccatatcct ccagcaccac cagctcctgc | 900 |
| tccagcagcg gcggcagcac cagctccggc tccagcacca gcacctcttc cgtaacctcc | 960 |
| agcaccacca gcaccggcac cagctccagc agcggcggct gcaccagctc ctgcacctgc | 1020 |
| accatagcct tgtccagcgc catatcctcc agcaccacca gctcctgctc cggcggcagc | 1080 |
| tccagcacca gctccggctc cagcaccagc acctcttccg aaacctccag caccaccagc | 1140 |
| acctgcaccg gctccagcag cggcggctgc accagctcct gcacctgcac catagccttg | 1200 |
| tccagcgcca tatcctccag caccaccagc tcctgctccg gcggcagctc cagcaccagc | 1260 |
| tccggctcca gcaccagcac ctcttccgta ac | 1292 |

<210> SEQ ID NO 7
<211> LENGTH: 2172
<212> TYPE: DNA
<213> ORGANISM: Nephilengys cruentata

<400> SEQUENCE: 7

```
tgctcctcgt cctctaccag ctcctgctcc tcgtcctcta ccagctcctg ctcctcgtcc      60
cctaccagca cctttgccag ctcctcttcc aagaccacgc ccagcaccca tagtttctca     120
agtgcaacag gcatccgctc tacaggcaca gtcacaacag tctgcttttg ctcaatccca     180
acaatcgtcc attgcacaat ctcagcaagc ctctgtcgcc caatcccaac gagcctccgt     240
ctctcaatcc cagcaatcta gtaatgcgtt ttcttctgca gcatcatttg gagcttctag     300
cgtagcatcc agtgcttcga cttactttaa ttcgggaata gtacaaagta gcatcgcgtc     360
gtcgttgcag tcttccagtg ctctcagttc cattgcctac ggccagacaa ccgcttctat     420
caacgatata gcatcggcag tcgctggcag cattgcaaat tcaatcggac tctcgcaaca     480
aaccgttcaa agtattatta gtcaacaact agccagtgca ggatccggag catctgctca     540
aacattggct tcattgatat ccagcgcagt ttcctccttg gttcaacaat ctggatcggt     600
atcagccgga caagaacaga gtatttcgca agcactttcc agttctatct cgagttcttt     660
gaatcaattg gtagctgcaa gacctctacc agctcctgct cctcgtcccc taccagcacc     720
tttgcctgct cctcttccaa gaccacgccc agcacccata gtttctcaag tgcagcaggc     780
atccgctcta caggcacagt cacaacagtc tgcttttgct caatcccaac agtcgtccat     840
tgcacagtct cagcaagcct ctgtcgccca atcccaacaa tcctccatct cccaatccca     900
acaagcctcc gtctctcaat cccagcaatc tagtaatgcg ttttcttctg cagcatcttc     960
tggagcttct agcgtagcat ccagtgcttc gacttacttc aattcgggca tagtacaaag    1020
cagcatcgcg tcgtcgttgc agtcttccag tgctctcagt tccattgcct acggccagac    1080
aaccgcttct atcagcgata gcatcggcag tcgctggc agcattgcaa attcaatcgg    1140
actctcgcaa caaaccgttc aaagtgttat tagtcaacaa ctagccagtg caggatccgg    1200
agcatctgct caaacattgg cttcattgat atccagcgca gtttcctcct tggttcaaca    1260
atctggatcg gtatcagccg gacaagaaca gagtatttcg caagcacttt ccagttctat    1320
ctcgagttct ttgaatcagt tggtagccgc aagacctcta ccagccctg ctcctcgtcc    1380
cctaccagca cctttaccag ctcctctttc aagacctcga ccagttccag tccaaagacc    1440
tcaacccgta ttttcaccca gtcccgctcc tgcctatgct cctgcccat tcactcagca    1500
gtcgactttt gctcagtctc aacaagcttc tcttgctcaa tctcaacaac aagcatctat    1560
cgctcgatcc caacaagcgt ctctagcgca atctcaacaa tcggcttttg ctcaatccca    1620
acaagtagct acagcacaat ctcagcaatc ttctggtgga ttctccacat catctactgg    1680
agcttctcaa atcagttctt cagccataag tacttcttcg ggatctgcat ggctaattc    1740
cgcacaacaa ctcacatcac ctgcagcctc tcaaagaata tctcagttat ccaattccct    1800
agcatctgca gtttctggtg gacaggtcaa ctatgcagcc ttatctaatt ctattgctag    1860
tgctgcaagt caaattggag gtggatctgg attatccaaa acggaagttc taattgaaac    1920
tctcttagaa accctggctg ctttattgga atctctttct cttcctggat cagctagtgg    1980
tggaagtcaa ttcgctcaag caatgcttgc agctcttgca taaaatgtgg ttaataacaa    2040
ataattttgt tggaatgctt atgaatattt ttaggggaat atatgatata cactttaaat    2100
```

| | |
|---|---|
| gaataatatt gtataacttt tgttaatgg gaaataaaat ttattagcaa gcatcaaaaa | 2160 |
| aaaaaaaaaa aa | 2172 |

<210> SEQ ID NO 8
<211> LENGTH: 924
<212> TYPE: DNA
<213> ORGANISM: Nephilengys cruentata

<400> SEQUENCE: 8

| | |
|---|---|
| atgtggaatc gacaagtctt accaatatat attttggtaa ttgtctcgct agcgatactt | 60 |
| actacgcatg tttccacgtc gaaacaacgt ccttttttata taatgggaca catggtaaac | 120 |
| agtatcgaag aaatatcgga attcctagaa agaggatcca acgttttgga atcagatgtt | 180 |
| caattctttt caaacggatc tgtaaaagca gtccgtcatg gatttccttg cgattgtggt | 240 |
| agattttgcg agaacacagc caatctggcg gattacttgc agagtgttcg atacatcact | 300 |
| gatccagata cacctgatag ttattacaac caactggtac tgcagttctt tgatttgaag | 360 |
| ctgagtacgt ccgaaaataa aagacaatct ggacgagaga tagctcacca tgttctggat | 420 |
| tatttatggg gtgaagaagg cgaaagagag aaagagatcc gagttgtaat ttacttcgaa | 480 |
| aagcttgaag agaaggatgt aatccttgga tttatggacg tattcaaact ccgaaaccaa | 540 |
| acatcgcgtc tcagagatgt cggttttgac ggtggaactg gaaacatttc agatatcgct | 600 |
| agaatgttct ccaaatttaa tataaaagat aatatttggc ttggagatgg tgcaacaaat | 660 |
| tgttttgaac ttttaaaatc atttgtgcgt ctaaagaatg caatagacaa ccgagattcc | 720 |
| aggaaaggtt tgtttcaaa aatttatcaa tggactaatg atataaaaac aacaatgatg | 780 |
| cgttccctaa gacttggagt ggatgggatg atcactaaca aacctgagag actcctggag | 840 |
| gttctgcaag aacccgaatt tgcgaaggat ttcagattag caacaattta cgacgatcct | 900 |
| ttcgaatact tctgtgacga gtga | 924 |

<210> SEQ ID NO 9
<211> LENGTH: 2070
<212> TYPE: DNA
<213> ORGANISM: Avicularia juruensis

<400> SEQUENCE: 9

| | |
|---|---|
| cgtactctct agcaagctcc attgcaagcg ctgcatcctc gagtgcatct tcggcagcag | 60 |
| cagcggcgtc atcttcttcc gcagcagcag gagcagccgc ggcttcggaa gcagcagctt | 120 |
| ctgccgccgc cacttccacg acaacaacaa caagtacttc tcgtgccgca gcagcagcat | 180 |
| ccgccgcagc cgcggcctct gcctcgggag ccgccggcgc agcgggagca gcatcagccg | 240 |
| ctagcgctgc ttcagcttct tcgtccttgc aacagtctct gggatctgcc ttagcacaaa | 300 |
| gtagctcatt tgcagcagcc ttcgcccaag caagtagcgc tgcttctgca gcagccatag | 360 |
| catatgctct tgcacagacc gtggcgaatc aaatcggttt ctcttcctac tcctcagctt | 420 |
| tcgcaagagc agcttcatca gccgtataca gcataggggg cttggcttct gcatctgcat | 480 |
| atgcctttgc ttttgccagc gccttttcac aagttctctc aaattacggt ttacttaaca | 540 |
| taaataacgc gtactctcta gcaagctcca ttgcaagcgc tgcatcctcg agtgcatctt | 600 |
| cggcagcagc agcagcggcg tcatcttctt ccgcagcagc aggagcagcc gcggcttcag | 660 |
| gtacagcagc ttctgccgcc gccacttcca ccaccacaac aacaagtact tctagagccg | 720 |
| ctgcagcagc atccgccgca gccgcggcct ctgcctcggg agccgccgac gcagcgggag | 780 |
| cagcatcagc cgctagcgct gcttcagctt cttcgtcctt gcaacaatct ctgggatctg | 840 |

```
ccttagcaca aagtagctca tttgcagcag ccttcgccca agcaaatagc gctgcttctg      900
cagcagccat agcatatgct cttgcacaga ccgtggcaaa tcaaatcggt ttctcttcct      960
actcctcagc tttcgcaagc gcagcttctt cagccgtatc cagcttaggg ggcttcgctt     1020
ctgcatctgc atatgccttt gcttttgcca gcgccttttc acaagttctc tcaaattacg     1080
gtttacttaa cataaataac gcctactctc tagcaagctc cattgcaagc gctgcatcct     1140
cgagtgcatc ttcggcagca gcagcggcat catattcctt ctcagcaaca ggagcagcct     1200
cttcggcagc agtaggtgcg gcagcgacat ctggtgcagc gacatctggt gcagcgactt     1260
cctctagctc tgcgacgggt gtcggaggaa gtgtctcctc tggagcatca cccgcttccg     1320
ctggaactgc aacaggtggc ggtatctcat ttctacctgt ccagacacaa cgtggtttcg     1380
ggcttgtgcc ctctccttca ggtaatattg gtgcaaattt tcctggttct ggtgaatttg     1440
gtccatcacc tttgacatca ccagtttatg gtccgggtat tcttggccct gggcttgtcg     1500
tgccctcatt acaggggctg ttgccacctt tatttgtttt accatcgaat tcggcaactg     1560
aaagaatttc gtccatggta tcgtctttgt tgtccgcagt ttcttccaat ggattggatg     1620
cttcttcttt tggtgatacc atagcttccc tggtttcgca gatatccgtg aataattccg     1680
atctttcttc gtcacaagtc ttgcttgagg cgctccttga aattttgtct ggaatggtac     1740
aaatcctttc ttatgctgaa gtcgggactg ttaatacgaa gaccgtgagt tcaacttccg     1800
ctgctgtggc tcaagctatc tcttcggctt tttcgggaaa tcagaattct tgagctgcct     1860
aatgaaggtt ttttttcatc aaatattttt aaaatattat gacccactga tttaattttt     1920
attactatca atattggaag tgaaatttaa taggtgttgt tatttctgct gtgtaatgtt     1980
ggtaatggtt gtaaatgtaa ctagtatggt attggtaaaa aaaaaaaaa aaaaaaaaa      2040 aaaaaaaaa aaaaaaaaa aaaaaaaaa                                       2070
```

<210> SEQ ID NO 10
<211> LENGTH: 1925
<212> TYPE: DNA
<213> ORGANISM: Avicularia juruensis

<400> SEQUENCE: 10

```
acaacaagca cttctacagc cgcagcagca gccgcagcag cggacttcgg ctcgggagcc       60
gcccgcgcag cgcaaacagc atcagccgct agcgctgctt cagcttcttc gtccttgcaa      120
cagtctttgg gatctgcctt agcacaaagt agctcatttg cagcagcctt cgaccaagca      180
aatagcgctg cttctgcagc agccatagca tacgctcttg cacagtccgc ggcgaatcaa      240
gtcggtttgt cttcctactc cgcagctatc tcaaacgcag ctgcagcagc cgtaggaagc      300
gtaggtggct acgcttctgc atctgcctat gcctttgctt ttgccagcgg cgtttcacaa      360
gttctatcaa attacggttt aattaaccta agtaacgcct tattttttagc aagttcgata      420 gcaaacgctg catcggcgag tgcatcttcg gcagcagcag cggcgtcatc ttcttccgca      480
gcaacaggag cagccgcggc tttgggaggc gctggttctg ccgccgccac ttccaccacc      540
acaataacaa gcacttctac agccgtagca gcagcctctg gctcgggagc cgcccgcgca      600
gcgcaaacag catcagccgc tagcgctgct tcagcttctt cgtcccttgc acagtctttg      660
ggatctgcct tagcacaaag tagctcattt gcagcagcct tcgaccaagg caatagcgct      720
gcttctgcag cagccatagc atacgttctt cacagtccgc ggcgaataa agtcggtttg      780 tcttcctact ccgcagctat ctcaaacgct gcttcagcag ccgtagaaag cgtaggtggc      840
```

```
tacgcttccg catctgccca tgcctttgct tttgccagcg ccgtttcaca agttctatca      900
aattacggtt taattaacct aagtaacgcc ttgtccctag caagttcgat agcaaacgct      960
gtatcggcga gtgcatcttc ggcagcagct gtgtcatctg ctgcagcagc aacaggtgca     1020
acctcttcgg cagcagtagg tgcagcagcg acatgtgggg cagcgacttc cgctagttct     1080
gcgacgggcg tcggagaaac tgttgcctgt gcaacatcgc ccgcgtccac tggaaccgcg     1140
gcaggtggcg gtatctcatc tttacctgtt cagacacaac ctggttttgg gttttgctc      1200 tctccctcag gtaatattgg tccaagtgtt tctggttctg gtgggtttgg tccatcacct     1260
ttgccatctc cagcttctga cggatttagc ccatcgcctt tgccatcaca agtttatggt     1320
cctggtattc ttggtcccgg tctcgtcgca ccttcgttag aagggctgtt gccaccttta     1380
tcaattttgc catcggattc tgcaaatgaa agaatttcgt ctgtagtatc ttctttgttg     1440
gccgccgttt cttccaatgg attggatgct tcttctcttg gcgataactt agcttcactg     1500
gtttcgcaga tatccgcgaa taatgccgat cttcttcgt cacaagttat ggttgaggct      1560
cttcttgaag ttttgtctgg aatagttcag atcctttctt atgctgaagt tggggctgtt     1620
aatacggaaa ccgtaagttc aacttcctct gctgtggctc aagctatttc ttcggctgtt     1680
ttgggataat caaaattctt gagctgccta atgaaactgt ttttttttta acaaatattt     1740
taaaaatatt atggcccact gatttaattt tcattagtat caatgttgga agtgggaatt     1800
taatatgttt tgtttatttc tgctgtgtaa tgttgttaat ggttgtatat gtaactagta     1860
tggtattggt aataaaaaca ttgcatttga aaaaaaaaa aaaaaaaaa aaaaaaaaa        1920 aaaaa                                                                 1925

<210> SEQ ID NO 11
<211> LENGTH: 1874
<212> TYPE: DNA
<213> ORGANISM: Avicularia juruensis

<400> SEQUENCE: 11
gttcgggatc tggttctgga agtggagcag gtctggtgg aggaagtggt gcgggatctg       60
gttctggaag cggagcagga gcaggatctg tagtggctc aggttcagga agtggagcag      120
gatctggtag tggctcaggt tcaggaagtg gagcaggttc aggtagtggc tcaggttcag     180
gaagtggagc acgatctggt agtggctcag gttcaggaag tggagcaggt tcgggtagtg     240
gctcaggttc aggaagtggg gcaggtgcag gtagtggttc aggttcagga agtggagcag     300
gttcaggtag tggagcaggt tcaggtagtg gctcaggttc aggaagtggg gcaggttcag     360
gtagtggctc aggttcagga agtggggcag gcgcaggtag tggctcaggt tcaggacgtg     420
gagcaggttc aggtagtggt tcaggttcag gaagtggagc aggttcaggt agtggctcag     480
gttcaggacg tggagcaggt tcaggtagtg gctcaggttc aggaagtggg gcaggtgcag     540
gtagtggctc aggttcagga agtggagcag gttcaggtag tggctcaggt tcaggaagtg     600
gagcaggttc aggtagtggc tcaggttcag gaagtggagc tggatctggt agtggctcag     660
gttcaggaag tggagcagga tctggtagtg gctcaggttc aggaagtgga gcaggttcag     720
gtagtggctc aggttcagga agtggagcag gttcaggtag tggctcaggt tcaggaagtg     780
gagcaggctc aggtagtggc tcaggttcag gaagtggagc aggagctggt agtggttcag     840
gttcatgtag aaaagatgca ggtggtcatg atggcggata tgggaaaaag cttggttttg     900
aattcggtac gcctgcagca gcagctgtta cccttggacc tggagctgga caacaaggcc     960
caggtggagc tggacaacaa ggaccaggag gccaaggacc atatggacca gttgctagcg    1020
```

```
ccgccgcagc tgttgctgga ggttatggac ctggagcttt accacaagga ccagcacgcc   1080
aaggaccttc cggtcctgtt tcttcagcac cagttgcatc ggcagctgct gctcgccttt   1140
cttctcctca ggctagttct agagtatctt cagcttttt ttctttggta tcaagtggtc    1200
caactagtcc tggtgcactt tctaatgcca tcagtagtgt tgtttcacaa gttagtgcaa   1260
gcaatccagg tctctctggt tgcgatgtac tcgtgcaagc attgctggaa attgtatccg   1320
cccttgtatc tatccttgcg tcatctagta tcgggcaaat caactatgga gcttccgctc   1380
agtatgcctc tttggttggc caatctgtaa atcaagctct tcgttattaa tttagcaaat   1440
gatttgcaaa cttttttcaa tgttactaac acatactttt aaaatttctc aataaatttg   1500
aagcatatta tatttcctct tgtgttattt atttgttaca tgcggagatg aacattgatc   1560
ctgttacaaa tttatattta aaattatttc tttaaataat cgaaagtgga ttaaaagtac   1620
ttttacaaaa ctttgcattt agatttcatg aaaaaatatt tgtttcagcg ttagtaaacg   1680
ataaacattt ttggtcctat caattattaa ttttttttat aatcttttga ttgccatatt   1740
tataatttct ttaaaattat ttacgatttc tcctacattt tcttttttaa atccattttc   1800
atgtgtcttt caagaatttt gtgattaaat gtggtatttt tcatgataaa aaaaaaaaa    1860 aaaaaaaaaa aaaa                                                     1874

<210> SEQ ID NO 12
<211> LENGTH: 1922
<212> TYPE: DNA
<213> ORGANISM: Avicularia juruensis

<400> SEQUENCE: 12
aacaaacttt aagcatgact tcgtttaccc aaatcgcaac aacgctttt tttgttttcg     60 tgggggttgc aatcgccagg gacaacaatc tttctccaaa cgttccatgg ataactcagg    120
aagatggcga agttttttg ttagcctttg aagaagccat atctgaaaaa atgcaacccg     180
atgggataag tgacttagaa tttctgtttg gaagcttgct gtcattaata cctcagagat    240
cggggagtct gtctgtcgct aggttacaag cacttaatat ggctttggca tctattatcg    300
ccgaaattgt aagaatagat gggagaggat ccatggaaga aaaaattgaa ttcgttcgtg    360
aggggctcat aaaggcattc ctagcaacat caggcttcgt caatacagca cttataaagg    420
aagttttaag tatgattcga cttttctatg aggaagagga aggtgataac acaatagacc    480
agaacttccc tcagcaggaa tacccagaag ttacttccca attcgactcg gcgggtaaat    540 tcgaaaccctt tgattcagta gctggtcaac aagcctcaac agaagcaagt cagtcttcat    600
cgactgtgtc cacaacgaca tcgactagtc agacatactc tgaacaaacg gccagctcat    660
cggatgttgc ctccacagca gcaacatcag aagcatcttc ccgttttaca caatacgtga    720
cgtctttctt gctgcaggat ttagaatttg ttgatcagta taacaccata gcatcttcag    780
gtatagctag tacgttagca tccgcatctg ctgaagctgt agcatattca atcggtcaag    840
gcagtatcgc gtcagctata gcatctgctg tttctcaggc tacagcaaat atctcctttg    900
tgactgtacc ttttgttttc gtccatgctt ttgcatctgc ggtgtcagag acccttctg    960 cttttggtgt gttgaacttg gacaatgtaa atacactagc aagtgaattc gcaaattctc   1020
tgtttaatgc tatattaaca gcttcagctt cttctacgac atcagcttca gcttcttcta   1080
cgacatcagc ttcagcttct tctacgacat cagcttcagc ttcttctacg acatcagctt   1140
cagcttcttc tgagacatca gcttcagctg catcagcttc aacagcacta caaacagatt   1200
```

-continued

```
ctactgctgc aggatcctta gcttcgtccg gaacttcaag tgcgaactac ggaccatcgt    1260
ttggtattga agtccgtttt tcccctgctt ttggggctgg aagtgggccg aacacttttg    1320
atttcctcac tccatcgcca agcattcctg ctcttccaac caatccagaa ctttctcgct    1380
actcaccatt aatatctgag ctgttacagt ccccttctgg tttaaagtct cctgcagcag    1440
acgaaagaat tgcttcttca gtaccactgc ttgctttagc ggtaacaaat ggctttaatc    1500
cttctctctt ctcagttgtt ttgtcttcgt tagtttctca gatttctcaa agctctagtt    1560
ttacgtcatc tcaggttctc attgaagcaa ttttggagat aatatccggt atgttgaaca    1620
tcctaacttc agcacaactt ggtttggtga gtacagcttc actggctgca acagtttctt    1680
ctattgtcca gtctatttcc agttcaataa ttgcatgaat caacatgtta agtatcata    1740 tgaaaaaaaa aagcagaaac tgtagaaaaa ttaaatttga ctttcaggct aagctgacgc    1800
aaaaaaaaaa aaaaaatatg catttatata tacgtttaag taacaaatca tgtagcctca    1860
tttacctaaa atgcaaactg tactaaaata aaaaatcttt ctttttctcc aaaaaaaaaa    1920
aa                                                                   1922
```

<210> SEQ ID NO 13
<211> LENGTH: 2588
<212> TYPE: DNA
<213> ORGANISM: Avicularia juruensis

<400> SEQUENCE: 13

```
acggcactgg tggcagacat gatgaggatg ataagggacg aactggtgaa agacatgatg     60
aaggttccaa aggaggaact aacgaagac atggtgaaa ttccagagaa ggccctgacg       120
gaagacatgg tgaacgtccc agaggaggag tagacggaag acatggtgaa ggttgcagag     180
aaggcgctga cggaagacat agtgaaggtt ccagaggagt tctggcgaa agacatggtg      240 aaggttccag aggaggagta gacggaagac atggtgaagg ttgcagagaa ggcgctgacg     300
gaagacatag taaaggttcc agaggaggcg ctggcgaaa acatggtgaa ggttccagag      360
gaggagtaga cggaagacat ggtgaaggtt gcagagaagg ctctgaaaga agacacggtg     420
aaggttccag aggagacgca gacggaaggc acgtgaaggt ttacaaagga ggctctgaaa     480
gaagacatgg tgaaggtttc agaagaggag tagacggaag acatggtgaa ggttgcagag     540
gaggccctga agaagacat ggtgaaggat ccagaatagg aggtgacgga aacatggtg      600 aaggttccag agaaggcgct catggagggc atggtgaagg gcccagagaa ggagtagacg     660
gaggacatgg tgaacgttcc agaggaggag tagacggaag acatggtgaa ggttccagag     720
aaggagctga tggaggacat ggtgaaggtt caagagaagg agtagatgga agacatggcg     780
aaggttcgag aggaggagtg gacggaagac atggcgaagg ttcgagagga ggttttgacg     840
gaagacatgg tgaaggttgc aaaggaggcc ctgaaagaag acatggtgaa ggatccagaa     900
taggaggtga cggaaaacat ggtgaaggtt ccagagaagg cgctcacgga gggcatggtg     960
aagggcccag agaaggagta gacggaggac atggtgaacg ttccagagga gaagtagatg    1020
gaggacatgg tgaaggtacc agagaaggcg ctgacggagg atatggtgaa ggttccagag    1080
aaggcgatga cggaagacat ggtgaacgtc cagaggagg agtagacgga agacatggtg    1140
aaggttgcag agaaggcgct gacggaagac atagtgaagg ttccagagga ggcgctggcg    1200
aaagacatgg tgaaggttcc agaggaggag tagacggaag acatggtgaa ggttgcagag    1260
aaggcgctga cggaagacat agtgaaggtt ccagaggagg cgctggcgaa agacatggtg    1320
aaggttccag aggaggagta gacggaagac atggtgaagg ttgcagagaa ggctatgaaa    1380
```

```
gaagacatgg tgcaggttgt agaggaggaa tatacagaag acatgatgaa ggttacaaag    1440
gaggctctga aagaagacat ggtgaaggtt tcagaagagg agtagacgaa agacatggtg    1500
aaggttgcag aggaggccct gaaagaagac atggtgaagg atccagaata ggaggtgacg    1560
gaaaacatgg tgaaggttcc agagaaggcg ctcacggaag gcatggtgaa gggcccagaa    1620
aaggagtaga cggaggacat ggtgaagggc ccagagaagg agtagacgga ggacatggtg    1680
aacgttccag aggaggagta gacgaagac atggtgaagg ttccagagaa ggcgctgacg     1740
gaggtcatgg tgaaggttcc agagaaggag tagatggaag acatggcgaa ggttcgagag    1800
gaggagtgga cggaagacat ggcgaaggtt cgagaggagg ttttgacgga agacatggtg    1860
aaggcagaga aggcgctgac ggaggacatg gtgaaggttc agagaaggga gctgagggag    1920
gatatgggga aggttccaga ggaggagtag acggaggaca tggtgaaggt tccagagaag    1980
gcgtagacag aggccatggt gaaggttcca gagaagacgc tgacggagga tctgctgaag    2040
gttccagaga aggcgatgac ggaaaacgtg gtggtgacgc tggtggtgat gcaaaagtcg    2100
cctttgaaag cgacagtgga tggaaagggt atcaacagtc atggggatat gaagaccgtt    2160
atagttttgg aaaattaaat ggacatgatg ctagtgaaaa ttaaaaccgt agggacaacg    2220
accacggaag tgtcgctaga aaagtaagtt acaatggaat tgacattaaa aacaaatcg    2280 gattttcagt agaaggagaa aaacgtttct gatatatttc ctttgacgta ctcttagtcc    2340
aattagtttg tgacactctc tgcaagcatt tggaacgaat gtatttacat gatgctattg    2400
gaattttgga attgacatta aatatttctg cttatgaac ttaacaatat gacaaaagca     2460
cgtgttttta ccttataatg aatctttcaa atgtgcaaca tcattgcttg cagaattaat    2520
ctaataaata aaggatgttc tggaaaaaaa aaaaaaaaaa aaaaaaaaaa aaaaaaaaa     2580 aaaaaaaa                                                             2588
```

<210> SEQ ID NO 14
<211> LENGTH: 2090
<212> TYPE: DNA
<213> ORGANISM: Parawixia bistriata

<400> SEQUENCE: 14

```
gccgttcaag cattgtctag ttctctcggc atcgacggaa ataacttggc aagaatagcg     60
tcacaaacaa tccttagagt tcccgcaggt tcagacactt ctgcatacgc tcaagcattc    120
tctactgctt tgttcaattc tggagttctg aatgcaagta acgttaatac attgggatca    180
caagtcgtgt caacactttt aagaggaata tcaagtacgg cacaaggcct tggcttaaac    240
gtagacgctg gaagtgtaca gagcgacatt agttctagca gcagcttcct atccacaagc    300
tcttcatcga ccagttcctc tcagacaact gctgcttcga catctggatt cacaggagcc    360
tcataccccg gacctcaagt ctcacaacca gcaccatttg gcgttggacc tcagcctggt    420
ggagcacttc ccggtttcgg ccaagtaagc ggcgcgcaaa gtgccctgat ctccagaata    480
gcaaacgcat tgggaaatac agcaacaatg agagcggttc ttagaagcgg tgtttcccaa    540
cagattgtct cgaacgtagt acaaggagcc gttcaagcat tgtctagttc tctcggcatc    600
gacggaaata acttggcaag aatagcgtca caaacaatcc ttagagttcc cgcaggttca    660
gacacttctg catatgctca agcattctct actgctttgt tcaattctgg agttctgaat    720
gcaagtaacg ttaatacatt gggatcacaa gtcgtgtcaa cacttttaag aggaatatca    780
agtacggcac aaggccttgg cttaaacgta gacgctggaa gtgtacagag cgacattagt    840
```

```
tctagcagca gcttcctatc cacaagctct tcatcgacta gttcctctca gacaactgct    900
gcttcgacat ctggattcac aggagcctca taccccggac ctcaagtctc acaaccagca    960
ccatttggcg ttggacctca gcctggtgga gcacttcccg gtttcggcca agtaagcggc   1020
gcgcaaagtg ccctgatctc cagaatagca acgcattgg gaaatacagc acaatgaga    1080
gcggttctta gaagcggtgt tcccaacag attgtctcga acgtagtaca aggagccgtt   1140
caagcattgt ctagttctct cggcatcgac ggaaataact tggcaagaat agcgtcacaa   1200
acaatcctta gagttcccgc aggttcagac acttctgcat acgctcaagc attctctact   1260
gctttgttca attctggagt tctgaatgca agtaacgtta atacattggg atcacaagtc   1320
gtgtcaacac ttttgagagg aatatcaaat acggcacaag gccttggctt aaacgtagac   1380
gctggaagtg tacagagcga cattagttct agcagcagct tcctatccac aagctcttca   1440
tcgactagtt cctctcagac aactgctgct tcgacatctg gattcgcaag agcatacact   1500
ggacctcaaa tctcacaacc tgcacctttg ggcgttggac ctcaggtctc acaacctcga   1560
cctttaggcg ttgctcctca gacttctggg gcaaggcctt tggtggagt aactgggccg   1620
tcggctggaa tttctttagg atctgccctt aattcaccga ttggactgag atctggtttg   1680
gcagcagcta gaattagcca actgacatca tctctaggga tgccatcac cccctatggc   1740
gttgatgcta atgctcttgc cagcagtcta caagcaagtt tctcaactct tcaaagttcc   1800
ggtatgtctg caagcgatgc taaaatcgaa gttttgttag aaactatagt aggactgctt   1860
caactcttga gcaacactca gattcgtgga gtgaacatgg ctacggcgtc ttctgtggcg   1920
agttctgctg ccaaatcatt tgaattagtt ttatcttaaa gtttttgatc tttttttcagt   1980
cgcgtaaaat tttatttttcc gatatgtaaa ttacagatga aatttttgtt caagcacaat   2040
aaaaagcatt ttttcaacgc aaaaaaaaaa aaaaaaaaaa aaaaaaaaa           2090

<210> SEQ ID NO 15
<211> LENGTH: 1479
<212> TYPE: DNA
<213> ORGANISM: Parawixia bistriata

<400> SEQUENCE: 15
aggagcccca ggcggagcag gaggtggtgt tggaccagga ggcggtgctg gtggaacctc     60
tggaggtgct agcggatcag gtccagtatc tgtctctact gctgtaaatg tcggcggtgc    120
tggcggacca ggtgcaggtg gaccaggagc tggtggcgtc ggaccgggtg ttgtaggccc    180
tggaggactt ggaggtcccg gtggattcgg tggaccaggc ggtcctggag gaccaggcgg    240
ccctggggca ccaggcggcg ctggaggaat gttcggtcct ggaggtgctg gaggcatgta    300
cggacctgga ggtgctggag gcatgtacgg acctggtggt gctggacgag gtccaggagg    360
agctggtgca cctggagctc cgggaggacc aggaggtccc ggaggaccag gaggattcgg    420
aggtggagca ggagctggtg gtatggttcc tggtggagcc tctagaggtc ctggcggatc    480
aggcccagta acagttacag agacagttac agttggagga gccggaggac caggacctgg    540
tggaatcggt ggatcgtcag gtcctggagc aggcggtgca ccaggtggat tcggtggtcc    600
tggaggtcct ggtggacctg gagacccgg aggtccaggt ggtgcagccg gaggaccagg    660
agctggtggt gcaggtcctg gaggatctgg tccggcaact gtttcttctt ctgtaactgt    720
tgttggcgct ggaggacccg gtgaccaggg agctggtgga atcgttccag gaggtattta    780
cggtccagga ggagctggtg gtgtcgtacc ggcggtatt tacggtccag gaggagtacc    840
tagtggacca ggaggtccag gtggacctgt tggtccaggt ggttacggag ctcctggtgg    900
```

```
attaggtgtt ggtatttac ctgggactgc tagtgctgga acttctggcc caacaactgt      960
cacagaagtt gtttccatta atgttagtgg tggtcaatca tcaagtggtg tccgacccgg     1020
aaatagctac actcctgcag ctggaggatc cgcaagatta ccttctctta ttaacggtgt     1080
catgagttct atgcaaggag gtggatttaa ttaccagaat ttcggcaatg ttctctcgca     1140
gtttgctact ggatccggaa cttgcaatag caatgatata aatctgttaa tggatgctct     1200
ttttgcggct ctccataccc taagctatca aggacagtcc tctgttccaa catatccttc     1260
gcccgctgca atgtcctctt attcgcaatc tgttcgaggg tgctttggat attaattgag     1320
tttttatgat gtttgaatag tctcaaattc ttattatgca ttgtttgaaa ataagttttt     1380
tgtaaatgtt ttgtttttaa gttctcataa aactaattaa taagataata aattattatt     1440
gtgcaagcaa aaaaaaaaaa aaaaaaaaaa aaaaaaaaa                            1479

<210> SEQ ID NO 16
<211> LENGTH: 1709
<212> TYPE: DNA
<213> ORGANISM: Parawixia bistriata

<400> SEQUENCE: 16
ggaggatacg gcgcaggagc tggtgccggt gcaggtgcag ccgctgctgc tgctgctgga      60
gctggtgctg gaggcggata tggtggagga tacggcgcag gaggtggtgc cggtgcaggt     120
gctggagcag gtgcaggtgc aggtgctgga gcaggagccg gacgtggagg tgccggtgga     180
tatggcgctg gagctggtgc cggtgcaggt gcagcagctg ccgccgctgc tggagctggt     240
gctggaggcg gatatggtgg aggatacggt gcaggagttg gtgccggtgc aggagccgga     300
gctggtgctg gaggcggata tggtggagga tacggcgcag gagctggtgc cggtgcaggt     360
gcagccgctg ctgccgctgc tggagctggt gctggaggcg gatatggtgg aggatacggc     420
gcaggaggtg gtgccggtgc aggtgctgga gcaggtgcag gtgcaggtgc tggagcagga     480
gccggacgag gaggtgccgt tggatatgga gctggtgccg gtgcaggtgc agcagctgcc     540
gccgctgctg agctggtgcc tggaggtgga tatggtggag gatatggtgc aggaggtggt     600
gccggtgcag gagccggagc tggtgctgga ggcggatatg gtggaggata cggcgcagga     660
ggtggtgccg gtgcaggtgc aggtgctgga gcaggagccg gacgaggagg tgccggtgga     720
tatgcgctg gagccggtgc cgctgcaggt gcagcagctg ccgccgctgc tggagctggt     780
gctggaggcg gatatggtgg aggatacggt gcaggaggtg gtgctggtgc aggtgctggt     840
gcagcggctg gcgccggagc tggagctgga cgaggaggtc cggtggata tggcgctgga     900
gctggtgccg gtgcaggtgc agctgctgct gctggagctg gtgctggagg cggatatggt     960
ggaggataca gcgcaggagg tggtgctggt gctggttcag gtgctgcggc aggagccgga    1020
gctggacgag gaggtgccgg tggatatagc gctggagctg gtaccggtgc aggtgcagct    1080
gctggagctg gtacagcagg cggatatagt ggaggatacg tgccggagc ttcttcaagt     1140
gctggaagca gtttcatttc ttcaagttcg atgagctcat ctcaagcaac tggatacagt    1200
tcctcaagtg gatatggagg tggagctgcg agtgctgccg ctggtgcagg agctgctgca    1260
ggcggatatg gtggaggtta cggagcagga gctggtgctg gtgcagccgc tgcttcaggt    1320
gccactggca gagtagcaaa tagtcttgga gcaatggctt ctggtggaat taatgccta     1380
cctggtgtat tttcaaacat cttctcacaa gtaagtgctg cttcgggtgg tgcctctggt    1440
ggtgcagttc tagttcaggc tttgacagag gttattgcct tgcttcttca tatattaagc    1500
```

-continued

| | |
|---|---|
| agtgcctcta tcggtaatgt tagttcacaa ggattagaag gctcaatggc tattgctcaa | 1560 |
| caggccatag gagcttacgc tggttgagtc agatgacagt ctctctcatt taaaagtata | 1620 |
| acttttgtct actagcttct atgtctatga ttgtatttaa tacaagcaaa taaatttagc | 1680 |
| attctgaaaa aaaaaaaaaa aaaaaaaaa | 1709 |

<210> SEQ ID NO 17
<211> LENGTH: 1754
<212> TYPE: DNA
<213> ORGANISM: Parawixia bistriata

<400> SEQUENCE: 17

| | |
|---|---|
| gccgccacag catcagcagc tggtggactt ggaggacagg gaggacttgg tggattaggt | 60 |
| tcacaaggag ctggtctagg aggatacgga caaggaggag ccggtcaagg tggtgccgcc | 120 |
| gccgcagcag cagcagctgg tggacttgga ggacaaggcg gacgaggtgg attaggttca | 180 |
| caaggagctg gccaaggagg atatggacaa ggaggagccg gtcaaggtgg tgccgccgcc | 240 |
| gcagcagcag cagctggtgg acttggagga caaggaggac ttggtgcatt aggttcacaa | 300 |
| ggagctggtc aaggaggagc tggccaagga ggatacggac aaggaggagc cgcagcagca | 360 |
| gcagctggtg gacttggagg acaaggagga cttggtggat taggttcaca aggagctgga | 420 |
| caaggaggat acggacaagg aggagccggt caaggtggtg ccgccgccgc cgcagcagca | 480 |
| gctggtggac ttggaggaca gggaggactt ggtggattag gttcacaagg agctggtcca | 540 |
| ggaggatacg gacaaggagg agccggtcaa ggtggtgccg ccgccgcagc agcagcagct | 600 |
| ggtggacttg gaggacaagg aggacttggt gcattaggtt cacaaggagc tggtcaagga | 660 |
| ggatacggac aaggaggagc tggtcaaggt ggtgccgccg ccgcagcagc tgctggtgga | 720 |
| cttggaggac aaggaggact tggtgcatta ggttcacaag gagctggcca aggaggatat | 780 |
| ggacaaggag gttcacaagg agctggccaa ggaggatacg gacaaggagg agccgccgct | 840 |
| gccgcagcag cagctggtgg acttggaggc caaggaggac taggtggatt aggttcacaa | 900 |
| ggagctggcc aaggaggata tggacaagga ggttcacaag gagctggcca aggaggagcc | 960 |
| gccgccgcag cagcagcagc tggtggactt ggaggacaag gaggatttgg tggattaggt | 1020 |
| tcacaaggag ctggtcaagg aggatacgga caaggaggag ccggtcaagg tggtgccgcc | 1080 |
| gccgcagcag cagcagctgg tgtacttgga ggacaaggag gacttggtgg attaggttca | 1140 |
| caaggagctg gtcaaggtgg atacggacaa ggaggagctg gtcaaggtgg tgccgccgcc | 1200 |
| gccgcagcag cagcagcagc tggtggactt ggaggacaag gaggacgagg tggattaggt | 1260 |
| tcacaaggag ctggccaagg gggatacgga caaggaggag ctggtgcctc atccgctgct | 1320 |
| gctgcgtctg ctgctgcttc tcgtctgtca tccgcaagtg ctgcttctag ggtctcgtct | 1380 |
| gccgtttcat ctttagtatc aagtggtgga ccaactaatt ctgcagcatt gtcgagtacc | 1440 |
| attagcaatg ttgtatctca agttagcgca agcaaccctg gtctttctgg ttgtgatgtt | 1500 |
| ctcgtccagg cgctacttga aatcgtttca gcattggttc atattcttgg atcctctagt | 1560 |
| attggtcaag ttaactataa tgccgctggt caatcagcgt cagttgtcgg acagtctttt | 1620 |
| taccaagctc ttgcttaaga aagtcatgtg aacccttctg aatttctttt tctttttaata | 1680 |
| gtcttgtttt gtatatgttc tttaaaataa attttttgcat gattgaaaaa caaaaaaaaaa | 1740 |
| aaaaaaaaaa aaaa | 1754 |

<210> SEQ ID NO 18
<211> LENGTH: 1481

```
<212> TYPE: DNA
<213> ORGANISM: Parawixia bistriata
<220> FEATURE:
<221> NAME/KEY: modified_base
<222> LOCATION: (1364)..(1364)
<223> OTHER INFORMATION: a, c, t, g, unknown or other
<220> FEATURE:
<221> NAME/KEY: modified_base
<222> LOCATION: (1428)..(1428)
<223> OTHER INFORMATION: a, c, t, g, unknown or other
<220> FEATURE:
<221> NAME/KEY: modified_base
<222> LOCATION: (1430)..(1430)
<223> OTHER INFORMATION: a, c, t, g, unknown or other
<220> FEATURE:
<221> NAME/KEY: modified_base
<222> LOCATION: (1435)..(1438)
<223> OTHER INFORMATION: a, c, t, g, unknown or other
<220> FEATURE:
<221> NAME/KEY: modified_base
<222> LOCATION: (1440)..(1445)
<223> OTHER INFORMATION: a, c, t, g, unknown or other
<220> FEATURE:
<221> NAME/KEY: modified_base
<222> LOCATION: (1450)..(1453)
<223> OTHER INFORMATION: a, c, t, g, unknown or other
<220> FEATURE:
<221> NAME/KEY: modified_base
<222> LOCATION: (1456)..(1466)
<223> OTHER INFORMATION: a, c, t, g, unknown or other
<220> FEATURE:
<221> NAME/KEY: modified_base
<222> LOCATION: (1470)..(1470)
<223> OTHER INFORMATION: a, c, t, g, unknown or other
<220> FEATURE:
<221> NAME/KEY: modified_base
<222> LOCATION: (1473)..(1481)
<223> OTHER INFORMATION: a, c, t, g, unknown or other

<400> SEQUENCE: 18
caaggaccag gagcaggtca acaaggacca ggagcaggtc aacaaggacc atatggacca      60
agtgccgccg ccgcagcagc tgccgctgga ggttatggac caggaggtgc aggacaacaa    120
ggaccaggag caggtcaaca aggaccaggt agtcaaggac aatctggacc tggtgctacc    180
gtcgccgcag ctgccgctgg aggttatgga ccaggagggg caggacaaca aggaccagga    240
gcaggtcaac aaggtcaagg tagccaagga ccatatggac cagctgccac cgccgccgca    300
gccgccgctg gaggttatgg accaggatct ggacaacagg gaccaggagc aggtcaacaa    360
ggaccaggag gtcaaggacc atatggacca agtgccgccg ccgcagcagc tgccgctgga    420
ggttatggac caggatctgg acaacaagga ccaggagcag gtccacaagg cccaggtagt    480
caaggacctt atggaccagg tgccgccgca gcagcagccg ccgttggagg ttatggacca    540
ggatctggac aacaaggacc aggagcaggt caacaaggac caggaggtca aggaccatat    600
ggaccaagtt ccgccgccgc agcagctgcc gctggaggtt atggaccagg aggtgcagga    660
caacaagtac caggagcagg tcaacaaggt ccaggtaacc aaggaccatc tggaccaggt    720
gccgccgccg cagcagctgc cgctggaggt tatggaccag gaggtgcagg acaacaagga    780
ccagcagcag gtcaacaagg tccaggtagt caaggatcat atggaccagg tgccgccgct    840
gcagcagctg ctgctggagg ttatggacca ggatctggac aacaaggacc aggaggagct    900
ggtcaacaag gacctggagg tcaaggacct tatggacctg ctcttcttc agcagcagcc    960 gtcggaggtt atggaccaag ttctggatta caaggaccag caggtcaagg gccttatgga   1020
cctggtgcag ctgcttccgc agcagcagcc gctgggggctt ctcgcctttc ttctccacag   1080
gccagttcca gagtttcatc tgctgtatct tctttggtat caagcggtcc tacgaattcc   1140
```

```
gctgcactta ccaataccat tagtagcgtt gtatcacaaa ttagtgcaag taatccaggt      1200
ctctctggtt gcgatgtact tatacaagcg ttattggaaa ttgtatctgc ccttgtacac      1260
attcttggat attctagtat cggccaaatc aactatgatg ctgccgcaca gtatgcgtca      1320
ttggttggtc agtctgtagc tcaagccctt gcttgatgca ttancactgg atttgcaatt      1380
ttttgttaaa ttactttaat ataatttttaa attttctcaa taaactgnan cattnnnngn     1440
nnnnnaaaan nnnaannnnn nnnnnnaaan aannnnnnnn n                          1481
```

<210> SEQ ID NO 19
<211> LENGTH: 807
<212> TYPE: DNA
<213> ORGANISM: Parawixia bitriata

<400> SEQUENCE: 19

```
ggtggtgcca atggcgcttc cgctgcagca gcttcagctg gaggtgcagg aggatatgga       60
agtgatggag gatatggtca aggtggacaa ggagctggag gcgatggctc tgctgccgcc      120
gcagccgcag cagcatccgg tggacgaggt ggacaaggcg gatttggttc tcaaggagca      180
ggtggtagag gtctaggagg atctgcacga ggtggtgctg gtggtacttc cgctgcagct      240
gcatcagctg gtggtgcaag aggatatgga ggtgacggag gatatggtca aggtggatct      300
ggacgaggtg gtgctggtag tgcttccgca gcagcggctt cagctggagg tgcaggagga      360
tatggaggtg acggaggata tggtgaaggt ggacaaggag caggaggcga tggagtcgca      420
acttcttctg ctgcttcccg tctgtcatct ccctcttcta tacgaagaat atcggaagtt      480
gtatctacat tctcagatga tgactttgga aattcagctc ttttttcaaa tgtttataac      540
agtgtggctt ctggaattac atcatccaat cctggtctct ctggatgcga tgttcaaatt      600
caaacgttac ttgaaatgaa ttcggcattg cttgctttac tttatggatt tgatgcttat      660
tcgtcggctg ctttagtaaa cgatttcgtt aatcaacctc attaatgagc gatataactt      720
ttctttttaa aattttttcaa ttgtaatatg taaatcttac taaataaaat tatgcaatga     780
taaaaaaraa aaaaaaaaa aaaaaaa                                            807
```

<210> SEQ ID NO 20
<211> LENGTH: 1037
<212> TYPE: PRT
<213> ORGANISM: Nephilengys cruentata

<400> SEQUENCE: 20

```
Ala Gly Gly Ser Gly Gly Thr Thr Val Ile Glu Asp Leu Asp Ile Thr
 1               5                  10                  15

Val Asn Gly Pro Gly Gly Pro Ile Thr Ile Ser Glu Glu Leu Thr Ile
            20                  25                  30

Gly Gly Pro Gly Ala Gly Gly Ser Gly Pro Gly Gly Ala Gly Pro Gly
        35                  40                  45

Gly Ala Gly Pro Gly Gly Ala Gly Pro Gly Gly Ala Gly Pro Gly Gly
    50                  55                  60

Ala Gly Pro Gly Gly Val Gly Pro Gly Gly Ala Gly Pro Gly Gly
65                  70                  75                  80

Ala Gly Gly Pro Phe Gly Pro Gly Gly Ser Pro Gly Gly Ala Gly
                85                  90                  95

Gly Ala Gly Gly Pro Tyr Gly Pro Gly Gly Ala Tyr Gly Pro Gly Gly
            100                 105                 110

Pro Gly Gly Pro Gly Gly Pro Gly Gly Pro Gly Ser Gly Gly Pro Tyr
        115                 120                 125
```

```
Gly Pro Gly Gly Ala Tyr Gly Pro Gly Gly Ala Tyr Gly Pro Gly Gly
    130                 135                 140
Ala Tyr Gly Pro Gly Gly Ala Gly Gly Pro Gly Gly Ala Gly Gly Pro
145                 150                 155                 160
Tyr Gly Pro Gly Gly Pro Tyr Gly Pro Gly Gly Pro Tyr Gly Pro Gly
                165                 170                 175
Gly Ala Gly Gly Pro Gly Gly Ala Gly Pro Tyr Gly Pro Gly Gly
            180                 185                 190
Ala Gly Pro Gly Gly Tyr Gly Pro Gly Gly Ala Gly Pro Gly Gly Tyr
            195                 200                 205
Gly Pro Gly Gly Ser Gly Pro Gly Gly Ala Gly Pro Gly Gly Tyr Gly
    210                 215                 220
Pro Gly Gly Ser Gly Pro Gly Gly Ala Gly Pro Gly Gly Tyr Gly Pro
225                 230                 235                 240
Gly Gly Ala Gly Pro Gly Gly Tyr Gly Pro Gly Gly Ala Gly Pro Gly
                245                 250                 255
Gly Ala Gly Pro Gly Gly Ala Gly Pro Gly Gly Tyr Gly Pro Gly Gly
            260                 265                 270
Ser Gly Pro Gly Gly Pro Gly Ser Gly Gly Pro Gly Gly Ala Gly Gly
    275                 280                 285
Ser Gly Gly Thr Thr Val Ile Glu Asp Leu Asp Ile Thr Val Asn Gly
    290                 295                 300
Pro Gly Gly Pro Ile Thr Ile Ser Glu Glu Leu Thr Val Gly Gly Pro
305                 310                 315                 320
Gly Ala Gly Gly Ser Gly Pro Gly Gly Ala Gly Pro Gly Gly Ala Gly
                325                 330                 335
Pro Gly Gly Ala Gly Pro Gly Gly Val Gly Pro Gly Gly Ala Gly Gly
            340                 345                 350
Pro Gly Gly Ala Gly Gly Pro Phe Gly Pro Gly Gly Ser Gly Pro Gly
            355                 360                 365
Gly Ala Gly Gly Ala Gly Gly Pro Tyr Gly Pro Gly Gly Ala Tyr Gly
            370                 375                 380
Pro Gly Gly Pro Gly Gly Pro Gly Gly Pro Gly Gly Pro Gly Ser Gly
385                 390                 395                 400
Gly Pro Tyr Gly Pro Gly Gly Ala Tyr Gly Pro Gly Gly Ala Tyr Gly
                405                 410                 415
Pro Gly Gly Ala Tyr Gly Pro Gly Gly Ala Gly Gly Pro Tyr Gly Pro
            420                 425                 430
Gly Gly Pro Tyr Gly Pro Gly Gly Pro Tyr Gly Pro Gly Gly Ala Gly
            435                 440                 445
Gly Pro Gly Gly Ala Gly Pro Gly Pro Tyr Gly Pro Gly Gly Ala Gly Pro
    450                 455                 460
Gly Gly Tyr Gly Pro Gly Gly Ala Gly Pro Gly Gly Tyr Gly Pro Gly
465                 470                 475                 480
Gly Ser Gly Pro Gly Gly Ala Gly Pro Gly Gly Tyr Gly Pro Gly Gly
                485                 490                 495
Ser Gly Pro Gly Gly Ala Gly Pro Gly Gly Tyr Gly Pro Gly Gly Ala
            500                 505                 510
Gly Pro Gly Gly Tyr Gly Pro Gly Gly Ala Gly Pro Gly Gly Ala Gly
            515                 520                 525
Pro Gly Gly Ala Gly Pro Gly Gly Tyr Gly Pro Gly Gly Ser Gly Pro
            530                 535                 540
```

```
Gly Gly Pro Gly Ser Gly Gly Pro Gly Gly Ala Gly Gly Ser Gly Gly
545                 550                 555                 560
Thr Thr Val Ile Glu Asp Leu Asp Ile Thr Val Asn Gly Pro Gly Gly
            565                 570                 575
Pro Ile Thr Ile Ser Glu Glu Leu Thr Val Gly Gly Pro Gly Ala Gly
                580                 585                 590
Gly Ser Gly Pro Gly Gly Ala Gly Pro Gly Gly Ala Gly Pro Gly Gly
        595                 600                 605
Ala Gly Pro Gly Gly Ala Gly Pro Gly Gly Ala Gly Pro Gly Gly Val
    610                 615                 620
Gly Pro Gly Gly Ala Gly Pro Gly Gly Ala Gly Pro Gly Gly Phe Gly
625                 630                 635                 640
Pro Gly Gly Ser Gly Pro Gly Gly Ala Gly Ala Gly Gly Pro Gly Tyr
            645                 650                 655
Gly Pro Gly Gly Ala Tyr Gly Pro Gly Gly Pro Gly Gly Pro Gly Gly
            660                 665                 670
Pro Gly Gly Pro Gly Gly Pro Gly Ser Gly Gly Pro Tyr Gly Pro Gly
            675                 680                 685
Gly Ala Tyr Gly Pro Gly Gly Ala Tyr Gly Pro Gly Gly Ala Tyr Gly
    690                 695                 700
Pro Gly Gly Ala Gly Gly Pro Gly Gly Ala Ala Gly Pro Tyr Gly Pro
705                 710                 715                 720
Gly Gly Pro Tyr Gly Pro Gly Gly Pro Tyr Gly Pro Gly Gly Ala Gly
            725                 730                 735
Gly Pro Gly Gly Ala Gly Pro Gly Tyr Gly Pro Gly Gly Ala Gly Pro
        740                 745                 750
Gly Gly Tyr Gly Pro Gly Gly Ala Gly Pro Gly Gly Tyr Gly Pro Gly
        755                 760                 765
Gly Ser Gly Pro Gly Gly Ala Gly Pro Gly Gly Tyr Gly Pro Gly Gly
    770                 775                 780
Ser Gly Pro Gly Gly Ala Gly Pro Gly Gly Tyr Gly Pro Gly Gly Ala
785                 790                 795                 800
Gly Pro Gly Gly Tyr Gly Pro Gly Gly Ala Gly Pro Gly Gly Ala Gly
            805                 810                 815
Pro Gly Gly Ala Gly Pro Gly Gly Tyr Gly Pro Gly Gly Ser Gly Pro
            820                 825                 830
Gly Gly Pro Gly Ser Gly Gly Pro Gly Gly Ala Gly Gly Ser Gly Gly
            835                 840                 845
Thr Thr Val Ile Glu Asp Leu Asp Ile Thr Leu Asn Gly Pro Gly Gly
    850                 855                 860
Pro Ile Thr Ile Ser Glu Glu Leu Thr Val Gly Gly Pro Gly Ala Gly
865                 870                 875                 880
Gly Ser Gly Pro Gly Gly Ala Gly Pro Gly Gly Ala Gly Pro Gly Gly
            885                 890                 895
Ala Gly Pro Gly Gly Ala Gly Pro Gly Gly Val Gly Pro Gly Gly Ala
        900                 905                 910
Gly Gly Pro Tyr Gly Ser Gly Gly Phe Gly Phe Gly Gly Ala Gly Gly
        915                 920                 925
Ser Gly Gly Pro Tyr Val Pro Gly Gly Ala Tyr Gly Ala Gly Ser Gly
    930                 935                 940
Thr Pro Ser Tyr Ser Gly Ser Arg Val Pro Asp Leu Val Asn Gly Ile
945                 950                 955                 960
Met Arg Ser Met Gln Gly Ser Gly Phe Asn Tyr Gln Met Phe Gly Asn
```

```
                    965                 970                 975
Met Leu Ser Lys Tyr Ala Ser Gly Ser Gly Ala Cys Asn Ser Asn Asp
            980                 985                 990

Val Asn Val Leu Met Asp Ala Leu  Leu Ala Ala Leu His  Cys Leu Ser
        995                 1000                1005

Ser His  Gly Ser Pro Ser Phe  Gly Ser Ser Pro Thr  Pro Ser Ala
        1010                1015                1020

Met Asn  Ala Tyr Ser Asn Ser  Val Arg Arg Met Phe  Gln Phe
        1025                1030                1035

<210> SEQ ID NO 21
<211> LENGTH: 461
<212> TYPE: PRT
<213> ORGANISM: Nephilengys cruentata

<400> SEQUENCE: 21

Ala Ser Gln Ser Ala Ser Ser Ser Ala Ser Ala Ser Ala Phe Ala
1               5                   10                  15

Gln Gln Ser Ser Ala Ser Leu Ala Ala Ser Ser Ser Phe Ser Gln Ala
                20                  25                  30

Phe Ala Ser Ala Ala Ser Ala Ser Ala Val Gly Asn Val Ala Tyr Gln
            35                  40                  45

Leu Gly Leu Ser Ala Ala Gln Ser Leu Gly Ile Ala Asn Ala Gly Ala
50                  55                  60

Leu Ala Ser Ala Leu Ala Gln Ser Val Ser Val Gly Val Gly Ala
65                  70                  75                  80

Ser Ser Ser Ala Tyr Ala Asn Ala Val Ala Gly Ala Val Gly Gln Phe
                85                  90                  95

Leu Ala Asn Gln Gly Ile Leu Asn Thr Gly Asn Ala Ser Ser Leu Ala
                100                 105                 110

Ser Ser Phe Ser Ser Ala Leu Ser Ala Ser Ala Ala Ala Gln Ser
            115                 120                 125

Gln Ser Phe Ala Gln Ser Gln Ala Ala Ala Ser Ala Phe Gln Gln Ala
            130                 135                 140

Ala Ser Gln Ser Ala Ser Gln Ser Ala Ala Gln Ser Gly Ser Gln Ser
145                 150                 155                 160

Ser Ser Thr Thr Thr Thr Thr Ser Ala Ser Gly Ser Gln Ser Ala Ser
                165                 170                 175

Gln Ser Ala Ser Ser Ser Ser Ala Ser Ala Ser Ala Phe Ala Gln Gln
            180                 185                 190

Ser Ser Ala Ser Leu Ala Ala Ser Ser Phe Ser Gln Ala Phe Ala
            195                 200                 205

Ser Ala Ala Ser Ala Ser Ala Val Gly Asn Val Ala Tyr Gln Leu Gly
        210                 215                 220

Leu Ser Ala Ala Gln Ser Leu Gly Ile Ala Asn Ala Gly Ala Leu Ala
225                 230                 235                 240

Ser Ala Leu Ala Gln Ser Val Ser Val Gly Val Gly Ala Ser Ser
                245                 250                 255

Ser Ala Tyr Ala Asn Ala Val Ala Gly Ala Val Gly Gln Phe Leu Ala
            260                 265                 270

Asn Gln Gly Ile Leu Asn Thr Gly Asn Ala Ser Ser Leu Ala Ser Ser
                275                 280                 285

Phe Ser Asn Ala Leu Ser Ser Ser Ala Ala Asn Ser Val Gly Ser Gly
            290                 295                 300
```

Leu Leu Leu Gly Pro Ser Gln Tyr Val Gly Ser Ile Ala Pro Ser Ile
305                 310                 315                 320

Gly Gly Ala Ala Gly Ile Ser Ile Ala Gly Pro Gly Ile Leu Ser Tyr
            325                 330                 335

Leu Pro Pro Val Ser Pro Leu Asn Ala Gln Ile Ile Ser Ser Gly Leu
                340                 345                 350

Leu Ala Ser Leu Ala Pro Val Leu Ser Ser Ser Gly Leu Ala Ser Ser
            355                 360                 365

Ser Ala Thr Ser Arg Val Gly Ser Leu Ala Gln Ser Leu Ala Ser Ala
        370                 375                 380

Leu Gln Ser Ser Gly Gly Thr Leu Asp Val Ser Thr Phe Leu Asn Leu
385                 390                 395                 400

Leu Ser Pro Ile Ser Thr Gln Ile Gln Ala Asn Thr Ser Leu Asn Ala
                405                 410                 415

Ser Gln Ala Ile Val Gln Val Leu Leu Glu Ala Val Ala Ala Leu Leu
            420                 425                 430

Gln Ile Ile Asn Gly Ala Gln Ile Thr Ser Val Asn Phe Gly Ser Val
        435                 440                 445

Ser Ser Val Asn Thr Ala Leu Ala Thr Ala Leu Ala Gly
    450                 455                 460

<210> SEQ ID NO 22
<211> LENGTH: 505
<212> TYPE: PRT
<213> ORGANISM: Nephilengys cruentata

<400> SEQUENCE: 22

Gln Gly Ala Gly Ala Ala Ala Ala Ala Ala Gly Gly Ala Gly
1               5                   10                  15

Gln Gly Gly Tyr Gly Gly Leu Gly Gly Gln Gly Ala Gly Ala Ala Ala
                20                  25                  30

Ala Ala Ala Gly Gly Ala Gly Gln Gly Gly Tyr Gly Gly Gln Gly Ala
            35                  40                  45

Gly Gln Gly Ala Ala Ala Ala Ala Ser Gly Ala Gly Gln Gly Gly
    50                  55                  60

Tyr Glu Gly Pro Gly Ala Gly Gln Gly Ala Gly Ala Ala Ala Ala Ala
65                  70                  75                  80

Ala Gly Gly Ala Gly Gln Gly Gly Tyr Gly Gly Leu Gly Gly Gln Gly
                85                  90                  95

Ala Gly Gln Gly Ala Gly Ala Ala Ala Ala Gly Gly Ala Gly
            100                 105                 110

Gln Gly Gly Tyr Gly Gly Leu Gly Gly Gln Gly Ala Gly Gln Gly Ala
                115                 120                 125

Gly Ala Ala Ala Ala Ala Gly Gly Ala Gly Gly Gly Tyr Gly
            130                 135                 140

Gly Gln Gly Ala Gly Gln Gly Ala Ala Ala Ala Ala Gly Gly Ala
145                 150                 155                 160

Gly Gln Gly Gly Tyr Gly Gly Leu Gly Ser Gly Gln Gly Gly Tyr Gly
                165                 170                 175

Arg Gln Gly Ala Gly Ala Ala Ala Ala Ala Ala Gly Gly Ala
            180                 185                 190

Gly Gln Gly Gly Tyr Gly Gly Leu Gly Gly Gln Gly Ala Gly Ala Ala
                195                 200                 205

Ala Ala Ala Ala Gly Gly Ala Gly Gln Gly Gly Tyr Gly Gly Gln Gly
            210                 215                 220

```
Ala Gly Gln Gly Ala Ala Ala Ala Ser Gly Ala Gly Gln Gly
225                 230                 235                 240

Gly Tyr Gly Gly Pro Gly Ala Gly Gln Gly Ala Gly Ala Ala Ala Ala
                245                 250                 255

Ala Ala Gly Gly Ala Gly Gln Gly Gly Tyr Gly Gly Leu Gly Gly Gln
            260                 265                 270

Gly Ala Gly Gln Gly Ala Gly Ala Ala Ala Ala Ala Gly Gly Ala
        275                 280                 285

Gly Gln Gly Gly Tyr Gly Gly Gln Gly Ala Gly Gln Gly Ala Ala Ala
        290                 295                 300

Ala Ala Ala Gly Gly Ala Gly Gln Gly Gly Tyr Gly Gly Leu Gly Ser
305                 310                 315                 320

Gly Gln Gly Gly Tyr Gly Gly Gln Gly Ala Gly Ala Ala Ala Ala
            325                 330                 335

Gly Gly Ala Gly Gln Gly Gly Tyr Gly Gly Leu Gly Gly Gln Gly Ala
            340                 345                 350

Gly Gln Gly Ala Gly Ala Ala Ala Ala Gly Gly Ser Gly Arg
        355                 360                 365

Gly Gly Tyr Gly Ser Gln Gly Ala Gly Gln Gly Ala Ala Ala Ala
370                 375                 380

Ala Gly Gly Ala Gly Gln Gly Gly Tyr Gly Gly Ala Gly Ser Gly Ala
385                 390                 395                 400

Ala Ala Ala Ser Ala Ala Ala Ser Arg Leu Ser Ser Pro Glu Ala Ser
            405                 410                 415

Ser Arg Val Ser Ser Ala Val Ser Asn Leu Val Ser Ser Gly Pro Thr
            420                 425                 430

Asn Ser Ala Ala Leu Ser Asn Thr Ile Ser Ser Val Val Ser Gln Ile
            435                 440                 445

Ser Ala Ser Asn Pro Gly Leu Ser Gly Cys Asp Val Leu Val Gln Ala
        450                 455                 460

Leu Leu Glu Val Val Ser Ala Leu Ile His Ile Leu Gly Ser Ser Ser
465                 470                 475                 480

Ile Gly Pro Val Asn Tyr Gly Ser Ala Ser Gln Ser Thr Gln Ile Val
            485                 490                 495

Gly Gln Ser Val Tyr Gln Ala Leu Gly
            500                 505

<210> SEQ ID NO 23
<211> LENGTH: 1119
<212> TYPE: PRT
<213> ORGANISM: Nephilengys cruentata

<400> SEQUENCE: 23

Ala Gly Gly Ala Gly Gly Tyr Gly Val Gly Gln Gly Tyr Gly Ala Gly
1               5                   10                  15

Ala Gly Ala Gly Ala Ala Gly Ala Gly Ala Gly Gly Ala Gly Gly
            20                  25                  30

Tyr Gly Ala Gly Gln Gly Tyr Gly Ala Gly Ala Gly Val Gly Ala Ala
        35                  40                  45

Ala Ala Ala Gly Ala Gly Gly Val Gly Gly Gly Gly Tyr Gly
        50                  55                  60

Arg Gly Ala Gly Ala Gly Ala Gly Ala Gly Ala Ala Ala Gly
65                  70                  75                  80

Ala Gly Ala Gly Ala Ala Ala Gly Ala Gly Ala Gly Gly Ala Gly Gly
```

```
                      85                  90                  95
Tyr Gly Ala Gly Gln Gly Tyr Gly Ala Gly Ala Gly Val Gly Ala Ala
                     100                 105                 110

Ala Ala Ala Gly Ala Gly Ala Gly Val Gly Gly Ala Gly Gly Tyr Gly
                     115                 120                 125

Arg Gly Ala Gly Ala Gly Ala Gly Ala Gly Ala Gly Ala Gly Ala Gly
                     130                 135                 140

Tyr Gly Arg Gly Ala Gly Ala Gly Ala Gly Ala Gly Ala Gly Ala Gly
145                 150                 155                 160

Gly Ala Gly Gly Tyr Gly Ala Gly Gln Gly Tyr Gly Ala Gly Ala Gly
                     165                 170                 175

Ala Gly Ala Ala Ala Ala Ala Gly Ala Gly Ala Gly Ala Gly Gly Ala
                     180                 185                 190

Gly Gly Tyr Gly Arg Gly Ala Gly Ala Gly Ala Gly Ala Gly Ala Gly
                     195                 200                 205

Ala Gly Gly Ala Gly Gly Tyr Gly Ala Gly Gln Gly Tyr Gly Ala Gly
                     210                 215                 220

Ala Gly Ala Gly Ala Ala Ala Ala Ala Gly Ala Gly Ala Gly Ala Gly
225                 230                 235                 240

Gly Ala Gly Gly Tyr Gly Arg Gly Ala Gly Ala Gly Ala Gly Ala Gly
                     245                 250                 255

Ala Gly Ala Gly Gly Ala Gly Gly Tyr Gly Ala Gly Gln Gly Tyr Gly
                     260                 265                 270

Ala Gly Ala Gly Ala Gly Ala Ala Ala Ala Ala Gly Ala Gly Ala Gly
                     275                 280                 285

Ala Gly Gly Ala Gly Gly Tyr Gly Arg Gly Ala Gly Ala Gly Ala Gly
                     290                 295                 300

Ala Gly Ala Gly Ala Gly Ala Gly Gly Tyr Gly Arg Gly Ala Gly Ala
305                 310                 315                 320

Gly Ala Gly Ala Gly Ala Ala Gly Ala Gly Ala Gly Ala Gly Gly Ala
                     325                 330                 335

Gly Arg Tyr Gly Ala Gly Gln Gly Tyr Gly Ala Gly Ala Gly Ala Gly
                     340                 345                 350

Ala Ala Ala Gly Ala Gly Ala Gly Gly Ala Gly Gly Tyr Gly Ala Gly
                     355                 360                 365

Gln Gly Tyr Gly Ala Gly Ala Gly Ala Gly Ala Ala Ala Ala Ala Gly
                     370                 375                 380

Ala Gly Ala Gly Val Gly Gly Ala Gly Gly Tyr Gly Ser Gly Ala Gly
385                 390                 395                 400

Ala Gly Ala Gly Ala Gly Ala Gly Ala Ala Ser Gly Ala Ala Ala Gly
                     405                 410                 415

Ala Ala Ala Gly Ala Gly Ala Gly Gly Ala Gly Gly Tyr Gly Thr Gly
                     420                 425                 430

Gln Gly Tyr Gly Ala Gly Ala Gly Ala Gly Ala Gly Ala Gly Ala Gly
                     435                 440                 445

Gly Ala Gly Gly Tyr Gly Arg Gly Ala Gly Ala Gly Ala Gly Ala Gly
                     450                 455                 460

Ala Gly Gly Ala Gly Gly Tyr Gly Ala Gly Gln Gly Tyr Gly Ala Gly
465                 470                 475                 480

Ala Gly Ala Gly Ala Ala Ala Ala Ala Gly Asp Gly Ala Gly Ala Gly
                     485                 490                 495

Gly Ala Gly Gly Tyr Gly Arg Gly Ala Gly Ala Gly Ala Gly Ala Gly
                     500                 505                 510
```

```
Ala Ala Ala Gly Ala Gly Ala Gly Gly Ala Gly Tyr Gly Ala Gly
            515                 520                 525
Gln Gly Tyr Gly Ala Gly Ala Gly Ala Gly Ala Ala Gly Ala Gly
        530                 535                 540
Ala Gly Gly Ala Gly Gly Tyr Gly Ala Gly Gln Gly Tyr Gly Ala Gly
545                 550                 555                 560
Ala Gly Ala Gly Ala Ala Ala Ala Gly Gly Ala Gly Val Gly
            565                 570                 575
Gly Ala Gly Gly Tyr Gly Arg Gly Ala Gly Ala Gly Ala Ala
        580                 585                 590
Ala Gly Ala Gly Ala Gly Ala Ala Gly Ala Gly Ala Gly Gly Ala
    595                 600                 605
Gly Gly Tyr Gly Thr Gly Gln Gly Tyr Gly Ala Gly Ala Gly Ala Gly
610                 615                 620
Ala Gly Ala Gly Ala Gly Gly Tyr Gly Arg Gly Ala Gly Ala Gly
625                 630                 635                 640
Ala Gly Ala Gly Ala Gly Ala Gly Gly Ala Gly Glu Tyr Gly Ala Gly
            645                 650                 655
Gln Gly Tyr Gly Ala Gly Ala Gly Ala Gly Ala Ala Ala Ala Gly
        660                 665                 670
Ala Gly Ala Gly Ala Gly Gly Ala Gly Gly Tyr Gly Arg Gly Ala Gly
    675                 680                 685
Ala Gly Ala Gly Ala Gly Ala Ala Gly Ala Gly Ala Gly Gly Ala
    690                 695                 700
Gly Gly Tyr Gly Ala Arg Gln Gly Tyr Gly Ala Gly Ala Gly Ala Gly
705                 710                 715                 720
Ala Ala Ala Gly Ala Gly Ala Gly Gly Ala Gly Gly Tyr Gly Ala Gly
            725                 730                 735
Gln Gly Tyr Gly Ala Gly Ala Gly Ala Gly Ala Ala Ala Ala Gly
        740                 745                 750
Ala Gly Ala Gly Ala Gly Gly Ala Gly Gly Tyr Gly Arg Gly Ala Gly
    755                 760                 765
Ala Gly Ala Gly Ala Gly Ala Ala Ala Gly Gln Gly Tyr Gly
    770                 775                 780
Ser Gly Ala Gly Ala Gly Ala Gly Ala Ser Ala Gly Gly Ala Gly Ser
785                 790                 795                 800
Tyr Gly Arg Gly Ala Gly Ala Gly Ala Ala Ala Ala Ser Gly Ala Gly
            805                 810                 815
Ala Gly Gly Tyr Gly Ala Gly Gln Gly Tyr Gly Ala Gly Ala Gly Ala
        820                 825                 830
Val Ala Ser Ala Ala Ala Gly Ala Gly Ser Gly Ala Gly Gly Ala Gly
    835                 840                 845
Gly Tyr Gly Arg Gly Ala Val Ala Gly Ser Gly Ala Gly Ala Gly Ala
    850                 855                 860
Gly Ala Gly Gly Ala Gly Gly Tyr Gly Ala Gly Ala Gly Ala Gly Ala
865                 870                 875                 880
Ala Ala Gly Ala Val Ala Gly Gly Ser Gly Gly Tyr Gly Gly Arg Gln
            885                 890                 895
Gly Gly Tyr Ser Ala Gly Ala Gly Ala Gly Ala Ala Ala Ala Gly
        900                 905                 910
Ala Gly Ala Gly Gly Thr Gly Gly Tyr Gly Arg Gly Ser Gly Ala Gly
    915                 920                 925
```

-continued

Ala Ala Ala Gly Ala Ala Gly Ala Gly Ala Ala Gly Gly Tyr Gly
930                935                940

Gly Tyr Gly Ala Gly Ala Gly Ala Gly Ala Gly Gly Ala Arg Gly Tyr
945                950                955                960

Gly Gly Gly Ala Gly Ala Gly Ala Gly Ala Ala Gly Gly Tyr Gly
965                970                975

Arg Arg Ala Gly Gly Ser Ile Val Gly Thr Gly Ile Ser Ala Ile Ser
980                985                990

Ser Gly Thr Gly Ser Ser Tyr Ser Val Ser Ser Gly Gly Tyr Ala Ser
995                1000                1005

Ala Gly Val Gly Val Gly Ser Thr Val Ala Ser Thr Thr Ser Arg
1010                1015                1020

Leu Ser Ser Ala Gln Ala Ser Ser Arg Ile Ser Ala Ala Ala Ser
1025                1030                1035

Thr Leu Ile Ser Gly Gly Tyr Leu Asn Thr Ser Ala Leu Pro Ser
1040                1045                1050

Val Ile Ser Asp Leu Phe Ala Gln Val Ser Ala Ser Ser Pro Gly
1055                1060                1065

Val Ser Asp Ser Glu Val Leu Ile Gln Val Leu Leu Glu Ile Val
1070                1075                1080

Ser Ser Leu Ile His Ile Leu Ser Ser Ser Ser Val Gly Gln Val
1085                1090                1095

Asp Phe Asn Ser Val Gly Ser Ser Ala Ala Ala Val Gly Gln Ser
1100                1105                1110

Met Gln Val Val Met Gly
1115

<210> SEQ ID NO 24
<211> LENGTH: 387
<212> TYPE: PRT
<213> ORGANISM: Nephilengys cruentata

<400> SEQUENCE: 24

Gln Gly Tyr Gly Ala Gly Ala Gly Ala Gly Thr Gly Gly Ala
1                5                10                15

Gly Gly Tyr Gly Arg Gly Val Gly Ala Gly Ala Gly Ala Gly
                20                25                30

Ala Gly Gly Ala Gly Gly Tyr Gly Gly Gly Gln Asn Tyr Gly Ala Gly
                35                40                45

Ala Gly Ala Ala Ala Ala Ala Gly Ala Gly Ala Gly Ala Gly Gly Ala
            50                55                60

Gly Gly Tyr Gly Arg Gly Ala Gly Ala Gly Ala Gly Ala Ala Ala Gly
65                70                75                80

Ala Gly Ala Gly Ala Ala Gly Ala Gly Ala Gly Gly Ala Gly Gly
                85                90                95

Tyr Gly Thr Gly Gln Gly Tyr Gly Glu Gly Ala Gly Ala Gly Ala Gly
                100                105                110

Val Gly Ala Gly Gly Ala Gly Gly Tyr Gly Arg Gly Ala Gly Ala Gly
                115                120                125

Ala Gly Ala Gly Ala Gly Gly Tyr Gly Ala Gly Gln Gly Tyr Gly Ala
                130                135                140

Gly Ala Gly Ala Gly Ala Ala Ala Ala Ala Gly Ala Gly Ala Gly Ala
145                150                155                160

Gly Gly Ala Gly Gly Tyr Gly Arg Gly Ala Gly Ala Gly Ala Gly Ala
                165                170                175

```
Gly Ala Ala Gly Ala Gly Ala Gly Gly Ala Gly Gly Tyr Gly Ala
                180                 185                 190

Gly Gln Gly Tyr Gly Ala Gly Ala Gly Ala Ala Ala Gly Ala
        195                 200                 205

Gly Ala Gly Gly Ala Arg Gly Tyr Gly Ala Arg Gln Gly Tyr Gly Ser
210                 215                 220

Gly Ala Gly Ala Gly Ala Gly Ala Arg Ala Gly Gly Ala Gly Gly Tyr
225                 230                 235                 240

Gly Arg Gly Ala Gly Ala Gly Ala Ala Ala Ser Gly Ala Gly Ala
                245                 250                 255

Gly Gly Tyr Gly Ala Gly Gln Gly Tyr Gly Ala Gly Ala Gly Ala Val
        260                 265                 270

Ala Ser Ala Ala Ala Gly Ala Gly Ser Gly Ala Gly Gly Ala Gly Gly
        275                 280                 285

Tyr Gly Arg Gly Ala Gly Ala Val Ala Gly Ala Gly Ala Gly Gly Ala
        290                 295                 300

Gly Gly Tyr Gly Ala Gly Gly Ala Ala Ala Gly Val Gly Ala Gly
305                 310                 315                 320

Gly Ser Gly Gly Tyr Gly Gly Arg Gln Gly Gly Tyr Ser Ala Gly Ala
                325                 330                 335

Gly Ala Gly Ala Ala Ala Ala Gly Ala Gly Ala Gly Gly Thr Gly
        340                 345                 350

Gly Tyr Gly Arg Gly Ser Gly Ala Gly Ala Ala Ala Gly Ala Ala Ala
        355                 360                 365

Gly Ala Gly Ala Ala Gly Gly Tyr Gly Tyr Gly Ala Gly Ala Gly
        370                 375                 380

Ala Gly Ser
385

<210> SEQ ID NO 25
<211> LENGTH: 430
<212> TYPE: PRT
<213> ORGANISM: Nephilengys cruentata

<400> SEQUENCE: 25

Tyr Gly Arg Gly Ala Gly Ala Gly Ala Gly Ala Gly Ala Ala
1               5                  10                  15

Ala Gly Ala Gly Ala Gly Gly Ala Gly Gly Tyr Gly Ala Gly Gln Gly
                20                  25                  30

Tyr Gly Ala Gly Ala Gly Ala Gly Ala Ala Ala Ala Gly Ala Gly
        35                  40                  45

Ala Gly Ala Gly Gly Ala Gly Gly Phe Gly Arg Gly Ala Gly Ala Gly
    50                  55                  60

Ala Gly Ala Gly Ala Gly Ala Ala Gly Ala Gly Ala Gly Gly Ala
65                  70                  75                  80

Gly Gly Tyr Gly Ala Gly Gln Gly Tyr Gly Ala Gly Ala Gly Ala Gly
        85                  90                  95

Ala Ala Ala Ala Ala Gly Ala Gly Ala Gly Ala Gly Gly Ala Gly Gly
        100                 105                 110

Tyr Gly Arg Gly Ala Gly Ala Gly Ala Gly Ala Gly Ala Ala Ala
        115                 120                 125

Ala Gly Ala Gly Ala Gly Gly Ala Gly Gly Tyr Gly Ala Gly Gln Gly
        130                 135                 140

Tyr Gly Ala Gly Ala Gly Ala Gly Ala Ala Ala Ala Ala Gly Ala Gly
```

```
                        145                 150                 155                 160
Ala Gly Thr Gly Gly Ala Gly Gly Tyr Gly Ala Gly Gln Gly Tyr Gly
                    165                 170                 175
Ala Gly Ala Gly Ala Gly Ala Gly Ala Gly Ala Gly Ala Gly Ala Gly
                180                 185                 190
Gly Ala Gly Gly Tyr Gly Arg Gly Ala Gly Ala Gly Ala Gly Ala Gly
            195                 200                 205
Ala Gly Ala Gly Ala Gly Gly Tyr Gly Val Gly Gln Gly Tyr Gly
        210                 215                 220
Ala Gly Ala Gly Ala Gly Ala Gly Ser Ala Ala Gly Asn Ala
225                 230                 235                 240
Phe Ala Gln Ser Leu Ser Ser Asn Leu Leu Ser Ser Gly Asp Phe Val
                245                 250                 255
Gln Met Ile Ser Thr Thr Thr Ser Thr Asp Gln Ala Val Ser Val Ala
                260                 265                 270
Thr Ser Val Ala Gln Asn Val Gly Asn Gln Leu Gly Leu Asp Ala Asn
                275                 280                 285
Ala Met Asn Asn Leu Leu Ala Ala Val Gly Gly Tyr Val Ser Ser Leu
            290                 295                 300
Gly Gly Ala Val Ala Asp Ala Ala Ala Tyr Ala Asn Ala Ile Ser Ser
305                 310                 315                 320
Ala Ile Gly Asn Val Leu Ala Asn Thr Gly Ser Ile Asn Glu Ser Thr
                325                 330                 335
Ala Ser Ser Ala Ala Ser Ser Ala Ala Ser Ser Val Thr Thr Thr Leu
                340                 345                 350
Thr Ser Tyr Gly Pro Ala Val Phe Tyr Gly Arg Gly Ala Gly Ala Gly
            355                 360                 365
Ala Ala Ala Ala Ala Gly Gly Ala Gly Gly Ala Gly Gly Tyr Gly
        370                 375                 380
Ser Gly Ala Gly Ala Gly Gly Ala Gly Gly Tyr Gly Ala Gly Ala Gly
385                 390                 395                 400
Ala Gly Ala Ala Ala Gly Ala Gly Ala Gly Gly Ser Gly Gly Tyr Gly
                405                 410                 415
Gly Arg Gln Gly Gly Tyr Gly Ala Gly Ala Gly Ala Gly Ser
            420                 425                 430

<210> SEQ ID NO 26
<211> LENGTH: 673
<212> TYPE: PRT
<213> ORGANISM: Nephilengys cruentata

<400> SEQUENCE: 26

Ala Pro Arg Pro Leu Pro Ala Pro Ala Pro Arg Pro Leu Pro Ala Pro
1               5                   10                  15
Ala Pro Arg Pro Leu Pro Ala Pro Leu Pro Ala Pro Leu Pro Arg Pro
                20                  25                  30
Arg Pro Ala Pro Ile Val Ser Gln Val Gln Gln Ala Ser Ala Leu Gln
            35                  40                  45
Ala Gln Ser Gln Gln Ser Ala Phe Ala Gln Ser Gln Gln Ser Ser Ile
        50                  55                  60
Ala Gln Ser Gln Gln Ala Ser Val Ala Gln Ser Gln Arg Ala Ser Val
65                  70                  75                  80
Ser Gln Ser Gln Gln Ser Ser Asn Ala Phe Ser Ser Ala Ala Ser Phe
                85                  90                  95
```

```
Gly Ala Ser Ser Val Ala Ser Ser Ala Ser Thr Tyr Phe Asn Ser Gly
                100                 105                 110

Ile Val Gln Ser Ser Ile Ala Ser Ser Leu Gln Ser Ser Ser Ala Leu
            115                 120                 125

Ser Ser Ile Ala Tyr Gly Gln Thr Thr Ala Ser Ile Asn Asp Ile Ala
        130                 135                 140

Ser Ala Val Ala Gly Ser Ile Ala Asn Ser Ile Gly Leu Ser Gln Gln
145                 150                 155                 160

Thr Val Gln Ser Ile Ile Ser Gln Gln Leu Ala Ser Ala Gly Ser Gly
                165                 170                 175

Ala Ser Ala Gln Thr Leu Ala Ser Leu Ile Ser Ser Ala Val Ser Ser
            180                 185                 190

Leu Val Gln Gln Ser Gly Ser Val Ser Ala Gly Gln Glu Gln Ser Ile
        195                 200                 205

Ser Gln Ala Leu Ser Ser Ser Ile Ser Ser Ser Leu Asn Gln Leu Val
210                 215                 220

Ala Ala Arg Pro Leu Pro Ala Pro Ala Pro Arg Pro Leu Pro Ala Pro
225                 230                 235                 240

Leu Pro Ala Pro Leu Pro Arg Pro Arg Pro Ala Pro Ile Val Ser Gln
                245                 250                 255

Val Gln Gln Ala Ser Ala Leu Gln Ala Gln Ser Gln Gln Ser Ala Phe
            260                 265                 270

Ala Gln Ser Gln Gln Ser Ser Ile Ala Gln Ser Gln Gln Ala Ser Val
        275                 280                 285

Ala Gln Ser Gln Gln Ser Ser Ile Ser Gln Ser Gln Gln Ala Ser Val
        290                 295                 300

Ser Gln Ser Gln Gln Ser Ser Asn Ala Phe Ser Ser Ala Ala Ser Ser
305                 310                 315                 320

Gly Ala Ser Ser Val Ala Ser Ser Ala Ser Thr Tyr Phe Asn Ser Gly
                325                 330                 335

Ile Val Gln Ser Ser Ile Ala Ser Ser Leu Gln Ser Ser Ser Ala Leu
            340                 345                 350

Ser Ser Ile Ala Tyr Gly Gln Thr Thr Ala Ser Ile Ser Asp Ile Ala
        355                 360                 365

Ser Ala Val Ala Gly Ser Ile Ala Asn Ser Ile Gly Leu Ser Gln Gln
        370                 375                 380

Thr Val Gln Ser Val Ile Ser Gln Gln Leu Ala Ser Ala Gly Ser Gly
385                 390                 395                 400

Ala Ser Ala Gln Thr Leu Ala Ser Leu Ile Ser Ser Ala Val Ser Ser
                405                 410                 415

Leu Val Gln Gln Ser Gly Ser Val Ser Ala Gly Gln Glu Gln Ser Ile
            420                 425                 430

Ser Gln Ala Leu Ser Ser Ser Ile Ser Ser Ser Leu Asn Gln Leu Val
        435                 440                 445

Ala Ala Arg Pro Leu Pro Ala Pro Ala Pro Arg Pro Leu Pro Ala Pro
450                 455                 460

Leu Pro Ala Pro Leu Ser Arg Pro Arg Pro Val Pro Val Gln Arg Pro
465                 470                 475                 480

Gln Pro Val Phe Ser Pro Ser Pro Ala Pro Ala Tyr Ala Pro Ala Pro
                485                 490                 495

Phe Thr Gln Gln Ser Thr Phe Ala Gln Ser Gln Gln Ala Ser Leu Ala
            500                 505                 510

Gln Ser Gln Gln Gln Ala Ser Ile Ala Arg Ser Gln Gln Ala Ser Leu
```

```
                515                 520                 525
Ala Gln Ser Gln Gln Ser Ala Phe Ala Gln Ser Gln Gln Val Ala Thr
            530                 535                 540
Ala Gln Ser Gln Gln Ser Ser Gly Gly Phe Ser Thr Ser Ser Thr Gly
545                 550                 555                 560
Ala Ser Gln Ile Ser Ser Ser Ala Ile Ser Thr Ser Ser Gly Ser Ala
                565                 570                 575
Leu Ala Asn Ser Ala Gln Gln Leu Thr Ser Pro Ala Ala Ser Gln Arg
            580                 585                 590
Ile Ser Gln Leu Ser Asn Ser Leu Ala Ser Ala Val Ser Gly Gly Gln
        595                 600                 605
Val Asn Tyr Ala Ala Leu Ser Asn Ser Ile Ala Ser Ala Ala Ser Gln
        610                 615                 620
Ile Gly Gly Gly Ser Gly Leu Ser Lys Thr Glu Val Leu Ile Glu Thr
625                 630                 635                 640
Leu Leu Glu Thr Leu Ala Ala Leu Leu Glu Ser Leu Ser Leu Pro Gly
            645                 650                 655
Ser Ala Ser Gly Gly Ser Gln Phe Ala Gln Ala Met Leu Ala Ala Leu
            660                 665                 670
Ala

<210> SEQ ID NO 27
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Tyr Asn Arg Gln Val Leu Pro Ile Tyr Ile Leu Val Ile Val Ser
1               5                   10                  15
Leu Ala Ile Leu Thr Thr His Val Ser Thr Ser Lys Gln Arg Pro Phe
            20                  25                  30
Tyr Ile Met Gly His Met Val Asn Ser Ile Glu Glu Ile Ser Glu Phe
        35                  40                  45
Leu Glu Arg Gly Ser Asn Val Leu Glu Ser Asp Val Gln Phe Phe Ser
    50                  55                  60
Asn Gly Ser Val Lys Ala Val Arg His Gly Phe Pro Cys Asp Cys Gly
65                  70                  75                  80
Arg Phe Cys Glu Asn Thr Ala Asn Leu Ala Asp Tyr Leu Gln Ser Val
                85                  90                  95
Arg Tyr Thr Asp Pro Asp Thr Pro Asp Ser Tyr Tyr Asn Gln Leu Val
            100                 105                 110
Leu Gln Phe Phe Asp Leu Lys Leu Ser Thr Ser Glu Asn Lys Arg Gln
        115                 120                 125
Ser Gly Arg Glu Ile Ala His His Val Leu Asp Tyr Leu Tyr Gly Glu
    130                 135                 140
Glu Gly Glu Arg Glu Lys Glu Ile Arg Val Val Ile Tyr Phe Glu Lys
145                 150                 155                 160
Leu Glu Glu Lys Asp Val Ile Leu Gly Phe Met Asp Val Phe Lys Leu
                165                 170                 175
Arg Asn Gln Thr Ser Arg Leu Arg Asp Val Gly Phe Asp Gly Gly Thr
            180                 185                 190
Gly Asn Ile Ser Asp Ile Ala Arg Met Phe Ser Lys Phe Asn Ile Lys
```

```
                         195                 200                 205
Asp Asn Ile Tyr Leu Gly Asp Gly Ala Thr Asn Cys Phe Glu Pro Phe
    210                 215                 220

Lys Ser Phe Val Arg Leu Lys Asn Ala Ile Asp Asn Arg Asp Ser Arg
225                 230                 235                 240

Lys Gly Phe Val Ser Lys Ile Tyr Gln Tyr Thr Asn Asp Ile Lys Thr
                245                 250                 255

Thr Met Met Arg Ser Leu Arg Leu Gly Val Asp Gly Met Ile Thr Asn
                260                 265                 270

Lys Pro Glu Arg Leu Leu Glu Val Leu Gln Glu Pro Glu Phe Ala Lys
            275                 280                 285

Asp Phe Arg Leu Ala Thr Ile Tyr Asp Asp Pro Phe Glu Tyr Phe Cys
    290                 295                 300

Asp Glu
305

<210> SEQ ID NO 28
<211> LENGTH: 616
<212> TYPE: PRT
<213> ORGANISM: Avicularia juruensis

<400> SEQUENCE: 28

Tyr Ser Leu Ala Ser Ser Ile Ala Ser Ala Ser Ser Ser Ala Ser
1               5                   10                  15

Ser Ala Ala Ala Ala Ala Ser Ser Ser Ala Ala Gly Ala Ala
                20                  25                  30

Ala Ala Ser Glu Ala Ala Ala Ser Ala Ala Ala Thr Ser Thr Thr Thr
            35                  40                  45

Thr Thr Ser Thr Ser Arg Ala Ala Ala Ala Ser Ala Ala Ala Ala
    50                  55                  60

Ala Ser Ala Ser Gly Ala Ala Gly Ala Ala Gly Ala Ala Ser Ala Ala
65                  70                  75                  80

Ser Ala Ala Ser Ala Ser Ser Leu Gln Gln Ser Leu Gly Ser Ala
                85                  90                  95

Leu Ala Gln Ser Ser Phe Ala Ala Phe Ala Gln Ala Ser Ser
                100                 105                 110

Ala Ala Ser Ala Ala Ile Ala Tyr Ala Leu Ala Gln Thr Val Ala
                115                 120                 125

Asn Gln Ile Gly Phe Ser Ser Tyr Ser Ser Ala Phe Ala Arg Ala Ala
    130                 135                 140

Ser Ser Ala Val Tyr Ser Ile Gly Gly Leu Ala Ser Ala Ser Ala Tyr
145                 150                 155                 160

Ala Phe Ala Phe Ala Ser Ala Phe Ser Gln Val Leu Ser Asn Tyr Gly
                165                 170                 175

Leu Leu Asn Ile Asn Asn Ala Tyr Ser Leu Ala Ser Ser Ile Ala Ser
                180                 185                 190

Ala Ala Ser Ser Ser Ala Ser Ser Ala Ala Ala Ala Ala Ser Ser
            195                 200                 205

Ser Ser Ala Ala Ala Gly Ala Ala Ala Ser Gly Thr Ala Ala Ser
    210                 215                 220

Ala Ala Ala Thr Ser Thr Thr Thr Thr Ser Thr Ser Arg Ala Ala
225                 230                 235                 240

Ala Ala Ala Ser Ala Ala Ala Ala Ser Ala Ser Gly Ala Ala Asp
                245                 250                 255
```

```
Ala Ala Gly Ala Ala Ser Ala Ala Ser Ala Ala Ser Ala Ser Ser Ser
            260                 265                 270
Leu Gln Gln Ser Leu Gly Ser Ala Leu Ala Gln Ser Ser Ser Phe Ala
        275                 280                 285
Ala Ala Phe Ala Gln Ala Asn Ser Ala Ala Ser Ala Ala Ala Ile Ala
    290                 295                 300
Tyr Ala Leu Ala Gln Thr Val Ala Asn Gln Ile Gly Phe Ser Ser Tyr
305                 310                 315                 320
Ser Ser Ala Phe Ala Ser Ala Ser Ala Val Ser Ser Leu Gly
            325                 330                 335
Gly Phe Ala Ser Ala Ser Ala Tyr Ala Phe Ala Phe Ala Ser Ala Phe
            340                 345                 350
Ser Gln Val Leu Ser Asn Tyr Gly Leu Leu Asn Ile Asn Asn Ala Tyr
        355                 360                 365
Ser Leu Ala Ser Ser Ile Ala Ser Ala Ala Ser Ser Ser Ala Ser Ser
    370                 375                 380
Ala Ala Ala Ala Ser Tyr Ser Phe Ser Ala Thr Gly Ala Ala Ser
385                 390                 395                 400
Ser Ala Ala Val Gly Ala Ala Thr Ser Gly Ala Ala Thr Ser Gly
            405                 410                 415
Ala Ala Thr Ser Ser Ser Ser Ala Thr Gly Val Gly Gly Ser Val Ser
            420                 425                 430
Ser Gly Ala Ser Pro Ala Ser Ala Gly Thr Ala Thr Gly Gly Ile
            435                 440                 445
Ser Phe Leu Pro Val Gln Thr Gln Arg Gly Phe Gly Leu Val Pro Ser
450                 455                 460
Pro Ser Gly Asn Ile Gly Ala Asn Phe Pro Gly Ser Gly Glu Phe Gly
465                 470                 475                 480
Pro Ser Pro Leu Thr Ser Pro Val Tyr Gly Pro Gly Ile Leu Gly Pro
            485                 490                 495
Gly Leu Val Val Pro Ser Leu Gln Gly Leu Leu Pro Pro Leu Phe Val
            500                 505                 510
Leu Pro Ser Asn Ser Ala Thr Glu Arg Ile Ser Ser Met Val Ser Ser
        515                 520                 525
Leu Leu Ser Ala Val Ser Ser Asn Gly Leu Asp Ala Ser Ser Phe Gly
    530                 535                 540
Asp Thr Ile Ala Ser Leu Val Ser Gln Ile Ser Val Asn Asn Ser Asp
545                 550                 555                 560
Leu Ser Ser Ser Gln Val Leu Leu Glu Ala Leu Leu Glu Ile Leu Ser
            565                 570                 575
Gly Met Val Gln Ile Leu Ser Tyr Ala Glu Val Gly Thr Val Asn Thr
            580                 585                 590
Lys Thr Val Ser Ser Thr Ser Ala Ala Val Ala Gln Ala Ile Ser Ser
        595                 600                 605
Ala Phe Ser Gly Asn Gln Asn Ser
    610                 615

<210> SEQ ID NO 29
<211> LENGTH: 562
<212> TYPE: PRT
<213> ORGANISM: Avicularia juruensis

<400> SEQUENCE: 29

Thr Thr Ser Thr Ser Thr Ala Ala Ala Ala Ala Ala Ala Ala Asp Phe
1               5                   10                  15
```

```
Gly Ser Gly Ala Ala Arg Ala Ala Gln Thr Ala Ser Ala Ala Ser Ala
            20                  25                  30

Ala Ser Ala Ser Ser Ser Leu Gln Gln Ser Leu Gly Ser Ala Leu Ala
        35                  40                  45

Gln Ser Ser Ser Phe Ala Ala Phe Asp Gln Ala Asn Ser Ala Ala
    50                  55                  60

Ser Ala Ala Ala Ile Ala Tyr Ala Leu Ala Gln Ser Ala Ala Asn Gln
65                  70                  75                  80

Val Gly Leu Ser Ser Tyr Ser Ala Ala Ile Ser Asn Ala Ala Ala
                85                  90                  95

Ala Val Gly Ser Val Gly Gly Tyr Ala Ser Ala Ser Ala Tyr Ala Phe
            100                 105                 110

Ala Phe Ala Ser Gly Val Ser Gln Val Leu Ser Asn Tyr Gly Leu Ile
        115                 120                 125

Asn Leu Ser Asn Ala Leu Phe Leu Ala Ser Ser Ile Ala Asn Ala Ala
130                 135                 140

Ser Ala Ser Ala Ser Ser Ala Ala Ala Ala Ser Ser Ser Ser Ala
145                 150                 155                 160

Ala Thr Gly Ala Ala Ala Ala Leu Gly Gly Ala Gly Ser Ala Ala Ala
            165                 170                 175

Thr Ser Thr Thr Thr Ile Thr Ser Thr Ser Thr Ala Val Ala Ala Ala
        180                 185                 190

Ser Gly Ser Gly Ala Ala Arg Ala Ala Gln Thr Ala Ser Ala Ala Ser
        195                 200                 205

Ala Ala Ser Ala Ser Ser Ser Leu Ala Gln Ser Leu Gly Ser Ala Leu
210                 215                 220

Ala Gln Ser Ser Ser Phe Ala Ala Ala Phe Asp Gln Gly Asn Ser Ala
225                 230                 235                 240

Ala Ser Ala Ala Ala Ile Ala Tyr Val Leu Ala Gln Ser Ala Ala Asn
                245                 250                 255

Lys Val Gly Leu Ser Ser Tyr Ser Ala Ala Ile Ser Asn Ala Ala Ser
                260                 265                 270

Ala Ala Val Glu Ser Val Gly Gly Tyr Ala Ser Ala Ser Ala His Ala
            275                 280                 285

Phe Ala Phe Ala Ser Ala Val Ser Gln Val Leu Ser Asn Tyr Gly Leu
        290                 295                 300

Ile Asn Leu Ser Asn Ala Leu Ser Leu Ala Ser Ser Ile Ala Asn Ala
305                 310                 315                 320

Val Ser Ala Ser Ala Ser Ser Ala Ala Val Ser Ser Ala Ala Ala
                325                 330                 335

Ala Thr Gly Ala Thr Ser Ser Ala Ala Val Gly Ala Ala Ala Thr Cys
            340                 345                 350

Gly Ala Ala Thr Ser Ala Ser Ser Ala Thr Gly Val Gly Glu Thr Val
        355                 360                 365

Ala Cys Ala Thr Ser Pro Ala Ser Thr Gly Thr Ala Ala Gly Gly Gly
        370                 375                 380

Ile Ser Ser Leu Pro Val Gln Thr Gln Pro Gly Phe Gly Phe Leu Leu
385                 390                 395                 400

Ser Pro Ser Gly Asn Ile Gly Pro Ser Val Ser Gly Ser Gly Phe
            405                 410                 415

Gly Pro Ser Pro Leu Pro Ser Pro Ala Ser Asp Gly Phe Ser Pro Ser
            420                 425                 430
```

Pro Leu Pro Ser Gln Val Tyr Gly Pro Gly Ile Leu Gly Pro Gly Leu
            435                 440                 445

Val Ala Pro Ser Leu Glu Gly Leu Leu Pro Pro Leu Ser Ile Leu Pro
450                 455                 460

Ser Asp Ser Ala Asn Glu Arg Ile Ser Ser Val Val Ser Ser Leu Leu
465                 470                 475                 480

Ala Ala Val Ser Ser Asn Gly Leu Asp Ala Ser Ser Leu Gly Asp Asn
                485                 490                 495

Leu Ala Ser Leu Val Ser Gln Ile Ser Ala Asn Asn Ala Asp Leu Ser
            500                 505                 510

Ser Ser Gln Val Met Val Glu Ala Leu Leu Glu Val Leu Ser Gly Ile
        515                 520                 525

Val Gln Ile Leu Ser Tyr Ala Glu Val Gly Ala Val Asn Thr Glu Thr
    530                 535                 540

Val Ser Ser Thr Ser Ser Ala Val Ala Gln Ala Ile Ser Ser Ala Val
545                 550                 555                 560

Leu Gly

<210> SEQ ID NO 30
<211> LENGTH: 476
<212> TYPE: PRT
<213> ORGANISM: Avicularia juruensis

<400> SEQUENCE: 30

Gly Ser Gly Ser Gly Ser Gly Ala Gly Ser Gly Gly Ser
1               5                   10                  15

Gly Ala Gly Ser Gly Ser Gly Ser Ala Gly Ala Gly Ser
            20                  25                  30

Gly Ser Gly Ser Gly Ser Gly Ala Gly Ser Gly Ser Gly Ser
        35                  40                  45

Gly Ser Gly Ala Gly Ser Gly Ser Gly Ser Gly Ser Gly Ala
    50                  55                  60

Arg Ser Gly Ser Gly Ser Gly Ser Gly Ser Gly Ala Gly Ser Gly Ser
65                  70                  75                  80

Gly Ser Gly Ser Gly Ala Gly Ala Gly Ser Gly Ser Gly Ser
            85                  90                  95

Gly Ser Gly Ala Gly Ser Gly Ser Gly Ala Gly Ser Gly Ser Gly Ser
                100                 105                 110

Gly Ser Gly Ala Gly Ser Gly Ser Gly Ser Gly Ser
            115                 120                 125

Gly Ala Gly Ala Gly Ser Gly Ser Gly Ser Gly Arg Gly Ala Gly Ser
    130                 135                 140

Gly Ser Gly Ser Gly Ser Gly Ala Gly Ser Gly Ser Gly Ser
145                 150                 155                 160

Gly Ser Gly Arg Gly Ala Gly Ser Gly Ser Gly Ser Gly Ser
                165                 170                 175

Gly Ala Gly Ala Gly Ser Gly Ser Gly Ser Gly Ala Gly Ser
            180                 185                 190

Gly Ser Gly Ser Gly Ser Gly Ala Gly Ser Gly Ser Gly Ser
        195                 200                 205

Gly Ser Gly Ser Gly Ala Gly Ser Gly Ser Gly Ser Gly Ser
    210                 215                 220

Gly Ala Gly Ser Gly Ser Gly Ser Gly Ser Gly Ala Gly Ser
225                 230                 235                 240

Gly Ser Gly Ser Gly Ser Gly Ser Gly Ala Gly Ser Gly Ser Gly Ser
                245                 250                 255

Gly Ser Gly Ser Gly Ala Gly Ser Gly Ser Gly Ser Gly Ser
            260                 265                 270

Gly Ala Gly Ala Gly Ser Gly Ser Gly Ser Cys Arg Lys Asp Ala Gly
                275                 280                 285

Gly His Asp Gly Gly Tyr Gly Lys Lys Leu Gly Phe Glu Phe Gly Thr
            290                 295                 300

Pro Ala Ala Ala Val Thr Leu Gly Pro Gly Ala Gly Gln Gln Gly
305                 310                 315                 320

Pro Gly Gly Ala Gly Gln Gln Gly Pro Gly Gly Gln Gly Pro Tyr Gly
            325                 330                 335

Pro Val Ala Ser Ala Ala Ala Val Ala Gly Gly Tyr Gly Pro Gly
            340                 345                 350

Ala Leu Pro Gln Gly Pro Ala Arg Gln Gly Pro Ser Gly Pro Val Ser
            355                 360                 365

Ser Ala Pro Val Ala Ser Ala Ala Ala Arg Leu Ser Ser Pro Gln
            370                 375                 380

Ala Ser Ser Arg Val Ser Ser Ala Phe Phe Ser Leu Val Ser Ser Gly
385                 390                 395                 400

Pro Thr Ser Pro Gly Ala Leu Ser Asn Ala Ile Ser Ser Val Val Ser
            405                 410                 415

Gln Val Ser Ala Ser Asn Pro Gly Leu Ser Gly Cys Asp Val Leu Val
            420                 425                 430

Gln Ala Leu Leu Glu Ile Val Ser Ala Leu Val Ser Ile Leu Ala Ser
            435                 440                 445

Ser Ser Ile Gly Gln Ile Asn Tyr Gly Ala Ser Ala Gln Tyr Ala Ser
            450                 455                 460

Leu Val Gly Gln Ser Val Asn Gln Ala Leu Arg Tyr
465                 470                 475

<210> SEQ ID NO 31
<211> LENGTH: 571
<212> TYPE: PRT
<213> ORGANISM: Avicularia juruensis

<400> SEQUENCE: 31

Gln Thr Leu Ser Met Thr Ser Phe Thr Gln Ile Ala Thr Leu Phe
1               5                  10                  15

Phe Val Phe Val Gly Val Ala Ile Ala Arg Asp Asn Asn Leu Ser Pro
            20                  25                  30

Asn Val Pro Tyr Ile Thr Gln Glu Asp Gly Glu Ser Phe Leu Leu Ala
            35                  40                  45

Phe Glu Glu Ala Ile Ser Glu Lys Met Gln Pro Asp Gly Ile Ser Asp
        50                  55                  60

Leu Glu Phe Leu Phe Gly Ser Leu Leu Ser Leu Ile Pro Gln Arg Ser
65                  70                  75                  80

Gly Ser Leu Ser Val Ala Arg Leu Gln Ala Leu Asn Met Ala Leu Ala
            85                  90                  95

Ser Ile Ile Ala Glu Ile Val Arg Ile Asp Gly Arg Gly Ser Met Glu
            100                 105                 110

Glu Lys Ile Glu Phe Val Arg Glu Gly Leu Ile Lys Ala Phe Leu Ala
        115                 120                 125

Thr Ser Gly Phe Val Asn Thr Ala Leu Ile Lys Glu Val Leu Ser Met
            130                 135                 140

```
Ile Arg Leu Phe Tyr Glu Glu Glu Gly Asp Asn Thr Ile Asp Gln
145                 150                 155                 160

Asn Phe Pro Gln Gln Glu Tyr Pro Glu Val Thr Ser Gln Phe Asp Ser
            165                 170                 175

Ala Gly Lys Phe Glu Thr Phe Asp Ser Val Ala Gly Gln Ala Ser
            180                 185                 190

Thr Glu Ala Ser Gln Ser Ser Thr Val Ser Thr Thr Ser Thr
            195                 200                 205

Ser Gln Thr Tyr Ser Glu Gln Thr Ala Ser Ser Asp Val Ala Ser
            210                 215                 220

Thr Ala Ala Thr Ser Glu Ala Ser Ser Arg Phe Thr Gln Tyr Val Thr
225                 230                 235                 240

Ser Phe Leu Leu Gln Asp Leu Glu Phe Val Asp Gln Tyr Asn Thr Ile
                245                 250                 255

Ala Ser Ser Gly Ile Ala Ser Thr Leu Ala Ser Ala Ser Ala Glu Ala
                260                 265                 270

Val Ala Tyr Ser Ile Gly Gln Gly Ser Ile Ala Ser Ala Ile Ala Ser
                275                 280                 285

Ala Val Ser Gln Ala Thr Ala Asn Ile Ser Phe Val Thr Val Pro Phe
290                 295                 300

Val Phe Val His Ala Phe Ala Ser Ala Val Ser Glu Thr Leu Ser Ala
305                 310                 315                 320

Phe Gly Val Leu Asn Leu Asp Asn Val Asn Thr Leu Ala Ser Glu Phe
                325                 330                 335

Ala Asn Ser Leu Phe Asn Ala Ile Leu Thr Ala Ser Ala Ser Ser Thr
                340                 345                 350

Thr Ser Ala Ser Ala Ser Ser Thr Thr Ser Ala Ser Ala Ser Ser Thr
                355                 360                 365

Thr Ser Ala Ser Ala Ser Ser Thr Thr Ser Ala Ser Ala Ser Ser Glu
                370                 375                 380

Thr Ser Ala Ser Ala Ala Ser Ala Ser Thr Ala Leu Gln Thr Asp Ser
385                 390                 395                 400

Thr Ala Ala Gly Ser Leu Ala Ser Ser Gly Thr Ser Ser Ala Asn Tyr
                405                 410                 415

Gly Pro Ser Phe Gly Ile Glu Ser Pro Phe Ser Pro Ala Phe Gly Ala
                420                 425                 430

Gly Ser Gly Pro Asn Thr Phe Asp Phe Leu Thr Pro Ser Pro Ser Ile
            435                 440                 445

Pro Ala Leu Pro Thr Asn Pro Glu Leu Ser Arg Tyr Ser Pro Leu Ile
            450                 455                 460

Ser Glu Leu Leu Gln Ser Pro Ser Gly Leu Lys Ser Pro Ala Ala Asp
465                 470                 475                 480

Glu Arg Ile Ala Ser Ser Val Pro Leu Leu Ala Leu Ala Val Thr Asn
                485                 490                 495

Gly Phe Asn Pro Ser Leu Phe Ser Val Val Leu Ser Ser Leu Val Ser
                500                 505                 510

Gln Ile Ser Gln Ser Ser Ser Phe Thr Ser Ser Gln Val Leu Ile Glu
                515                 520                 525

Ala Ile Leu Glu Ile Ile Ser Gly Met Leu Asn Ile Leu Thr Ser Ala
                530                 535                 540

Gln Leu Gly Leu Val Ser Thr Ala Ser Leu Ala Ala Thr Val Ser Ser
545                 550                 555                 560
```

Ile Val Gln Ser Ile Ser Ser Ser Ile Ile Ala
            565                 570

<210> SEQ ID NO 32
<211> LENGTH: 733
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Thr Gly Gly Arg His Asp Glu Asp Lys Gly Arg Thr Gly Glu
1               5                   10                  15

Arg His Asp Glu Gly Ser Lys Gly Gly Thr Asn Gly Arg His Gly Glu
            20                  25                  30

Ser Ser Arg Glu Gly Pro Asp Gly Arg His Gly Glu Arg Pro Arg Gly
            35                  40                  45

Gly Val Asp Gly Arg His Gly Glu Gly Cys Arg Glu Gly Ala Asp Gly
        50                  55                  60

Arg His Ser Glu Gly Ser Arg Gly Ser Gly Glu Arg His Gly Glu
65                  70                  75                  80

Gly Ser Arg Gly Gly Val Asp Gly Arg His Gly Glu Gly Cys Arg Glu
                85                  90                  95

Gly Ala Asp Gly Arg His Ser Lys Gly Ser Arg Gly Ala Gly Glu
            100                 105                 110

Arg His Gly Glu Gly Ser Arg Gly Gly Val Asp Gly Arg His Gly Glu
        115                 120                 125

Gly Cys Arg Glu Gly Ser Glu Arg Arg His Gly Glu Gly Ser Arg Gly
    130                 135                 140

Asp Ala Asp Gly Arg His Gly Glu Gly Tyr Lys Gly Gly Ser Glu Arg
145                 150                 155                 160

Arg His Gly Glu Gly Phe Arg Arg Gly Val Asp Gly Arg His Gly Glu
                165                 170                 175

Gly Cys Arg Gly Gly Pro Glu Arg Arg His Gly Glu Gly Ser Arg Ile
            180                 185                 190

Gly Gly Asp Gly Lys His Gly Glu Gly Ser Arg Glu Gly Ala His Gly
        195                 200                 205

Gly His Gly Glu Gly Pro Arg Glu Gly Val Asp Gly Gly His Gly Glu
    210                 215                 220

Arg Ser Arg Gly Gly Val Asp Gly Arg His Gly Glu Gly Ser Arg Glu
225                 230                 235                 240

Gly Ala Asp Gly Gly His Gly Glu Gly Ser Arg Glu Gly Val Asp Gly
                245                 250                 255

Arg His Gly Glu Gly Ser Arg Gly Gly Val Asp Gly Arg His Gly Glu
            260                 265                 270

Gly Ser Arg Gly Gly Phe Asp Gly Arg His Gly Glu Gly Cys Lys Gly
        275                 280                 285

Gly Pro Glu Arg Arg His Gly Glu Gly Ser Arg Ile Gly Gly Asp Gly
    290                 295                 300

Lys His Gly Glu Gly Ser Arg Glu Gly Ala His Gly Gly His Gly Glu
305                 310                 315                 320

Gly Pro Arg Glu Gly Val Asp Gly Gly His Gly Glu Arg Ser Arg Gly
                325                 330                 335

Glu Val Asp Gly Gly His Gly Glu Gly Thr Arg Glu Gly Ala Asp Gly
            340                 345                 350

Gly Tyr Gly Glu Gly Ser Arg Glu Gly Asp Asp Gly Arg His Gly Glu
            355                 360                 365

Arg Pro Arg Gly Gly Val Asp Gly Arg His Gly Glu Gly Cys Arg Glu
        370                 375                 380

Gly Ala Asp Gly Arg His Ser Glu Gly Ser Arg Gly Gly Ala Gly Glu
385                 390                 395                 400

Arg His Gly Glu Gly Ser Arg Gly Val Asp Gly Arg His Gly Glu
                405                 410                 415

Gly Cys Arg Glu Gly Ala Asp Gly Arg His Ser Glu Gly Ser Arg Gly
            420                 425                 430

Gly Ala Gly Glu Arg His Gly Glu Gly Ser Arg Gly Val Asp Gly
            435                 440                 445

Arg His Gly Glu Gly Cys Arg Glu Gly Tyr Glu Arg Arg His Gly Ala
        450                 455                 460

Gly Cys Arg Gly Gly Ile Tyr Arg Arg His Asp Glu Gly Tyr Lys Gly
465                 470                 475                 480

Gly Ser Glu Arg Arg His Gly Glu Gly Phe Arg Arg Gly Val Asp Glu
                485                 490                 495

Arg His Gly Glu Gly Cys Arg Gly Gly Pro Glu Arg Arg His Gly Glu
                500                 505                 510

Gly Ser Arg Ile Gly Gly Asp Gly Lys His Gly Glu Gly Ser Arg Glu
            515                 520                 525

Gly Ala His Gly Arg His Gly Glu Gly Pro Arg Lys Gly Val Asp Gly
        530                 535                 540

Gly His Gly Glu Gly Pro Arg Glu Gly Val Asp Gly His Gly Glu
545                 550                 555                 560

Arg Ser Arg Gly Gly Val Asp Gly Arg His Gly Glu Gly Ser Arg Glu
                565                 570                 575

Gly Ala Asp Gly Gly His Gly Glu Gly Ser Arg Glu Gly Val Asp Gly
            580                 585                 590

Arg His Gly Glu Gly Ser Arg Gly Val Asp Gly Arg His Gly Glu
        595                 600                 605

Gly Ser Arg Gly Gly Phe Asp Gly Arg His Gly Glu Gly Arg Glu Gly
        610                 615                 620

Ala Asp Gly Gly His Gly Glu Gly Ser Arg Glu Gly Ala Glu Gly Gly
625                 630                 635                 640

Tyr Gly Glu Gly Ser Arg Gly Gly Val Asp Gly Gly His Gly Glu Gly
                645                 650                 655

Ser Arg Glu Gly Val Asp Arg Gly His Gly Glu Gly Ser Arg Glu Asp
                660                 665                 670

Ala Asp Gly Gly Ser Ala Glu Gly Ser Arg Glu Gly Asp Asp Gly Lys
            675                 680                 685

Arg Gly Gly Asp Ala Gly Gly Asp Ala Lys Val Ala Phe Glu Ser Asp
        690                 695                 700

Ser Gly Tyr Lys Gly Tyr Gln Gln Ser Tyr Gly Tyr Glu Asp Arg Tyr
705                 710                 715                 720

Ser Phe Gly Lys Leu Asn Gly His Asp Ala Ser Gly Asn
                725                 730

<210> SEQ ID NO 33
<211> LENGTH: 652
<212> TYPE: PRT
<213> ORGANISM: Parawixia bistriata

<400> SEQUENCE: 33

```
Ala Val Gln Ala Leu Ser Ser Leu Gly Ile Asp Gly Asn Asn Leu
1               5                   10                  15

Ala Arg Ile Ala Ser Gln Thr Ile Leu Arg Val Pro Ala Gly Ser Asp
            20                  25                  30

Thr Ser Ala Tyr Ala Gln Ala Phe Ser Thr Ala Leu Phe Asn Ser Gly
        35                  40                  45

Val Leu Asn Ala Ser Asn Val Asn Thr Leu Gly Ser Gln Val Val Ser
    50                  55                  60

Thr Leu Leu Arg Gly Ile Ser Ser Thr Ala Gln Gly Leu Gly Leu Asn
65                  70                  75                  80

Val Asp Ala Gly Ser Val Gln Ser Asp Ile Ser Ser Ser Ser Phe
            85                  90                  95

Leu Ser Thr Ser Ser Ser Ser Thr Ser Ser Ser Gln Thr Thr Ala Ala
                100                 105                 110

Ser Thr Ser Gly Phe Thr Gly Ala Ser Tyr Pro Gly Pro Gln Val Ser
            115                 120                 125

Gln Pro Ala Pro Phe Gly Val Gly Pro Gln Pro Gly Gly Ala Leu Pro
        130                 135                 140

Gly Phe Gly Gln Val Ser Gly Ala Gln Ser Ala Leu Ile Ser Arg Ile
145                 150                 155                 160

Ala Asn Ala Leu Gly Asn Thr Ala Thr Met Arg Ala Val Leu Arg Ser
                165                 170                 175

Gly Val Ser Gln Gln Ile Val Ser Asn Val Gln Gly Ala Val Gln
            180                 185                 190

Ala Leu Ser Ser Ser Leu Gly Ile Asp Gly Asn Asn Leu Ala Arg Ile
        195                 200                 205

Ala Ser Gln Thr Ile Leu Arg Val Pro Ala Gly Ser Asp Thr Ser Ala
    210                 215                 220

Tyr Ala Gln Ala Phe Ser Thr Ala Leu Phe Asn Ser Gly Val Leu Asn
225                 230                 235                 240

Ala Ser Asn Val Asn Thr Leu Gly Ser Gln Val Val Ser Thr Leu Leu
                245                 250                 255

Arg Gly Ile Ser Ser Thr Ala Gln Gly Leu Gly Leu Asn Val Asp Ala
            260                 265                 270

Gly Ser Val Gln Ser Asp Ile Ser Ser Ser Ser Phe Leu Ser Thr
        275                 280                 285

Ser Ser Ser Ser Thr Ser Ser Ser Gln Thr Thr Ala Ala Ser Thr Ser
290                 295                 300

Gly Phe Thr Gly Ala Ser Tyr Pro Gly Pro Gln Val Ser Gln Pro Ala
305                 310                 315                 320

Pro Phe Gly Val Gly Pro Gln Pro Gly Gly Ala Leu Pro Gly Phe Gly
                325                 330                 335

Gln Val Ser Gly Ala Gln Ser Ala Leu Ile Ser Arg Ile Ala Asn Ala
            340                 345                 350

Leu Gly Asn Thr Ala Thr Met Arg Ala Val Leu Arg Ser Gly Val Ser
        355                 360                 365

Gln Gln Ile Val Ser Asn Val Gln Gly Ala Val Gln Ala Leu Ser
    370                 375                 380

Ser Ser Leu Gly Ile Asp Gly Asn Asn Leu Ala Arg Ile Ala Ser Gln
385                 390                 395                 400

Thr Ile Leu Arg Val Pro Ala Gly Ser Asp Thr Ser Ala Tyr Ala Gln
                405                 410                 415
```

```
Ala Phe Ser Thr Ala Leu Phe Asn Ser Gly Val Leu Asn Ala Ser Asn
                420                 425                 430

Val Asn Thr Leu Gly Ser Gln Val Ser Thr Leu Leu Arg Gly Ile
            435                 440                 445

Ser Asn Thr Ala Gln Gly Leu Gly Leu Asn Val Asp Ala Gly Ser Val
450                 455                 460

Gln Ser Asp Ile Ser Ser Ser Ser Phe Leu Ser Thr Ser Ser Ser
465                 470                 475                 480

Ser Thr Ser Ser Ser Gln Thr Thr Ala Ala Ser Thr Ser Gly Phe Ala
                485                 490                 495

Arg Ala Tyr Thr Gly Pro Gln Ile Ser Gln Pro Ala Pro Leu Gly Val
                500                 505                 510

Gly Pro Gln Val Ser Gln Pro Arg Pro Leu Gly Val Ala Pro Gln Thr
            515                 520                 525

Ser Gly Ala Arg Pro Phe Gly Gly Val Thr Gly Pro Ser Ala Gly Ile
530                 535                 540

Ser Leu Gly Ser Ala Leu Asn Ser Pro Ile Gly Leu Arg Ser Gly Leu
545                 550                 555                 560

Ala Ala Ala Arg Ile Ser Gln Leu Thr Ser Ser Leu Gly Asn Ala Ile
                565                 570                 575

Thr Pro Tyr Gly Val Asp Ala Asn Ala Leu Ala Ser Ser Leu Gln Ala
                580                 585                 590

Ser Phe Ser Thr Leu Gln Ser Ser Gly Met Ser Ala Ser Asp Ala Lys
            595                 600                 605

Ile Glu Val Leu Leu Glu Thr Ile Val Gly Leu Leu Gln Leu Leu Ser
            610                 615                 620

Asn Thr Gln Ile Arg Gly Val Asn Met Ala Thr Ala Ser Ser Val Ala
625                 630                 635                 640

Ser Ser Ala Ala Lys Ser Phe Glu Leu Val Leu Ser
                645                 650

<210> SEQ ID NO 34
<211> LENGTH: 437
<212> TYPE: PRT
<213> ORGANISM: Parawixia bistriata

<400> SEQUENCE: 34

Gly Ala Pro Gly Gly Ala Gly Gly Val Gly Pro Gly Gly Gly Ala
1               5                   10                  15

Gly Gly Thr Ser Gly Gly Ala Ser Gly Ser Gly Pro Val Ser Val Ser
            20                  25                  30

Thr Ala Val Asn Val Gly Gly Ala Gly Gly Pro Gly Ala Gly Gly Pro
            35                  40                  45

Gly Ala Gly Gly Val Gly Pro Gly Val Val Gly Pro Gly Gly Leu Gly
        50                  55                  60

Gly Pro Gly Gly Phe Gly Pro Gly Gly Pro Gly Gly Pro Gly Gly
65                  70                  75                  80

Pro Gly Ala Pro Gly Gly Ala Gly Gly Met Phe Gly Pro Gly Gly Ala
                85                  90                  95

Gly Gly Met Tyr Gly Pro Gly Gly Ala Gly Gly Met Tyr Gly Pro Gly
                100                 105                 110

Gly Ala Gly Arg Gly Pro Gly Gly Ala Gly Ala Pro Gly Ala Pro Gly
            115                 120                 125

Gly Pro Gly Gly Pro Gly Gly Pro Gly Gly Phe Gly Gly Gly Ala Gly
```

```
                130                 135                 140
Ala Gly Gly Met Val Pro Gly Ala Ser Arg Gly Pro Gly Ser
145                 150                 155                 160

Gly Pro Val Thr Val Thr Glu Thr Val Thr Val Gly Ala Gly Gly
                165                 170                 175

Pro Gly Pro Gly Gly Ile Gly Gly Ser Ser Gly Pro Gly Ala Gly Gly
                180                 185                 190

Ala Pro Gly Gly Phe Gly Gly Pro Gly Gly Pro Gly Gly
            195                 200                 205

Pro Gly Gly Pro Gly Gly Ala Ala Gly Gly Pro Gly Ala Gly Gly Ala
        210                 215                 220

Gly Pro Gly Gly Ser Gly Pro Ala Thr Val Ser Ser Val Thr Val
225                 230                 235                 240

Val Gly Ala Gly Gly Pro Gly Gly Pro Gly Ala Gly Ile Val Pro
                245                 250                 255

Gly Gly Ile Tyr Gly Pro Gly Gly Ala Gly Gly Val Val Pro Gly Gly
                260                 265                 270

Ile Tyr Gly Pro Gly Gly Val Pro Ser Gly Pro Gly Pro Gly Gly
            275                 280                 285

Pro Val Gly Pro Gly Gly Tyr Gly Ala Pro Gly Gly Leu Gly Val Gly
        290                 295                 300

Ile Leu Pro Gly Thr Ala Ser Ala Gly Thr Ser Gly Pro Thr Thr Val
305                 310                 315                 320

Thr Glu Val Val Ser Ile Asn Val Ser Gly Gly Gln Ser Ser Ser Gly
                325                 330                 335

Val Arg Pro Gly Asn Ser Tyr Thr Pro Ala Ala Gly Gly Ser Ala Arg
                340                 345                 350

Leu Pro Ser Leu Ile Asn Gly Val Met Ser Ser Met Gln Gly Gly Gly
                355                 360                 365

Phe Asn Tyr Gln Asn Phe Gly Asn Val Leu Ser Gln Phe Ala Thr Gly
            370                 375                 380

Ser Gly Thr Cys Asn Ser Asn Asp Ile Asn Leu Leu Met Asp Ala Leu
385                 390                 395                 400

Phe Ala Ala Leu His Thr Leu Ser Tyr Gln Gly Ser Ser Val Pro
                405                 410                 415

Thr Tyr Pro Ser Pro Ala Ala Met Ser Ser Tyr Ser Gln Ser Val Arg
                420                 425                 430

Gly Cys Phe Gly Tyr
            435

<210> SEQ ID NO 35
<211> LENGTH: 528
<212> TYPE: PRT
<213> ORGANISM: Parawixia bistriata

<400> SEQUENCE: 35

Gly Gly Tyr Gly Ala Gly Ala Gly Ala Gly Ala Ala Ala
1               5                   10                  15

Ala Ala Ala Gly Ala Gly Ala Gly Gly Gly Tyr Gly Gly Gly Tyr Gly
                20                  25                  30

Ala Gly Gly Gly Ala Gly Ala Gly Ala Gly Gly Ala Gly Ala Gly
            35                  40                  45

Ala Gly Ala Gly Ala Gly Arg Gly Gly Ala Gly Gly Tyr Gly Ala Gly
        50                  55                  60
```

```
Ala Gly Ala Gly Ala Gly Ala Ala Ala Ala Ala Gly Ala Gly
65                  70                  75                  80

Ala Gly Gly Gly Tyr Gly Gly Tyr Gly Ala Gly Val Gly Ala Gly
                85                  90                  95

Ala Gly Ala Gly Ala Gly Ala Gly Gly Tyr Gly Gly Tyr Gly
            100                 105                 110

Ala Gly Ala Gly Ala Gly Ala Gly Ala Ala Ala Ala Ala Gly
            115                 120                 125

Ala Gly Ala Gly Gly Tyr Gly Gly Tyr Ala Gly Gly Gly
        130                 135                 140

Ala Gly Ala Gly Ala Gly Ala Gly Ala Gly Ala Gly Ala Gly
145                 150                 155                 160

Ala Gly Arg Gly Gly Ala Val Gly Tyr Gly Ala Gly Ala Gly Ala Gly
                165                 170                 175

Ala Ala Ala Ala Ala Ala Gly Ala Gly Ala Gly Gly Tyr Gly
            180                 185                 190

Gly Gly Tyr Gly Ala Gly Gly Ala Gly Ala Gly Ala Gly Ala Gly
        195                 200                 205

Ala Gly Gly Gly Tyr Gly Gly Gly Tyr Gly Ala Gly Gly Ala Gly
        210                 215                 220

Ala Gly Ala Gly Ala Gly Ala Gly Ala Gly Arg Gly Gly Ala Gly Gly
225                 230                 235                 240

Tyr Gly Ala Gly Ala Gly Ala Ala Ala Gly Ala Ala Ala Ala Ala
                245                 250                 255

Ala Gly Ala Gly Ala Gly Gly Tyr Gly Gly Gly Tyr Gly Ala Gly
            260                 265                 270

Gly Gly Ala Gly Ala Gly Ala Gly Ala Ala Gly Ala Gly Ala Gly
        275                 280                 285

Ala Gly Arg Gly Gly Ala Gly Gly Tyr Gly Ala Gly Ala Gly Ala Gly
        290                 295                 300

Ala Gly Ala Ala Ala Ala Ala Gly Ala Gly Ala Gly Gly Gly Tyr
305                 310                 315                 320

Gly Gly Tyr Ser Ala Gly Gly Gly Ala Gly Ala Gly Ser Gly Ala Ala
            325                 330                 335

Ala Gly Ala Gly Ala Gly Arg Gly Gly Ala Gly Gly Tyr Ser Ala Gly
            340                 345                 350

Ala Gly Thr Gly Ala Gly Ala Ala Ala Gly Ala Gly Thr Ala Gly Gly
            355                 360                 365

Tyr Ser Gly Gly Tyr Gly Ala Gly Ala Ser Ser Ser Ala Gly Ser Ser
    370                 375                 380

Phe Ile Ser Ser Ser Ser Met Ser Ser Ser Gln Ala Thr Gly Tyr Ser
385                 390                 395                 400

Ser Ser Ser Gly Tyr Gly Gly Ala Ala Ser Ala Ala Ala Gly Ala
            405                 410                 415

Gly Ala Ala Ala Gly Gly Tyr Gly Gly Tyr Gly Ala Gly Ala Gly
            420                 425                 430

Ala Gly Ala Ala Ala Ala Ser Gly Ala Thr Gly Arg Val Ala Asn Ser
        435                 440                 445

Leu Gly Ala Met Ala Ser Gly Gly Ile Asn Ala Leu Pro Gly Val Phe
    450                 455                 460

Ser Asn Ile Phe Ser Gln Val Ser Ala Ser Gly Ala Ser Gly
465                 470                 475                 480

Gly Ala Val Leu Val Gln Ala Leu Thr Glu Val Ile Ala Leu Leu Leu
```

```
                    485                 490                 495
His Ile Leu Ser Ser Ala Ser Ile Gly Asn Val Ser Ser Gln Gly Leu
                500                 505                 510

Glu Gly Ser Met Ala Ile Ala Gln Gln Ala Ile Gly Ala Tyr Ala Gly
                515                 520                 525

<210> SEQ ID NO 36
<211> LENGTH: 545
<212> TYPE: PRT
<213> ORGANISM: Parawixia bistriata

<400> SEQUENCE: 36

Ala Ala Thr Ala Ser Ala Ala Gly Gly Leu Gly Gly Gln Gly Gly Leu
1               5                   10                  15

Gly Gly Leu Gly Ser Gln Gly Ala Gly Leu Gly Gly Tyr Gly Gln Gly
                20                  25                  30

Gly Ala Gly Gln Gly Gly Ala Ala Ala Ala Ala Ala Ala Gly Gly
                35                  40                  45

Leu Gly Gly Gln Gly Gly Arg Gly Gly Leu Gly Ser Gln Gly Ala Gly
        50                  55                  60

Gln Gly Gly Tyr Gly Gln Gly Gly Ala Gly Gln Gly Gly Ala Ala Ala
65                  70                  75                  80

Ala Ala Ala Ala Ala Gly Gly Leu Gly Gly Gln Gly Gly Leu Gly Ala
                85                  90                  95

Leu Gly Ser Gln Gly Ala Gly Gln Gly Gly Ala Gly Gln Gly Gly Tyr
                100                 105                 110

Gly Gln Gly Gly Ala Ala Ala Ala Ala Ala Gly Gly Leu Gly Gly Gln
                115                 120                 125

Gly Gly Leu Gly Gly Leu Gly Ser Gln Gly Ala Gly Gln Gly Gly Tyr
                130                 135                 140

Gly Gln Gly Gly Ala Gly Gln Gly Gly Ala Ala Ala Ala Ala Ala
145                 150                 155                 160

Ala Gly Gly Leu Gly Gly Gln Gly Gly Leu Gly Gly Leu Gly Ser Gln
                165                 170                 175

Gly Ala Gly Pro Gly Gly Tyr Gly Gln Gly Gly Ala Gly Gln Gly Gly
                180                 185                 190

Ala Ala Ala Ala Ala Ala Ala Gly Gly Leu Gly Gly Gln Gly Gly
                195                 200                 205

Leu Gly Ala Leu Gly Ser Gln Gly Ala Gly Gln Gly Gly Tyr Gly Gln
        210                 215                 220

Gly Gly Ala Gly Gln Gly Gly Ala Ala Ala Ala Ala Ala Gly Gly
225                 230                 235                 240

Leu Gly Gly Gln Gly Gly Leu Gly Ala Leu Gly Ser Gln Gly Ala Gly
                245                 250                 255

Gln Gly Gly Tyr Gly Gln Gly Gly Ser Gln Gly Ala Gly Gln Gly Gly
                260                 265                 270

Tyr Gly Gln Gly Gly Ala Ala Ala Ala Ala Ala Gly Gly Leu
        275                 280                 285

Gly Gly Gln Gly Gly Leu Gly Gly Leu Gly Ser Gln Gly Ala Gly Gln
                290                 295                 300

Gly Gly Tyr Gly Gln Gly Gly Ser Gln Gly Ala Gly Gln Gly Gly Ala
305                 310                 315                 320

Ala Ala Ala Ala Ala Ala Gly Gly Leu Gly Gly Gln Gly Gly Phe
                325                 330                 335
```

Gly Gly Leu Gly Ser Gln Gly Ala Gly Gln Gly Tyr Gly Gln Gly
            340                 345                 350

Gly Ala Gly Gln Gly Gly Ala Ala Ala Ala Ala Ala Ala Gly Val
        355                 360                 365

Leu Gly Gly Gln Gly Gly Leu Gly Gly Leu Gly Ser Gln Gly Ala Gly
        370                 375                 380

Gln Gly Gly Tyr Gly Gln Gly Ala Gly Gln Gly Ala Ala Ala
385                 390                 395                 400

Ala Ala Ala Ala Ala Ala Ala Gly Gly Leu Gly Gly Gln Gly Arg
                405                 410                 415

Gly Gly Leu Gly Ser Gln Gly Ala Gly Gln Gly Gly Tyr Gly Gln Gly
        420                 425                 430

Gly Ala Gly Ala Ser Ser Ala Ala Ala Ser Ala Ala Ala Ser Arg
        435                 440                 445

Leu Ser Ser Ala Ser Ala Ala Ser Arg Val Ser Ser Ala Val Ser Ser
450                 455                 460

Leu Val Ser Ser Gly Gly Pro Thr Asn Ser Ala Ala Leu Ser Ser Thr
465                 470                 475                 480

Ile Ser Asn Val Val Ser Gln Val Ser Ala Ser Asn Pro Gly Leu Ser
                485                 490                 495

Gly Cys Asp Val Leu Val Gln Ala Leu Leu Glu Ile Val Ser Ala Leu
            500                 505                 510

Val His Ile Leu Gly Ser Ser Ser Ile Gly Gln Val Asn Tyr Asn Ala
        515                 520                 525

Ala Gly Gln Ser Ala Ser Val Val Gly Gln Ser Phe Tyr Gln Ala Leu
        530                 535                 540

Ala
545

<210> SEQ ID NO 37
<211> LENGTH: 451
<212> TYPE: PRT
<213> ORGANISM: Parawixia bistriata

<400> SEQUENCE: 37

Gln Gly Pro Gly Ala Gly Gln Gln Gly Pro Gly Ala Gly Gln Gln Gly
1               5                   10                  15

Pro Tyr Gly Pro Ser Ala Ala Ala Ala Ala Ala Ala Gly Gly Tyr
            20                  25                  30

Gly Pro Gly Gly Ala Gln Gln Gly Pro Gly Ala Gly Gln Gln Gly
        35                  40                  45

Pro Gly Ser Gln Gly Gln Ser Gly Pro Gly Ala Thr Val Ala Ala Ala
50                  55                  60

Ala Ala Gly Gly Tyr Gly Pro Gly Gly Ala Gln Gln Gly Pro Gly
65                  70                  75                  80

Ala Gly Gln Gln Gly Gln Gly Ser Gln Gly Pro Tyr Gly Pro Ala Ala
                85                  90                  95

Thr Ala Ala Ala Ala Ala Gly Gly Tyr Gly Pro Gly Ser Gly Gln
            100                 105                 110

Gln Gly Pro Gly Ala Gly Gln Gln Gly Pro Gly Gln Gly Pro Tyr
        115                 120                 125

Gly Pro Ser Ala Ala Ala Ala Ala Ala Ala Gly Gly Tyr Gly Pro
        130                 135                 140

Gly Ser Gly Gln Gln Gly Pro Gly Ala Gly Pro Gln Gly Pro Gly Ser
145                 150                 155                 160

Gln Gly Pro Tyr Gly Pro Gly Ala Ala Ala Ala Ala Val Gly
                165                 170                 175

Gly Tyr Gly Pro Gly Ser Gly Gln Gln Gly Pro Gly Ala Gly Gln Gln
                180                 185                 190

Gly Pro Gly Gly Gln Gly Pro Tyr Gly Pro Ser Ser Ala Ala Ala
            195                 200                 205

Ala Ala Ala Gly Gly Tyr Gly Pro Gly Ala Gly Gln Gln Val Pro
    210                 215                 220

Gly Ala Gly Gln Gln Gly Pro Gly Asn Gln Gly Pro Ser Pro Gly
225                 230                 235                 240

Ala Ala Ala Ala Ala Ala Ala Gly Gly Tyr Gly Pro Gly Gly Ala
                245                 250                 255

Gly Gln Gln Gly Pro Ala Ala Gly Gln Gln Gly Pro Gly Ser Gln Gly
                260                 265                 270

Ser Tyr Gly Pro Gly Ala Ala Ala Ala Ala Ala Gly Gly Tyr
            275                 280                 285

Gly Pro Gly Ser Gly Gln Gln Gly Pro Gly Ala Gly Gln Gln Gly
        290                 295                 300

Pro Gly Gln Gly Pro Tyr Gly Pro Gly Ser Ser Ala Ala Ala
305                 310                 315                 320

Val Gly Gly Tyr Gly Pro Ser Ser Gly Leu Gln Gly Pro Ala Gly Gln
                325                 330                 335

Gly Pro Tyr Gly Pro Gly Ala Ala Ser Ala Ala Ala Ala Gly
            340                 345                 350

Ala Ser Arg Leu Ser Ser Pro Gln Ala Ser Ser Arg Val Ser Ser Ala
                355                 360                 365

Val Ser Ser Leu Val Ser Ser Gly Pro Thr Asn Ser Ala Ala Leu Thr
        370                 375                 380

Asn Thr Ile Ser Ser Val Val Ser Gln Ile Ser Ala Ser Asn Pro Gly
385                 390                 395                 400

Leu Ser Gly Cys Asp Val Leu Ile Gln Ala Leu Leu Glu Ile Val Ser
                405                 410                 415

Ala Leu Val His Ile Leu Gly Tyr Ser Ser Ile Gly Gln Ile Asn Tyr
                420                 425                 430

Asp Ala Ala Gln Tyr Ala Ser Leu Val Gly Gln Ser Val Ala Gln
            435                 440                 445

Ala Leu Ala
    450

<210> SEQ ID NO 38
<211> LENGTH: 234
<212> TYPE: PRT
<213> ORGANISM: Parawixia bistriata

<400> SEQUENCE: 38

Gly Gly Ala Asn Gly Ala Ser Ala Ala Ala Ser Ala Gly Gly Ala
1               5                   10                  15

Gly Gly Tyr Gly Ser Asp Gly Tyr Gly Gln Gly Gly Gln Gly Ala
            20                  25                  30

Gly Gly Asp Gly Ser Ala Ala Ala Ala Ala Ala Ser Gly Gly
        35                  40                  45

Arg Gly Gly Gln Gly Gly Phe Gly Ser Gln Gly Ala Gly Gly Arg Gly
    50                  55                  60

Leu Gly Gly Ser Ala Arg Gly Gly Ala Gly Gly Thr Ser Ala Ala Ala

```
65                  70                  75                  80

Ala Ser Ala Gly Gly Ala Arg Gly Tyr Gly Gly Asp Gly Gly Tyr Gly
                85                  90                  95

Gln Gly Gly Ser Gly Arg Gly Ala Gly Ser Ala Ser Ala Ala Ala
            100                 105                 110

Ala Ser Ala Gly Gly Ala Gly Gly Tyr Gly Gly Asp Gly Gly Tyr Gly
            115                 120                 125

Glu Gly Gly Gln Gly Ala Gly Gly Asp Gly Val Ala Thr Ser Ser Ala
        130                 135                 140

Ala Ser Arg Leu Ser Ser Pro Ser Ser Ile Arg Arg Ile Ser Glu Val
145                 150                 155                 160

Val Ser Thr Phe Ser Asp Asp Phe Gly Asn Ser Ala Ser Phe Ser
                165                 170                 175

Asn Val Tyr Asn Ser Val Ala Ser Gly Ile Thr Ser Ser Asn Pro Gly
            180                 185                 190

Leu Ser Gly Cys Asp Val Gln Ile Gln Thr Leu Leu Glu Met Asn Ser
        195                 200                 205

Ala Leu Leu Ala Leu Leu Tyr Gly Phe Asp Ala Tyr Ser Ser Ala Ala
    210                 215                 220

Leu Val Asn Asp Phe Val Asn Gln Pro His
225                 230

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(8)
<223> OTHER INFORMATION: This sequence may encompass 6-8 residues

<400> SEQUENCE: 39

His His His His His His His His
1               5

<210> SEQ ID NO 40
<211> LENGTH: 626
<212> TYPE: PRT
<213> ORGANISM: Nephila inaurata

<400> SEQUENCE: 40

Ser Gly Gly Ser Gly Gly Thr Thr Val Ile Glu Asp Leu Asp Ile Thr
1               5                   10                  15

Ile Asp Gly Ala Asp Gly Pro Ile Thr Ile Ser Glu Glu Leu Thr Ile
            20                  25                  30

Ser Gly Ala Gly Ala Gly Gly Ser Gly Pro Gly Gly Ala Gly Pro Gly
        35                  40                  45

Gly Val Gly Pro Gly Gly Ser Gly Pro Gly Gly Val Gly Pro Gly Gly
    50                  55                  60

Ser Gly Pro Gly Gly Val Gly Pro Gly Gly Ala Gly Pro Tyr Gly
65                  70                  75                  80

Pro Gly Gly Ser Gly Pro Gly Gly Ala Gly Gly Ala Gly Pro Gly
                85                  90                  95

Gly Ala Tyr Gly Pro Gly Gly Ser Gly Gly Pro Gly Gly Ala Gly Gly
            100                 105                 110
```

-continued

```
Pro Tyr Gly Pro Gly Gly Glu Gly Pro Gly Ala Gly Pro Tyr
            115                 120                 125
Gly Pro Gly Gly Glu Gly Pro Gly Gly Ala Gly Pro Tyr Gly Pro
        130                 135                 140
Gly Gly Ala Gly Gly Pro Tyr Gly Pro Gly Gly Ala Gly Pro Tyr
145                 150                 155                 160
Gly Pro Gly Gly Ala Gly Gly Pro Tyr Gly Pro Gly Gly Ala Gly
                165                 170                 175
Pro Tyr Gly Pro Gly Gly Val Gly Pro Gly Gly Thr Gly Pro Gly
            180                 185                 190
Tyr Gly Pro Gly Gly Ala Gly Pro Gly Gly Tyr Gly Pro Gly Ser
        195                 200                 205
Gly Pro Gly Gly Tyr Gly Pro Gly Gly Ser Gly Pro Gly Gly Tyr
    210                 215                 220
Pro Gly Gly Ser Gly Pro Gly Gly Phe Gly Pro Gly Gly Ser Gly Pro
225                 230                 235                 240
Gly Gly Ser Gly Pro Gly Gly Ser Gly Pro Gly Gly Tyr Gly Pro Gly
                245                 250                 255
Gly Ser Gly Pro Gly Gly Tyr Gly Pro Gly Gly Ser Gly Pro Gly Gly
            260                 265                 270
Tyr Gly Pro Gly Gly Ser Gly Pro Gly Gly Tyr Gly Pro Gly Gly Ser
        275                 280                 285
Gly Pro Gly Gly Ser Gly Pro Gly Gly Tyr Gly Pro Gly Gly Ser Gly
    290                 295                 300
Pro Gly Gly Tyr Gly Pro Gly Gly Ser Gly Pro Gly Gly Ala Gly Pro
305                 310                 315                 320
Gly Gly Ala Gly Pro Gly Gly Val Gly Pro Gly Gly Ala Gly Pro Gly
                325                 330                 335
Gly Ala Gly Pro Gly Gly Val Gly Pro Gly Gly Ala Gly Pro Gly Gly
            340                 345                 350
Ala Gly Pro Gly Gly Ala Gly Pro Gly Gly Ala Gly Arg Gly Gly Ala
        355                 360                 365
Gly Pro Gly Gly Ala Gly Ala Gly Gly Ala Gly Gly Ser Gly Gly
    370                 375                 380
Ala Gly Gly Ser Gly Gly Thr Thr Val Ile Glu Asp Leu Asp Ile Thr
385                 390                 395                 400
Ile Asp Gly Ala Asp Gly Pro Ile Thr Ile Ser Glu Glu Leu Thr Ile
                405                 410                 415
Gly Gly Ala Gly Gly Ser Gly Pro Gly Gly Ala Gly Gly Ser Gly Pro
            420                 425                 430
Gly Gly Ala Gly Pro Gly Gly Val Gly Pro Gly Gly Ser Gly Pro Gly
        435                 440                 445
Gly Leu Gly Ser Gly Gly Ser Gly Pro Gly Gly Val Gly Pro Gly Gly
    450                 455                 460
Ser Gly Pro Gly Gly Val Gly Pro Gly Gly Tyr Gly Pro Gly Gly Ser
465                 470                 475                 480
Gly Gly Leu Tyr Gly Pro Gly Ser Tyr Gly Pro Gly Gly Ser Gly Val
                485                 490                 495
Pro Tyr Gly Ser Ser Gly Thr Tyr Gly Ser Gly Gly Tyr Gly Pro
            500                 505                 510
Gly Gly Ala Gly Gly Ala Tyr Gly Pro Gly Ser Pro Gly Gly Ala Tyr
        515                 520                 525
Gly Pro Gly Ser Gly Gly Ser Tyr Tyr Pro Ser Ser Arg Val Pro Asp
```

-continued

```
                530                   535                   540
Met Val Asn Gly Ile Met Ser Ala Met Gln Gly Ser Gly Phe Asn Tyr
545                 550                 555                 560

Gln Met Phe Gly Asn Met Leu Ser Gln Tyr Ser Ser Gly Ser Gly Ser
                565                 570                 575

Cys Asn Pro Asn Asn Val Asn Val Leu Met Asp Ala Leu Leu Ala Ala
                580                 585                 590

Leu His Cys Leu Ser Asn His Gly Ser Ser Ser Phe Ala Pro Ser Pro
            595                 600                 605

Thr Pro Ala Ala Met Ser Ala Tyr Ser Asn Ser Val Gly Arg Met Phe
            610                 615                 620

Ala Tyr
625
```

PROTEINS FROM THE WEBS OF NEPHILENGYS CRUENTATA, A VICULARIA JURUENSIS AND PARAWIXIA BISTRIATA SPIDERS ISOLATED FROM BRAZILIAN BIODIVERSITY

CROSS-REFERENCE TO RELATED APPLICATION

This application is a continuation of U.S. application Ser. No. 12/531,664, filed Sep. 16, 2009 which is a National Stage entry of International Application No. PCT/BR2008/000072, filed Mar. 13, 2008, which is based upon and claims the benefit of priority of the prior Brazilian Patent Application No. PI 0701826-6, filed Mar. 16, 2007, the disclosure of the prior application is hereby incorporated in its entirety by reference.

FIELD OF THE INVENTION

The present invention relates to molecules isolated from the nucleic acid that encodes proteins related to spider webs, fragments of these or other of they derivates. The invention also refers to a chimerical gene and an expression vector containing molecules isolated from the nucleic acid that encode proteins related to the webs of *Nephilengys cruentata, Avicularia juruensis* and *Parawixia bistriata* spiders. Another embodiment of the present invention are transformed cells containing a gene construct or an expression vector of the present invention.

Yet another embodiment of the present invention relates to a method for obtaining genetically modified organisms containing inventive gene constructs or expression vectors and a method for obtaining recombinant proteins from the silks of *Nephilengys cruentata, Avicularia juruensis* and *Parawixia bistriata* spiders. Finally, the invention describes products, such as biofilaments and compositions, composed from the recombinant proteins of the present invention.

BACKGROUND OF THE INVENTION

Industry has recently demonstrated great interest in obtaining synthetic or natural fibres that simultaneously provide high resistance, low weight, and overall versatility. Most of the synthetic fibres currently used, such as Nylon or Kevlar, present high production costs as well as some other undesirable characteristic such as high density or restricted fields of application.

Amongst the natural fibres, silk provided by the silkworm (*Bombyx mori*) has been used for over 5.000 years in the textile industry (Hyde, N. 1984. The queen of textiles. *Natl. Geogr.* 165, 3-49). The fibres of this egg sac are composed of two continuous filament of silk, heavy-($\approx$350 kDa) and light-chain fibroin ($\approx$25 kDa), linked by adhesive proteins termed sericins (Jin H. J., Kaplan D. L. (2003). Mechanism of silk processing in insects and spiders. Nature 424:1057-1061). Commercially, sericin is removed from the egg sacs by immersion in hot water and soap, which yields between 300 and 1200 m of usable fibre (fibroin) per egg sac.

Different from the silkworm, spiders have not yet been domesticated for textile applications. This basic difference is the result of the difficulty in obtaining large spider populations due to their solitary and predatory nature; furthermore, spider silk is produced in small quantities and cannot be gathered into skeins like simpler fibres, in the manner of the silkworm coccon. However, the physical characteristics presented by the silks produced by spiders are far superior to that of the silk from *B. mori* (Dickinson M. H. (1999). Bionics: Biological insight into mechanical design. *Proc. Natl. Acad. Sci. USA* 96:14208-14209). Due to its great elasticity and resistance, the silk from spider's webs has not only aroused much interest in the textile industry but also in other industries from the most diverse sectors, such as the cosmetic industry (US20050019297).

Spiders are amongst the organisms that present the greatest diversity and abundance on Earth. The order Araneae is the second largest group among the arachnids and the seventh among arthropods, with over 39.000 species included in 110 families (Selden P. A. 1989. Orb-weaving spiders in the early Cretaceous. *Nature,* 340: 711-712; Shear W. A., Palmer J. A., Coddington J. A., Bonamo P. M. 1989. a Devonian Spinneret: early evidence of spiders and silk use. *Science* 246: 479-481; Platnick, N. I. 2006. *The world spider catalog, version* 6.5. American Museum of Natural History). It is estimated that Brazil alone is home to between 4.000 and 10.000 species of spiders [Brescovit, A. D. 1999. Araneae. *In: Biodiversidade do Estado de São Paulo*, Brazil. Joly, C. A. & C. E. M. Bicudo (orgs.). Fundação de Amparo à Pesquisa do Estado de São Paulo, São Paulo, SP].

The fibres obtained from the proteins of spider silks are up to five times more resistant than steel and 30% more flexible than Nylon. They may be used in the manufacture of ropes and cables, fishing lines, bullet-proof vests, parachute materials, amongst other uses. Furthermore, as they are composed of biodegradable matter, spider silks may have medical applications such as in the manufacture of sutures and surgical dressings, bandages, atificial tendons and ligaments, matrix for drug carriers, etc. (WO2004016651; Gosline, J. M.; P. A Guarette; C. S. Ortlepp & K. N. Savage, 1999. The mechanical design of spider silks: from fibroin sequence to mechanical function. *The Journal of Experimental Biology,* 202: 3295-3303; Heslot, 1998. Artificial fibrous proteins: a review. *Biochimie,* 80: 19-31). Silks produced by spiders are synthesised in glands located in the region of the abdomen and polymerised through a series of spinnerts that convert the water soluble silk proteins of high molecular weight into non-water soluble fibres (Benito B., 2002. Synthesizing spider silk. *Trends Biotechnol.* 20:189). The types and nature of fibres are several and they depend on the spider's species [Denny, M. W., 1980. Silks—their properties and functions. *In: Mechanical properties of Biological Materials*. Vincent, J. F. V., Currey, J. D. (Eds.), Cambridge University Press, Cambridge, pp. 247-272]. Spiders possess seven silk producing glands: the aciniform gland responsible for producing the silks used to encapsulate insects, the cylindrical gland that produces the silk forming the egg sac where the eggs are deposited, and the flagelliform, "major ampullate", "minor ampullate", pyriform and coronata glands, that produce the silks that form the orb web. But, however, no known family of spiders possesses all seven glands.

Among the different silks produced by spiders is the dragline synthesised by the "major ampullate" gland which is extremely rigid and has a tensile strength similar to that of Kevlar ($4\times10^9$ N/m$^2$) associated to good viscoelasticity (dragline 35%, Kevlar 5%) (Oroudjev E., Soares J., Arcidiacono S., Thompson J. B., Fossey A. S., Hansma H. G. (2002). Segment nanofibers of spider dragline silk: Atomic force microscopy and single-molecule force spectroscopy. *Proc. Natl. Acad. Sci. USA* 99:6460-6465). The dragline silk is used by spiders to escape from predators and as a frame for the production of silks. The silk produced by the "minor ampullate" gland, used as a reinforcement when building the web, has a tensile strength similar to that of the dragline, but with less elasticity (Colgin M. A., Lewis R. V. 1998. Spider minor ampullate silk proteins contain new repetitive sequences and highly conserved non-silk-like 'spacer regions'. *Protein Sci.* 7:667-672; Hayashi C. Y., Blackledge T. A., Lewis R. V. 2004. Molecular and mechanical characterization of aciniform silk: uniformity of iterated sequence modules in a novel member of the spider silk fibroin gene family. *Mol. Biol. Evol.* 21:1950-1959). Spider silks are biopolymers that present extraordinary physical properties (Cunniff P. M., Fossey S. A., Auerbach M. A., 1994a. Mechanical and thermal properties of dragline silk from the spider *Nephila clavipes*. *Poly. Adv. Technol.* 5:401-410, Cunniff P. M., Fossey S. A., Auerbach M. A., 1994b. Mechanical properties of major ampullate gland silk fibers extracted from *Nephila clavipes* spiders. In: Kaplan, D. L., Adams, W. W., Farmer, B., Viney, C. (Eds.). *Silk Polymers: Materials science and Biotechnology, American Chemical Society Symposium Series,* 544, pp. 234-251; Ko F. K., Jovicic J., 2004. Modelling of mechanical properties and structural design of spider web. *Biomacromolecules* 5:780-785), but there is only limited, knowledge about the composition of the different silks produced by a specific species of spider. The different silk proteins contain repetitive amino acids that vary depending on the purpose of the silk and thus confer different mechanical properties to the biopolymers (Gosline J. M., Guerette P. A., Ortlepp C. S., Savage K. N. (1999). The mechanical design of spider silks: from fibroin sequence to mechanical function. *The J. Exp. Biol.* 202: 3295-3303). Depending on environmental conditions and requirements, the composition of the silk amino acids may vary considerably, not just between different spiders but for the same spider on different days (Work R. W., Young C. T., 1987. The amino acid compositions of major and minor ampullate silks of certain orb-web-building spiders (Araneae, Araneidae). *J. Arachnol.* 15:65-80; Volltrah F. 1999. Biology of spider silk. *Int. J. Biol. Macromol.* 24:81-88; Craig C. L., Riekel C., Herberstein M. E., Weber R. S., Kaplan D., Pierce N. E., 2000. Evidence for diet effects on the composition of silk proteins produced by spiders. *Mol. Biol. Evol.* 17:1904-1913). This fact raises questions concerning the genomic sequences and the organisation of the genes that encode these proteins.

The first studies intending the industrial use of these silks were mainly directed at the protein analysis of two species: *Nephila clavipes* and *Araneus diadematus*. The dragline silk isolated from these two species is the most studied of all the fibres synthesised by spiders. The dragline is formed from two types of proteins produced by the "major ampullate" gland, termed MaSp1 and MaSp 2 (Major Ampullate Spidroin) in *N. clavipes*, and ADF-3 and ADF-4 in *A. diadematus* (*Araneus diadematus* Fibroin) (Hinman M. B., Lewis, R. V. 1992. Isolation of a clone coding a second dragline silk fibroin, *Nephila clavipes* dragline silk is a two protein fiber. *J. Biol. Chem.* 267:19320-19324; Guerette P., Ginzinger D., Weber B., Gosline S. 1996. Silk properties determined by gland-specific expression of a spider fibroin gene family. *Science* 272:112-115; Beckwitt R., Arcidiacono S. 1994. Sequence conservation in the C-terminal region of spider silk proteins (Spidroin) from *Nephila clavipes* (Tetragnathidae) and *Araneus bicentenarius* (Araneidae). *J. Biol. Chem.* 269:6661-6663; Beckwit R., Arcidiacono S., Stote R. 1998. Evolution of repetitive proteins: spider silks from *Nephila clavipes* (Tetragnathidae) and *Araneus bicentarius* (Araneidae). *Insect. Biochem. Molec.* 28:121-130). The dragline proteins have a molecular mass between 180 kDa and 720 kDa, depending on the analysis conditions (Mello C. M., Senecal K. Yeung B., Vouros P., Kaplan D. I. 1994. Initial characterization of *Nephila clavipes* dragline protein. In: Kaplan D. L. Adams W. W Farmer B. Viney C. (Eds.). Silk Polymers Materials Science and Biotechnology. *American Chemical Society Symposium Series.* 544:67-79). The amino acid composition of these proteins tends to indicate that the molecular ratio between MaSp1 and MaSp2, and between ADF-4 and ADF-3 is of approximately 3:1 in the dragline fibre (Hinman M. B., Lewis, R. V. 1992. Isolation of a clone coding a second dragline silk fibroin, *Nephila clavipes* dragline silk is a two protein fiber. *J. Biol. Chem.* 267: 19320-19324; Lombardi S. J., Kaplan D. L. 1990. The amino acid composition of major ampullate gland silk (dragline) of *Nephila clavipes* (Araneae, Tetragnathidae). *J. Arachnol.* 18:297-306; Guerette P., Ginzinger D., Weber B., Gosline J. 1996. Silk properties determined by gland-specific expression of a spider fibroin gene family. *Science* 272:112-115). Despite being produced by two different species, the proteins of the "major ampullate" gland comprise a high number of repetitions of the same amino acids. In MaSp2 and ADF-3, for example, glycine, alanine, proline, serine and tyrosine are responsible for up to 99% of the amino acids present in their structure (Hayashi C. Y., Lewis R. V. 1998. Evidence from flagelliform silk. cDNA for the structural basis of elasticity and modular nature of spider silks. *J. Mol. Biol.* 275:773-784).

Several works have been developed over the characteristics and possible applications for the dragline silk of *Nephila clavipes* [U.S. Pat. Nos. 6,268,169; 6,412,261; WO9116351; Beckwitt R. & Arcidiacono S., 1994. Sequence conservation in the C-terminal region of spider silk proteins (Spidroin) from *Nephila clavipes* (Tetragnathidae) and *Araneus bicentenarius* (Araneidae). *J. Biol. Chem.* 269, 6661-6663; Arcidiacono S., Mello, C., Kaplan D. L., Cheley, S., Bayley, H., 1998. Purification and characterization of recombinant spider silk expressed in *Escherichia coli. Appl. Microbiol. Biotechnol.* 49, 31-38].

Apart from the proteins of the silk produced by the "major ampullate" gland, another frequently studied silk of the *N. clavipes* is that produced by the "minor ampullate" gland. Just as in the case of the silk produced by the former gland, this one is also formed from two peptides (MiSP1 and MiSP2) composed by imperfect repetitions of amino acid sequences (U.S. Pat. No. 5,733,771).

In 1998, Hayashi and Lewis (Hayashi C. Y., Lewis R. V., 1998. Evidence from flagelliform silk. cDNA for the structural basis of elasticity and modular nature of spider silks. *J. Mol. Bio,* 275: 773-784), sequenced the protein of the silk produced by the flagelliform gland of *N. clavipes* (Gosline, J. M.; P. A Guarette; C. S. Ortlepp & K. N. Savage, 1999. The mechanical design of spider silks: from fibroin sequence to mechanical function. *The Journal of Experimental Biology,* 202: 3295-3303). Similar results have been published for the species *Araneus diadematus*, involving the "major ampullate" that produces proteins ADMAG1 and ADMAG2 (Guerette P., Ginzinger D., Weber B., Gosline J., 1996. Silk properties determined by gland-specific expression of a spider fibroin gene family. *Science,* 272:112-115).

Based on DNA analysis, it is possible to affirm that all proteins comprising spider silks are formed by repetitive peptide units. These may be grouped into four major groups: GPGXX (where X frequently represents Q), alanine rich sequences (An or (GA)n), GGX (where X=A, Y, L or Q) and the spacers. A fifth category is represented by non-repetitive regions at the N- and C-terminal ends of the proteins and are normally chains constituted of 100 or more amino acids (Xu M., Lewis R. V., 1990. Structure of a protein superfiber: Spider dragline silk. *Proc. Natl. Acad. Sci. USA* 87:7120-7124; Hinman M. B., Lewis, R. V. 1992. Isolation of a clone coding a second dragline silk fibroin, *Nephila clavipes* dragline silk is a two protein fiber. *J. Biol. Chem.* 267:19320-19324; Colgin M. A., Lewis R. V. 1998. Spider minor ampullate silk proteins contain new repetitive sequences and highly conserved non-silk-like 'spacer regions'. *Protein Sci.* 7:667-672; Hayashi C. C. Y., Shipley N. H., Lewis R. V. 1999. Hypothesis that correlate the sequence, structure and mechanical properties of spider silk proteins. *Int. Biol. Macromol.* 24:271-275; Oroudjev E., Soares J., Arcidiacono S., Thompson J. B., Fossey A. S., Hansma H. G. 2002. Segment nanofibers of spider dragline silk: Atomic force microscopy and single-molecule force spectroscopy. *Proc. Natl. Acad. Sci USA* 99:6460-6465; Tai P. L., Hwang G. Y., Tso I. M., 2004. Inter-specific sequence conservation and intra-individual sequence variation in a spider silk gene. *Inter. J. Biol. Macromolecules* 34:295-301).

In accordance with different studies, the majority of the repetitive units present in spider silks present specific structural properties (Xu M., Lewis R. V., 1990. Structure of a protein superfiber: Spider dragline silk. *Proc. Natl. Acad. Sci. USA* 87:7120-7124; Hayashi C. Y., Lewis R. V. 1998. Evidence from flagelliform silk. cDNA for the structural basis of elasticity and modular nature of spider silks. *J. Mol. Biol* 275:773-784; Van Beek J. D., Hess S., Vollrath F., Meier B. H., 2002. The molecular structure of spider dragline silk: Folding and orientation of the protein backbone. *Proc. Natl. Acad. Sci USA* 99:10266-10271; Bini E., Knight D. P., Kaplan D. L. 2004. Mapping domain structures in silks from insects and spiders related to protein assembly. *J. Mol. Biol.* 335:27-40; Scheibel T. 2004. Spider silks: recombinant synthesis, assembly, spinning, and engineering of synthetic proteins. *Microb. Cell Fact.* 3:14; Stantcheva N. N. P., Mason S. J. M. 2004. Molecular studies of a novel dragline silk from nursery web spider, *Euprosthenops* sp (Psauridae). *Comp. Biochem. Phisiol.* 138:371-376). The GPGXX module is responsible for the formation of the β-spiral structures, and probably confers elasticity to the silk. The flagelliform silk, produced by the flagelliform gland, possesses an elasticity of over 200% and comprises at least 43 GPGXX modules in each repetitive unit (Hayashi C. Y., Lewis R. V. 2000. Molecular architecture and evolution of a modular of spider silk protein gene. *Science* 287:1477-1479). In conformity with the low elasticity of dragline silk, the latter only presents nine repetitions of this motive before being interrupted by another module. Alaninee rich modules are normally constituted of 6-9 residues of this amino acid with these being responsible for the formation of the β-sheets that provide rigidity to the fibre. The silks produced by the "major" and "minor ampullate" glands are both very strong and present An or (GA)n motives but, however, these motives are not encountered in flagelliform silks (Gatesy J., Hayashi C., Motriuk D., Woods J., Lewis R. 2001. Extreme diversity, conservation, and convergence of spider silk fibroin sequences. *Science* 291:2603-2605). In turn, GGX, which is a 310 helix, forms an amorphous matrix that connects the crystalline regions and confers elasticity to the fibre, probably in conjunction with GPGXX. This motive may be encountered in all the flagelliform, "major" and "minor ampullate" glands. The spacer regions are constituted of charged groups that separate the glycine rich regions (Colgin M. A., Lewis R. V. 1998. Spider minor ampullate silk proteins contain new repetitive sequences and highly conserved non-silk-like 'spacer regions'. *Protein Sci.* 7:667-672; Hayashi C. C. Y., Shipley N. H., Lewis R. V. 1999. Hypothesis that correlate the sequence, structure and mechanical properties of spider silk proteins. *Int. Biol. Macromol.* 24:271-275) but, however, its structural purpose remains unknown. The non-repetitive terminations are common in all the fibres produced by spiders of the Araneidae family, with the C-terminal sequences being highly conserved among the species (Bini E., Knight D. P., Kaplan D. L. 2004. Mapping domain structures in silks from insects and spiders related to protein assembly. J. Mol. Biol. 335: 27-40; Hayashi C. Y., Blackledge T. A., Lewis R. V. 2004. Molecular and mechanical characterization of aciniform silk: uniformity of iterated sequence modules in a novel member of the spider silk fibroin gene family. *Mol. Biol. Evol.* 21:1950-1959; Stantcheva N. N. P., Mason S. J. M. 2004. Molecular studies of a novel dragline silk from nursery web spider, *Euprosthenops* sp (Psauridae). *Comp. Biochem. Phisiol.* 138:371-376; Tian M., Liu C., Lewis R., 2004. Analysis of major ampullate silk cDNA from two non-orb-weaving spiders. *Biomacromolecules* 5:657-660). Recent studies conducted with ADF-3 and 4 revealed an α-helix structure formed by the C-terminal region, which raises the hypothesis that this region has an important role in the polymerisation of the fibre (Huemmerich D., Scheibel T., Vollrath F., Cohen S., Gat U., Ittah I. 2004. Novel assembly properties of recombinant spider dragline silk proteins. *Curr. Biol.* 14:472-476).

The spinning mechanism, or, in other terms, the polymerisation of water soluble proteins into insoluble fibres, is a process that commences with an increase in the concentration of the protein in the glandular lumen forming a "spinning solution". In the major ampullate gland, for example, the proteins of dragline silk are present in a concentration over 50% (m/v) (Artkins E. 2003. Silk's secrets. *Nature* 424:1010; Scheibel T. 2004. Spider silks: recombinant synthesis, assembly, spinning, and engineering of synthetic proteins. *Microb. Cell Fact.* 3:14). The increased concentration of MaSp causes a structural modification to these proteins, which change from a coil to a β-helix structure and increase their stability (Dicko C., Knight D., Kenney J. M., Vollrath F. 2004. Structural conformation of spidroin in solution: A synchrotron radiation circular dichroism study. *Biomacromolecules* 5:758-767). In this manner, the spider maintains a relatively high concentration of protein in an aqueous solution, without leading to the formation of insoluble β-sheets. The polymerisation of the proteins occurs when the "spinning solution" passes through the glandular duct, concommitantly with the extraction of water, sodium and chloride. Hydrogen and potassium ions are secreted which reduces the pH from 6.9 to 6.3 (Chen X., Knight D. P., Shao Z., Vollrath F. 2002. Conformation transition in silk protein films monitored by time-resolved fourier transform infrared spectroscopy: Effect of potassium ions on *Nephila spidroin* films. *Biochemistry* 41:14944-14950; Dicko C., Vollrath F., Kenney J. M. 2004. Spider silk protein refolding is controlled by changing pH. *Biomacromolecules* 5:704-710). Such alterations trigger the alignment of the proteins in the distal part of the duct and while their poly-A hydrophobic sequences align and come closer they are exposed to an increasingly hydrophobic environment which most probably instigates the structural conversion of these proteins to β-sheets (Scheibel T. 2004. Spider silks: recombinant synthesis, assembly, spinning, and engineering of synthetic proteins. *Microb. Cell Fact.* 3:14), and, consequently, the polymerisation of the fibre.

The high organisation of the fibre structures, extensive hydrogen bonds and Van der Walls interactions induce the expulsion of water from the regions between the β-sheets. Spider silks are insoluble in water, dilute acids and bases, chaotropic agents such as urea and guanidine hydrochloride as well as the majority of organic solvents (Lombardi S. J., Kaplan D. L. 1990. The amino acid composition of major ampullate gland silk (dragline) of *Nephila clavipes* (Araneae, Tetragnathidae). *J. Arachnol.* 18:297-306). The silks are also resistant to the majority of proteolytic enzymes. The silks dissolved slightly in saline solutions of lithium bromide, lithium thiocyanate, calcium chloride and other calcium salts. High concentrations of a propionic/hydrochloridric acid mixture as well as formic acid may also be used (Mello C. M., Senecal K. Yeung B., Vouros P., Kaplan D. I. 1994. Initial characterization of *Nephila clavipes* dragline protein. In: Kaplan D. L. Adams W. W Farmer B. Viney C. (Eds.). Silk Polymers: Materials Science and Biotechnology. *American Chemical Society Symposium Series.* 544:67-79 Lewis R. V., Hinman M., Kothakota S., Fournier M. J. 1996. Expression and purification of a spider silk proteins: A new strategy for producing repetitive proteins. *Express. Prif* 4:400-406).

Different parties have attempted to process the silk artificially using different types of diluents. Most efforts have centred around the liquid processing used for *B. mori*. Silk recombinant proteins have been processed using solvents such as hexafluoroisopropanol (WO 9429450) as diluents or protein solutions diluted in concentrated solutions of formic acid [Lewis R. V., Hinman M., Kothakota S., Fournier M. J., 1996. Expression and purification of a spider silk protein: A new strategy for producing repetitive proteins. *Express. Prif* (4): 400-406]. However, in both above cases the mechanical properties of natural silk were not efficiently reproduced. (Fahnestock S. R., Bedzyk L. A, 1997. Production of synthetic spider dragline silk protein in *Pichia pastoris. Appl. Microbiol. Biotechnol,* 47: 23-32).

Other essays succeeded in solubilising the spider silks through immersion of the fibres in saline concentrations such as lithium bromide, lithium thiocyanate, calcium chloride and other calcium salts. High concentrations of a propionic/hydrochloridric acid mixture as well as formic acid may also be used [Mello C. M., Senecal K., Yeung B., Vouros P., Kaplan D. I., 1994. Initial characterization of *Nephila clavipes* dragline protein. In: Silk Polymers: Materials Science and Biotechnology. *American Chemical Society Symposium Series.* Kaplan D. L., Adams W. W, Farmer B., Viney C. (Eds.), 544 pp].

Initially, the process that leads to the high hydrophobicity of the spider silk proteins triggers the formation of repetitive crystalline sequences. In silkworm, the process is accompanied by changes in physiological conditions such as pH and salt concentrations in the glands and presumably help to maintain solubility. The physical break generated during the spinning process of the soluble silk seems to be, in large part, responsible for the conversion of the soluble protein into the insoluble fibre in the natural processing sequence. [Ilzuka, E., 1985. Silk: an overview. *J. Appl. Polymer. Sci. Jpn.* 41: 163-171; Ilzuka, E., 1985. Silk thread: Mechanism of spinning and its mechanical properties. *J. Appl. Polymer Sci Jpn.* 41: 173-185; Magoshi J., Magoshi Y., Nakamura S., 1985. Crystallization, liquid crystal, and fiber formation of silk fibroin. *J. Appl. Polymer Sci.* 41: 187-204; Magoshi J., Magoshi Y., Nakamura S., 1994. Mechanism of fiber formation of silkworm. In: Silk Polymers: materials Science and Biotechnology, *American Chemical Society Symposium Series*, Kaplan D. L., Adams W. W., Farmer B., Viney C. (Eds.), 544 pp].

The large scale production of spider silk fibres would enable the production of a new generation of biomaterials with high rates of biodegradability that would have practical applications in diverse fields of the industrial sector. The inability to domesticate spiders in order to produce sufficient quantities of proteins for their adequate study and commercial use has induced the development of studies to make the production of silk proteins viable through large scale heterologous expression systems. Recent sucesses cloning cDNAs and synthetic genes and the expression of spider silk recombinant proteins in different systems have been vital to developing a better understanding of the structure, processing and purpose of these proteins, and of their important mechanical properties (Kaplan D. L., Adams W. W., Farmer B., Viney C. 1994. Silk Polymers: Materials Science and Biotechnology. *American Chemical Society Symposium Series* Volume 544; Kaplan D. L., Mello C. M., Arcidiacono S., Fossey S., Senecal K., Muller W., 1998. Silk. In: McGrath, K., Kaplan. D. L. (Eds.), *Protein Based Materials*. Birkhauser, Boston).

Studies are presently underway to increase available knowledge concerning these processes. However, the highly repetitive nature of these genes, the specific codons used by the spiders and the uncommon secondary structure adopted by the mRNA results in an inefficient translation of the proteins and limits the size of the fibre capable of being produced (Fahnestock S. R., Bedzyk L. A. 1997. Production of synthetic spider dragline silk protein in *Pichia pastoris. Appl. Microbiol. Biotechnol.* 47:23-32; Scheibel T. 2004. Spider silks: recombinant synthesis, assembly, spinning, and engineering of synthetic proteins. *Microb. Cell Fact.* 3:14). Due to the repetitive feature of the sequences, initial research performed on mRNAs collected from the "major ampullate" gland of *N. clavipes* were not successfully translated in vitro (Candelas G. C., Cintron J. J. 1981. A spider fibroin and its synthesis. *J. Exp. Zool.* 216:1-6; Candelas G. C., Lopez, F. 1983. Synthesis of fibroin in the cultured glands of *Nephila clavipes. Comp. Biochem. Physiol.* 74:637-641; Candelas G. C., Candelas T., Ortiz A., Rodriguez O. 1983. Translation pauses during a spider fibroin synthesis. *Biochem. Biophys. Res. Commun.* 116:1033-1038).

Different heterologous expression systems are being used in the attempt to produce spider fibres. Recent studies using constructs made from partial cDNAs of the dragline genes produced recombinant proteins in *E. coli* (Arcidiacono S., Mello, C., Kaplan D. L., Cheley, S., Bayley, H. 1998. Purification and characterization of recombinant spider silk expressed in *Escherichia coli. Appl. Microbiol. Biotechnol.* 49:31-38), in MAC-T (bovine) and MK (hamster) cell cultures (Lazaris A., Arcidiacono S., Huang Y., Zhou J. F, Duguay F., Chretien N., Welsh E. A., Soares J. W., Karatzas C. N. 2002. Spider silk fibers spun from soluble recombinant silk produced in mammalian cells. *Science* 295:472-476), and in cell lines of the *Spodoptera frugiperda* insect using the baculovirus expression system (Huemmerich D., Scheibel T., Vollrath F., Cohen S., Gat U., Ittah I. 2004. Novel assembly properties of recombinant spider dragline silk proteins. *Curr. Biol.* 14:472-476). Several studies used constructs containing cDNA of genes that encode proteins of the "minor ampullate" and flagelliform glands of spiders, such as in the case of patent documents U.S. Pat. No. 576,677 and U.S. Pat. No. 5,994,099. Document U.S. Pat. No. 5,728,810 describes the expression of Spidroin sequences 1 and 2 of *N. clavipes* in microorganisms. Documents U.S. Pat. No. 6,608, 242, US20050010035 and WO0194393 report a method for producing synthetic proteins of spider silks in plants and constructs expressing synthetic proteins of the silk derived from *Nephila clavipes* and other species of spiders. The documents of patent CN1380418 describe the synthetic construct of spider web "Spidroin" protein for expression in cotton plants. Studies have shown the expression of spider silks proteins in animals, as in the case of patent documents WO9947661 and US2001042255, that describe methods for the recombinant production of biofilaments in the milk and/or urine of transgenic animals.

Synthetic genes based on the MaSp sequence of *N. clavipes* and *Araneus gemmoides* have also been used for the expression of heterologous proteins in *E. coli* (Fahnestock S. R., Bedzyk L. A. 1997. Production of synthetic spider dragline silk protein *Pichia pastoris*. *Appl. Microbiol. Biotechnol.* 47:23-32), *Pichia Pastoris* (Fahnestock S. R., Bedzyk L. A. 1997. Production of synthetic spider dragline silk protein in *Pichia pastoris*. *Appl. Microbiol. Biotechnol.* 47:23-32) and plants (US20040210956; Scheller J., Gurhuns K. H., Grosse F., Conrad U. 2001. Production of spider silk proteins in tobacco and potato. *Nat. Biotechnol.* 19:573-577; Piruzian E. S., Bogush, V. G., Sidoruk K. V., Goldenkova I. V., Mysiychuk K. A., Debabov V. G. 2003. Construction of synthetic genes for analogues of spider silk spidroin 1 and their expression in Tabacco plants. *Mol. Biol.* 27:554-560; Scheller J., Henggeler D., Viviani A., Conrad U. 2004. Purification of spider-elastin from transgenic plants and application for human chondrocyte proliferation. *Transg. Res.* 13:51-57). Unfortunately, no MaSp gene has been completely cloned as yet and the data available refers to partial cDNA clones initiated by the 3' termini of the dragline silk genes of *N. clavipes, A. diadematus* and other species (Xu M., Lewis R. V., 1990. Structure of a protein superfiber: Spider dragline silk. *Proc. Natl. Acad. Sci. USA* 87:7120-7124; Hinman M. B., Lewis, R. V. 1992. Isolation of a clone coding a second dragline silk fibroin, *Nephila clavipes* dragline silk is a two protein fiber. *J. Biol. Chem.* 267:19320-19324; Beckwitt R., Arcidiacono S. 1994. Sequence conservation in the C-terminal region of spider silk proteins (Spidroin) from *Nephila clavipes* (Tetragnathidae) and *Araneus bicentenarius* (Araneidae). *J. Biol. Chem.* 269:6661-6663 Guerette P., Ginzinger D., Weber B., Gosline J. 1996. Silk properties determined by gland-specific expression of a spider fibroin gene family. *Science* 272:112-115 Hayashi C. Y., Lewis R. V. 1998. Evidence from flagelliform silk. cDNA for the structural basis of elasticity and modular nature of spider silks. *J. Mol. Biol.* 275:773-784). An explanation for such results may be the possible degradation of the mRNA during its extraction from the silk producing glands when constructing cDNA libraries since the longer mRNAs are more sensitive to enzymatic degradation (Stantcheva N. N. P., Mason S. J. M. 2004. Molecular studies of a novel dragline silk from nursery web spider, *Euprosthenops* sp (Psauridae). *Comp. Biochem. Phisiol.* 138:371-376). The production of spider silk proteins in heterologous systems and the manipulation of the primary structures of these proteins using modular structure engineering has been based on the available knowledge of natural spider silks (Cappello J., Crissman J., Dorman M. 1990. Genetic engineering of structural protein polymers. *Biotech. Prog.* 6:198-202; Scheibel T. 2004. Spider silks: recombinant synthesis, assembly, spinning, and engineering of synthetic proteins. *Microb. Cell Fact.* 3:14; Kang W. J., Cho S. S., Huh H., Chung D. T 1997. Identification of dynamic behavior of sheet metals for an auto-body with tension split Hopkinson bar. *Trans.* KSME 21:2209-2219; Kang W. J., Cho S. S., Huh H., Chung D. T. 1999. Modified Johnson-Cook model for dynamic behaviour of sheet metals for auto-body Crash-worthiness. *Int. J. Vehicle Design,* 21:424-435).

The possibility of producing proteins from spider silks in heterologous systems on a large scale with the intended kinetics and functions shall allow their application in numerous medical products such as dressings and suture microfilaments for neurosurgery. These high-performance fibres could have diverse technical and industrial applications. The silks may be used in ropes and special fishing nets, parachutes, ballistic applications (bullet-proof vests, etc.) sporting products, textile industries, cosmetic industry and as a low-weight raw material for aerospace construction. An additional benefit would be the use of spider silk proteins in the manufacture of microbiocides and defensins against diseases and pests in the areas of agriculture, livestock and human health.

There is therefore a need for identifying new spider silk proteins, expressing them in different systems and developing other methods that afford solutions to the existing problems in the area described above.

The present invention describes new spider silk proteins extracted from the *Nephilengys cruentata, Avicularia juruensis* and *Parawixia bistriata* as well as the expression of these proteins in recombinant systems. The present invention further describes the expression of the silk proteins in plant, animal and fibre producing microorganism cells in order to produce new fibrous biomaterials with enhanced characteristics.

SUMMARY OF THE INVENTION

The discovery of new spider silk proteins, as well as their characterisation and expression in different heterologous systems shall be of great use in numerous fields, such as the medical and industrial sectors.

The proteins from spider silks may be obtained through synthetic polypeptides having amino acid sequences substantially similar to a consensus sequence of the silk protein or through polypeptides expressed from nucleic acid sequences coding a protein of a natural or engineered silk, or derivates of these. Depending on the application for which the silk protein is required, it may be useful to form fibres from a single spider web protein or from a combination of different spider web proteins.

One aspect of the invention provides isolated molecules of spider nucleic acid characterised by comprising:
 a) sequences substantially similar to any of the sequences selected from the group identified as SEQ ID N. 1-19;
 b) complements of the sequences described in SEQ ID N. 1-19;
 c) reverse complements of the sequences described in SEQ ID N. 1-19;
 d) reverse sequences of the sequences described in SEQ ID N. 1-19;

A second aspect of the invention provides a chimerical gene characterised by comprising:
 a) a promoter optionally linked to a leader sequence and operationally linked to;
 b) a coding sequence substantially similar to any of the sequences identified as SEQ ID N. 1-19.

Another aspect of the present invention provides an expression vector characterised by comprising:
 a) a promoter optionally linked to a leader sequence and operationally linked to;
 b) a coding sequence substantially similar to any of the sequences identified as SEQ ID N. 1-19 operationally linked to;
 c) a termination signal;
 d) an origin of replication;
 e) a selective marker; and
 f) a cloning site.

A fourth embodiment of the present invention relates to molecules isolated from the spider silk protein characterised by comprising sequences substantially similar to any of the sequences selected from the group identified as SEQ ID N. 20-38.

Yet another aspect of the invention provides host cells comprising at least one of the spider silk proteins encoded by nucleic acids. These host cells include, but are not limited to, bacterial cells, fungus cells, insect cells, mammal cells and plant cells. Host cells over expressing one ore more spider silk proteins encoded by the nucleic acid of the present invention provide useful reagents for diverse purposes including, but not limited to, the production of silk fibres comprising at least one silk protein that may be incorporated within a material to modulate the structural properties of that material.

The present invention also describes a method for producing a genetically modified organism characterised by the fact of comprising the following steps:
 a) transforming a cell, tissue, organ or embryo with a chimerical gene in accordance with any of the claims 3 to 11 or an expression vector in accordance with any of the claims 12 to 23;
 b) selecting transformed cells, cell calluses, embryos or seeds;
 c) regenerating mature plants, mature embryos or microorganisms of the transformed cells, cell calluses, embryos or seeds selected in stage (b);
 d) selecting the mature plants, mature embryos or microorganisms cells of stage (c) containing the chimerical gene or expression vector with the nucleotide sequences that encode the spider silk protein.

The present invention also describes a method for the production of recombinant spider silk proteins in prokaryote and eukaryote cells characterised by the fact of comprising the following steps:
 a) transforming a cell, tissue, organ or embryo with an expression vector in accordance with any of the claims 12 to 23;
 b) selecting transformed cells, callus cells, embryos or seeds;
 c) regenerating mature plants, mature embryos or microorganisms having transformed cells, callus cells, embryos or seeds selected in stage (b);
 d) selecting the mature plants, mature embryos or microorganisms cells of stage (c) containing the expression vector with the nucleotide sequences that encode the spider silk protein;
 e) extracting the recombinant spider silk protein produced in the organisms selected in stage (d).

The invention also includes recombinant proteins having microbicide, defensin and dermatological activity, as well as dermatological compositions for pharmaceutical use and microbicide compositions for agricultural use.

The invention further relates a dermatological composition characterised by the fact of comprising:
 a) A recombinant protein in accordance with claim 42;
 b) A pharmaceutically acceptable vehicle.

The invention also describes a microbicide composition characterised by the fact of comprising:
 a) A recombinant protein in accordance with claim 43;
 b) An agriculturally acceptable vehicle and, optionally,
 c) Additives.

Lastly, the invention describes biopolymers produced from the recombinant proteins of the present invention.

DETAILED DESCRIPTION OF THE INVENTION

Figure 1:
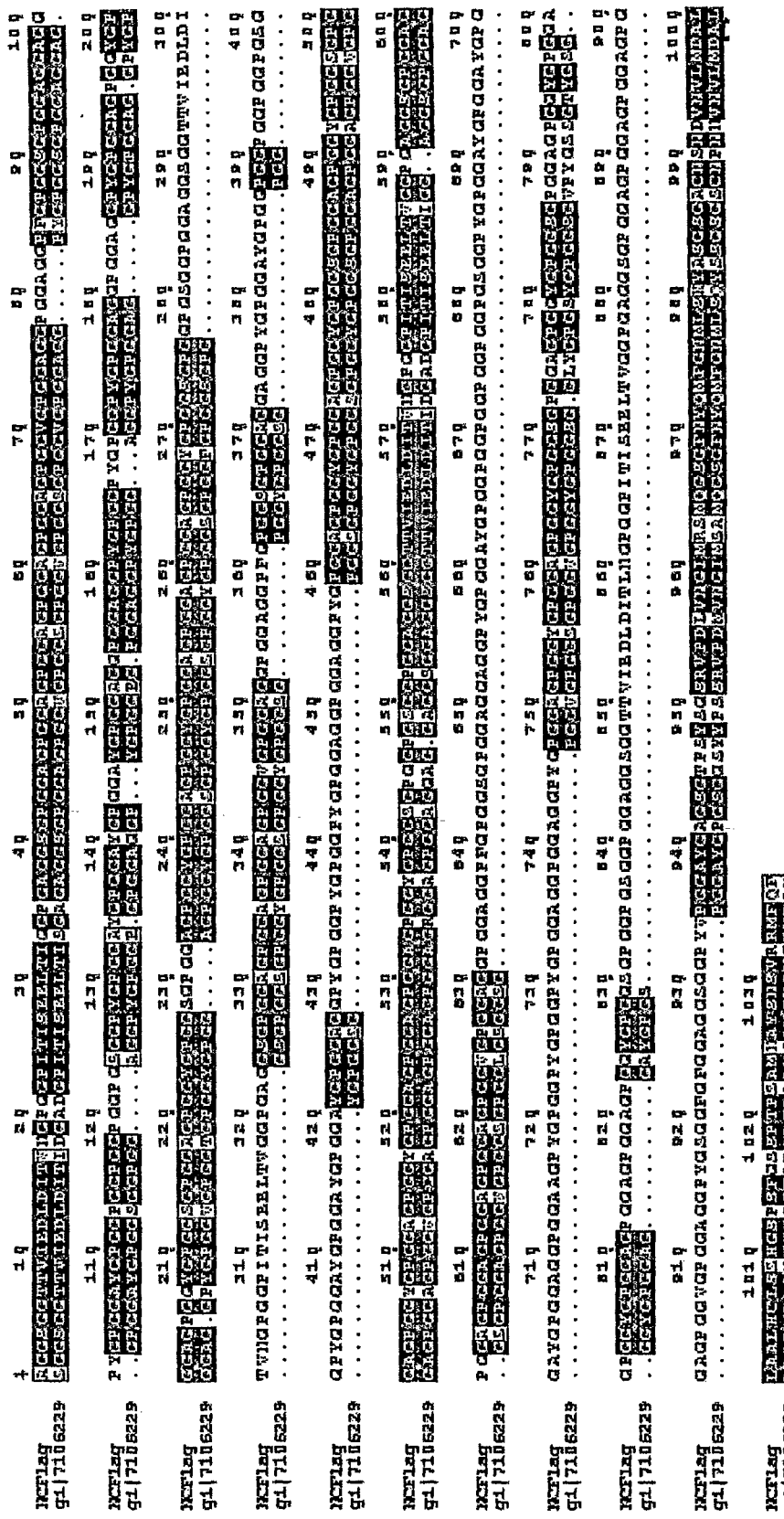
FIG. 1—Alignment between SEQ ID N. 1 and gi|7106229. The sequences inserted in the rectangles with a dark background highlight the amino acids identical to both sequences. The numbers over the sequence identify the position in the alignment and do not correspond to the position in either sequence. The difference is due to the insertion of gaps to maintain alignment.

The following definitions are provided for better understanding the present invention:

The term "isolated nucleic acid molecule" is used in reference to the nucleic acids of the present invention. This term, when applied to DNA, refers to the DNA molecule that is separate from the directly contiguous sequences (in directions 5' and 3') that occur naturally in the genome of the organism from which they were derived. For example, an "isolated nucleic acid molecule" may be inserted in a vector, such as a plasmid or a virus vector, or incorporated within the genomic DNA of a prokaryote or eukaryote. An "isolated nucleic acid molecule" may also comprise a cDNA molecule. An isolated nucleic acid molecule inserted in a vector is also sometimes referred to herein as a recombinant nucleic acid molecule. The term "isolated nucleic acid molecule" may also be applied to RNA molecules transcribed from an isolated DNA molecule as described above. Alternatively, the term may also refer to a RNA molecule that has been sufficiently separated from the RNA molecules to which it was formerly associated in its natural state (i.e. in cells or tissues).

The definition of the terms "complement", "reverse complement" and "reverse sequence" as used herein may be illustrated by the following example: for the sequence 5'AGTGAAGT3', the complement is 3'TCACTTCA5', the reverse complement is 3'ACTTCACT5' and the reverse sequence is 5'TGAAGTGA3'.

"Coding sequence" refers to the DNA sequence that encodes a specific protein and excludes the non-coding sequence. An "interrupted coding sequence" means a sequence that acts as a separator (e.g. one or more introns linked by junctions). An "intron" is the sequence of a nucleotide that is transcribed and is present in the pre-mRNA but is subsequently removed by cleavage and re-linking of the mRNA within the cell which generates a mature mRNA that may be translated into a protein. Examples of introns include, but are not limited to, intron pdk2, castor oil catalase intron, Delta 12 cotton desaturase intron, Delta 12 *Arabidopsis* desaturase, maize ubiquitin intron, SV40 intron, malate synthase gene introns.

A "gene construct" is a gene comprising a promoter and an coding region of different origins. In the case of the present invention, the gene construct comprises the polynucleotides of the present invention linked either in an isolated or associated form to expression regulating regions, such as promoters and termination signals.

The methods for obtaining gene constructs comprising promoters linked to nucleic acids is known in the state-of-the-art and may be found in Sambrook, et al. (Molecular Cloning, A Laboratory Manual, 2nd ed. (1989), Cold Spring Harbor Laboratory Press).

The term "vector" refers to a replicon, such as a plasmid, cosmid, BAC, phage or virus, in which other genetic sequences or elements (whether DNA or RNA) may be linked to be replicated together with the vector. Preferentially the virus derived vector is selected from the bacteriophage, vaccinia, retrovirus or the bovine papillomavirus. An "expression vector" is a specialized vector that contains a gene with the regulatory regions necessary for the expression of a host cell. Such vectors may be obtained commercially, including Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). Some examples of the vectors used in the present invention are, but are not limited to, pMAC/PS, pCMV-Gal and pGFP/NEO. The term "operationally linked" means that the regulatory sequences necessary for the expression of the coding sequence are placed in the DNA molecule in appropriate positions in relation to the coding sequence for the purpose of its expression. This same definition is sometimes applied to the arrangements of the coding sequences and transcription controlling elements (e.g. promoters, enhancers and termination elements) in the expression vector. An exogenous coding region is typically flanked by operationally linked regulatory regions that regulate the expression of the exogenous coding region in a transformed cell (which may be microorganism, plant or animal). A typical regulatory region operationally linked to an exogenous coding region includes a promoter, as such, a fragment of nucleic acid that may cause transcription of the exogenous coding regions, positioned in the 5' region of the exogenous coding region. The present invention is not limited to the use of any particular promoter and a broad variety of promoters are known in the state-of-the-art. These promoters may be, but are not limited to, inducible, constitutive and tissue-specific. Preferentially, the promoter of the present invention is selected from the group of promoters for the cotton fibre genes and may be, but are not limited to, E6, H6S, Rac13, LTP, ACP, expansin, CAP, anexin, FbL2A and actin 2.

In one of the aspects of the invention, the promoter is a constitutive promoter. In another aspect of the invention, promoter activity is stimulated by external factors such as, but without being limited to, hormones, chemical compositions, mechanical impulses, and biotic or abiotic stress conditions. Promoter activity may also be regulated in a temporal and spatial manner (such as, for example, tissue-specific promoters and promoters regulated during development).

The promoter may contain "enhancer" elements. An "enhancer" is a DNA sequence capable of stimulating promoter activity. It can be an element innate to the promoter or a heterologous element inserted to increase the promoter's tissue-specificity and/or intensity. "Constitutive promoters" refer to those promoters that direct genic expression to all tissues in a constant manner. "Tissue-specific promoters" or "development-specific promoters" are those that direct genic expression almost entirely to specific tissues, such as leaves, roots, stems, flowers, fruits or seeds, or only during specific stages of development of a tissue, such as at the beginning or end of embryogenesis.

In one of the aspects of the invention, the promoter is a promoter expressed in plants. As used herein, the term "promoter expressed in plants" means a DNA sequence capable of initiating and/or controlling transcription in a plant cell. This includes any promoter of plant origin; Any promoter of non-plant origin capable of directing expression in a plant cell, for example, promoters of viral or bacterial origin such as 19S and 35S of CaMV (such as mentioned in patent application US20030175783, Hapster et al, 1988 *Mol. Gen. Genet.* 212, 182-190), bacteriophage promoter T7 and gene promoters present in T-DNA of *Agrobaterium*; tissue-specific or organ-specific promoters including, but not limited to, seed-specific promoters (WO8903887), primary organ specific promoters (such as those mentioned in patent application US20030175783, An et al., 1996 The Plant Cell 8, 15-30), stem specific promoters (such as those mentioned in patent application US20030175783, Keller et al., 1988 *EMBO J.* 7: 3625-3633), leaf specific promoters (such as those mentioned in patent application US20030175783, Hudspeth et al., 1989 *Plant Mol Biol* 12:579-589), mesophyll specific promoters, root specific promoters (such as those mentioned in patent application US20030175783, Keller et al., 1989 *Genes Devel.* 3:1639-1646), tubercle specific promoters (such as those mentioned in patent application US20030175783, Keil et al., 1989 *EMBO J.* 8: 1323:1330), vascular tissue specific promoters (such as those mentioned in patent application US20030175783, Peleman et al., 1989 Gene 84: 359-369), stamen specific promoters (WO8910396, WO9213956), dehiscence specific promoters (WO9713865); and the similar. Apart from the specific promoters, other endogenous plant promoters exist. These include, but are not limited to, the promoter of the small subunit of ribulose 1.6 biphosphate (RUBP), beta-conglycinin promoter, beta-phaseolin promoter, γ-kafirin promoter, beta-amylase, maize alcohol dehydrogenase, cruciferine (seed-specific), rubisco, RD2 tobacco gene, SAG *Arabidopsis* gene (leaves), polygalacturonase (fruit), patatin (tubercles), barley hordein, napin, rice actin, maize ubiquitin promoter, ADH promoter, GPAL2 promoter, GPAL3 promoter and thermal shock protein promoters, amongst others. The expression of silk in fibre-producing plants such as cotton, sisal, rush, palm, jute, cane, bamboo, agave and hemp, amongst others, may use the beta-tubulin, A1, A2, A4 and MYB (MYB-like transcription factor) cellulose synthetase gene promoters, amongst others (U.S. Pat. No. 6,608,242). The invention preferentially includes cotton fibre gene promoters that include, but are not limited to, the E6, H6S, Rac13, LTP, ACP, expansin, CAP, anexin, FbL2A and actin 2 gene promoters.

In one of the aspects of the invention, the promoter is a promoter expressed in animals. As used herein, the term "promoter expressed in animals" means a DNA sequence capable of initiating and/or controlling transcription in an animal cell. This includes any promoter of animal origin and any promoter of non-animal origin capable of directing expression in an animal cell, for example, the milk beta-casein promoter (Invitrogen). The preferred promoters used in the invention direct the transcription of a protein in milk producing cells, such as, but not limited to, the promoters of the following genes: whey acid protein (WAP), alpha casein S1, alpha casein S2, beta casein, kappa casein, beta lactoglobulin, alpha lactalbumin, amongst others. Further preferred promoters of the invention direct the transcription of a protein in urine producing cells (e.g. a uroepithelial cell or a cell of the same nature); such promoters include, but are not limited to, the uroplakin gene promoter. Yet other preferred promoters of the invention direct transcription of a protein in an embryo cell.

Apart from the promoters described above, one of the embodiments of the present invention refers to the promoters expressed in bacteria, fungus and insects. As used herein, the term "promoter expressed in bacteria" means a DNA sequence capable of initiating and/or controlling transcription in a bacterial cell. As used herein, the term "promoter expressed in fungus" means a DNA sequence capable of initiating and/or controlling transcription in a fungal cell. As used herein, the term "promoter expressed in insects" means a DNA sequence capable of initiating and/or controlling transcription in an insect cell.

A "leader sequence" or "signal sequence" in the present invention means a sequence of nucleic acid that, when operationally linked to a molecule of nucleic acid, allows the secretion of the product of the nucleic acid molecule. The leader sequence is preferentially located in the 5' region of the nucleic acid molecule. Preferentially, the leader sequence is obtained from the same gene than the promoter used to direct the transcription of the nucleic acid molecule, or is obtained from the same gene from which the nucleic acid molecule was derived. Preferentially, the present invention uses the signal sequence of α-coixin.

The transcription termination signal and the polyadenylation region of the present invention includes, but is not limited to, the SV40 termination signal, the HSV TK adenylation signal, the termination signal of the nopaline synthetase gene (NOS) of *Agrobacterium tumefaciens*, the octopine synthetase gene termination signal, the termination signal of the 19S and 35S genes of CaMV, the maize alcohol dehydrogenase gene termination signal, the manopine synthetase gene termination signal, the beta-phaseolin gene termination signal, the ssRUBISCO gene termination signal, the sucrose synthetase gene termination signal, the termination signal of the virus that attacks the *Trifolium subterranean* (SCSV), the termination signal of the trpC gene of *Aspergillus nidulans*, and other similars.

As described above, the term "expression vectors" may comprise an inducible promoter operationally linked to a nucleic acid sequence encoding a spider web protein. "Inducible" promoters may direct the expression the expression of a polynucleotide with which they are operationally linked, in a tissue or specific stage of development or in response to environmental conditions. In one of the aspects of the invention, expression vectors comprise a strongly regulated inducible vector operationally linked to a nucleic acid molecule coding a spider web protein. This expression vector may further comprise a selection marker gene (e.g. a gene coding a protein that confers resistance to antibiotics) operationally linked to a constitutive promoter or a strongly regulated inducible promoter. Depending on the purpose, it may benefit the expression of a nucleic acid sequence coding a spider web protein through a pathogen inducible promoter. These promoters include those promoters derived from proteins related to pathogenesis (PR proteins) which are induced through infections by a pathogen, such as, for example, PR proteins, SAR proteins, beta glucanase 1.3, chitinase, etc. In an aspect of the present invention, it may be advantageous to use promoters that are expressed locally or close to the infection site of the pathogen. Furthermore, since many pathogens enter plants through wounds that are often the result of insect damage, a wounding inducible promoter may be included amongst the expression vectors of the invention. Wound inducible promoters include, but are not limited to, the potato proteinase inhibitor gene (pinII) promoter, win 1 and win 2 gene promoters, systemine gene promoter, MPI gene promoter.

The transcriptional activity of inducible promoters may also be regulated by various environmental factors including, but not limited to, temperature, anaerobic stress and light. Examples of inducible promoters include the Adh1 promoter (induced by hypoxia or cold stress), Hsp70 promoter (induced by heat stress) and PPDK promoter (induced by light).

As used herein, the term "variant" or "substantially similar" comprises sequences of amino acids or nucleotides different from the specifically identified sequences, in which one or more nucleotides or amino acid residues are deleted, substituted or added. The variants may be allelic variants occurring naturally or variants of non-natural origin. The variant or substantially similar sequences refer to fragments of nucleic acids or peptides that may be characterized by the percentage of the identity of their nucleotide or amino acid sequences with the nucleotide (SEQ ID Ns 1-19) or amino acid (SEQ ID Ns 20-38) sequences described herein, as determined by common algorithms used in the state-of-the-art. The preferred fragments of nucleic acids or peptides are those having a sequence of nucleotides or amino acids with at least around 40 or 45% of sequence identity, preferentially around 50% or 55% of sequence identity, more preferentially around 60% or 65% of sequence identity, more preferentially around 70% or 75% of sequence identity, more preferentially around 80% or 85% of sequence identity, yet more preferentially around 90%, 91%, 92%, 93%, 94%, 95%, 96%, 97%, 98% or 99% of sequence identity when compared to the sequence of reference. The percentage of identity is determined by the alignment of the two sequences to be compared, ascertaining the number of identical residues in the aligned portion, dividing this number by the total number of residues in the sequence being assessed and multiplying the result by 100. This alignment may be done using software tools in the public domain, one of which is BLASTN, available at the National Center for Biotechnology Information/NCBI (www.ncbi.nlm.nih.gov) homepage. The sequence alignment and identity percentage calculation of the present invention have been performed and the sequences deposited in the Gene Bank, through integration of the web browser.

The term "specifically hybridizing" refers to the association between two molecules of single chain nucleic acid possessing sufficiently complementary sequences to allow such hybridization under pre-determined conditions generally described in the state-of-the-art (sometimes referred to as "substantially complementary" in the present invention). More particularly, the term refers to the hybridisation of an oligonucleotide with a substantially complementary sequence containing a molecule of single chain DNA or RNA of the present invention. The appropriate conditions necessary to enable the specific hybridisation between single chain nucleic acid molecules of variable complementariness are well described in the state-of-the-art. The following formula is commonly used for calculating the required conditions of stringency for hybridisation between nucleic acid molecules to occur (Sambrook et al., Molecular Cloning, A Laboratory Manual, 2nd ed. (1989), Cold Spring Harbor Laboratory Press):

$$Tm=81.5° C.+16.6 \log [Na+]+0.41(\% G+C)-0.63(\% \text{formamide})-600/pb \text{ in duplex (probe)}$$

As can be seen by the above formula, using [Na+]=[0.368] and 50% formamide, with a GC content of 42% and an average probe size of 200 bases, the Tm shall be 57° C.

The term "oligonucleotide" refers herein to 'primers' and 'probes' of the present invention, and is defined as a nucleic acid molecule comprising one or more ribo- or deoxyribonucleotides, preferentially more than three. The exact size of the oligonucleotides shall depend on various factors as well as the particular application and use of the oligonucleotides. The preferred oligonucleotides comprise 15-50 consecutive bases.

The term "probe" when used in the present invention refers to an oligonucleotide, polynucleotide or nucleic acid, being RNA or DNA, when occurring naturally such as in the digestion of a purified or synthetically produced restriction enzyme and that is capable of either annealing or specifically hybridizing with a nucleic acid containing complementary sequences of the probe. A probe may further be single or double chain. The exact length of the probe will depend on numerous factors, including temperature, the probe's origin and use of the method. For example, depending on the complexity of the target sequence, the oligonucleotide probe may typically contain 15-25 or more nucleotides, although it might actually contain less nucleotides. The probes herein are selected so as to be complementary in order to discern the chains of a particular nucleic acid sequence. This means that the probe may be sufficiently complementary to be capable of "specifically hybridising" or annealing with its respective target-chains under a series of pre-determined conditions. Consequently, the probe sequence does not necessarily exactly reflect the target complementary sequence. For example, a non-complementary nucleotide fragment may be linked to the 5' or 3' extremity of the probe, with the remaining sequence of the probe being complementary to the target chain. Alternatively, non-complementary bases or long sequences may be interspersed within the probe provided the latter is sufficiently complementary with the target nucleic acid sequence to anneal specifically with it.

The term "primer" as used herein refers to an oligonucleotide, being RNA or DNA, single or double chain, derived from a biological system and generated by the digestion of a purified or synthetically produced restriction enzyme that, when placed in an appropriate environment, is capable of functionally acting as the initiator of a template-dependent nucleic acid synthase. When in the presence of an appropriate nucleic acid template, suitable nucleoside triphosphates precursors for nucleic acids, a polymerase enzyme, adequate cofactors and conditions such as temperature and suitable pH values, the primer may extend at its 3' terminal by the addition of nucleotides through the action of polymerase or some similar activity to produce a first extension of the product. The 'primer' may vary in length depending on particular conditions and application requirements. For example, for diagnostic applications, the oligonucleotide 'primer' typically contains 15-25 or more nucleotides in length. The 'primer' must sufficiently complementary with the intended template to initiate the extension synthase of the intended product. This does not mean that the 'primer' must represent the intended template exactly. For example, a non-complementary nucleotide sequence may be linked to the 5' extremity of a complementary 'primer'. Alternatively, non-complementary bases or long sequences may be interspersed within the oligonucleotide sequence of the 'primer' provided the latter is sufficiently complementary with the intended template sequence to functionally provide a template-primer for the extension synthase of the product. The description of the primers used in the present invention can be found in the section of the examples where these primers are required (e.g. PCR reactions).

The term "isolated protein" or "isolated and purified protein" is occasionally used in the present invention. This term refers to a protein produced by the expression of an isolated nucleic acid molecule of the present invention. Alternatively, this term may refer to a protein that has been sufficiently separated from other proteins to which it may be naturally associated, such as when existing in its "substantially pure" form. The term "isolated" does not exclude synthetic or artificial mixtures with other compounds or materials, or the presence of impurities that do not interfere with the fundamental activity of that protein. These may be present, for example, following incomplete purification or the addition of stabilisers, and also combined within immunogenic preparations or pharmaceutically acceptable preparations. Pharmaceutically acceptable preparations may be used in the production of fibres and synthetic polymers, for example, and may be incorporated to numerous medical implements, including, but not being limited to, sutures, wound dressings and implants.

The term "pharmaceutically acceptable vehicle" refers to solutions in which a spider web protein or a nucleic acid coding sequence of a spider web protein may be maintained without any alteration to the functional properties of the spider web molecule described herein for pharmaceutical purposes. For administration to mammals, for example, a spider web protein or a nucleic acid coding sequence of a spider web protein may be suspended in any pharmaceutically acceptable vehicle, such as, for example, the "HEPES" saline buffer with an approximate pH of 7.8. Other useful pharmaceutically acceptable vehicles include, but are not limited to, glycerol, water, saline solution, ethane and other pharmaceutically acceptable saline solutions such as phosphates and organic acid salts. Examples of these and other pharmaceutically acceptable vehicles are described in Remington's Pharmaceutical Sciences (1991, Mack Publication Co., New Jersey).

The term "agriculturally acceptable vehicle" refers to solutions in which a spider web protein or a nucleic acid coding sequence of a spider web protein may be maintained without any alteration to the functional properties of the spider web molecule described herein for agricultural purposes. The vehicles used for the present invention may be liquids or solids. The liquid vehicles that may be used to form compositions using the recombinant protein of the present invention may be, but are not limited to, water or organic solvents, such as polyalcohols, esters, methylene chloride, alcohol or plant oils. Other components that may be incorporated to the formulation include humectants, preservatives, thickeners, antimicrobial agents, antioxidants, emulsifiers, film forming polymers and mixtures of these. The humectants may include polyalcohols, sugars (such as molasses) glycols and hygroscopic salts. Vitreous membranes and film forming polymers include rosin gum, latex, polyvinylpyrrolidone, polyvinyl alcohol, polyvinyl chloride, polyethylene, polyvinyl acetate and mixtures of these. Further optional additives include methyl, methacrylate and mixtures of these.

The term "mature protein" or "mature polypeptide" mean a polypeptide possessing an amino acid sequence after any processing event that normally occurs to the polypeptide during its generation, such as the proteolytic processing of a polyprotein precursor. When designating the sequence or limits of a mature protein, the first amino acid of the mature protein's sequence is designated as amino acid residue 1. In the case of the present invention, any amino acid residue associated to a mature protein not naturally encountered in association to the protein preceding amino acid 1 are designated amino acid-1, -2, -3, etc. In the case of recombinant expression systems, the methionine initiator codon is frequently used when intending efficient translation. As used herein, this methionine residue in the resulting polypeptide must be in the −1 position of the sequence of the mature protein.

The term "peptidic analogue" means a natural or mutant analogue of a protein, comprising a series of linear or discontinuous fragments of that protein and which may have one or more amino acids replaced with other amino acid(s). It may also have its biological activity altered, enhanced or diminished compared to the parent or non-mutant protein.

The term "biological activity" refers to a function or group of functions performed by a molecule in a biological context (i.e. in an organism or in vitro substitute or some similar model). In the case of spider web proteins, biological activity is characterised by their physical properties (e.g. tensile strength and elasticity) as described herein.

The term "substantially pure" refers to preparations comprising at least 50-60% of the weight of the component of interest (e.g. nucleic acid, oligonucleotide, polypeptide, protein, etc.). More preferentially, the preparation comprises at least 75% of the weight, and yet more preferentially, 90-99% of the weight of the component of interest. Purity shall be measured by methods appropriate to the component of interest (e.g. chromatography methods, HPLC analysis, mass spectrometry and the similar).

The term "vector" refers to a replicon, such as a plasmid, cosmid, bacmid, phagus or virus, in which other genetic sequences or elements (whether DNA or RNA) may be linked to be replicated together with the vector. Preferentially the virus derived vector is selected from the bacteriophages, vaccinias, retrovirus or bovine papillomavirus. An "expression vector" is a specialized vector that contains a gene with the regulatory regions necessary for the expression of a host cell. Such vectors may be obtained commercially, including Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). Some examples of the vectors used in the present invention are, but are not limited to, pMAC/PS, pCMV-Gal and pGFP/NEO. The term "operationally linked" means that the regulatory sequences necessary for the expression of the coding sequence are placed in the DNA molecule in appropriate positions in relation to the coding sequence for the purpose of its expression. This same definition is sometimes applied to the arrangements of the coding sequences and transcription controlling elements (e.g. promoters, enhancers and termination elements) in the expression vector. An exogenous coding region is typically flanked by operationally linked regulatory regions that regulate the expression of the exogenous coding region in a transformed cell (which may be microorganism, plant or animal). A typical regulatory region operationally linked to an exogenous coding region includes a promoter, as such, a fragment of nucleic acid that may cause transcription of the exogenous coding regions, positioned in the 5' region of the exogenous coding region. The present invention is not limited to the use of any particular promoter and a broad variety of promoters are known in the state-of-the-art. These promoters may be, but are not limited to, inducible, constitutive and tissue-specific.

In one aspect of the invention, the promoter is a constitutive promoter. In another aspect of the invention, promoter activity is stimulated by external factors such as, but without being limited to, hormones, chemical compositions, mechanical impulses, and biotic or abiotic stress conditions. Promoter activity may also be regulated in a temporal and spatial manner (such as, for example, tissue-specific promoters and promoters regulated during development).

The promoter may contain "enhancer" elements. An "enhancer" is a DNA sequence capable of stimulating promoter activity. It can be an element innate to the promoter or a heterologous element inserted to increase the promoter's tissue-specificity and/or intensity. "Constitutive promoters" refer to those promoters that direct gene expression to all tissues in a constant manner. "Tissue-specific promoters" or "development-specific promoters" are those that direct gene expression almost entirely to specific tissues, such as leaves, roots, stems, flowers, fruits or seeds, or only during specific stages of development of a tissue, such as at the beginning or end of embryogenesis.

In one of the aspects of the invention, the promoter is a promoter expressed in plants. As used herein, the term "promoter expressed in plants" means a DNA sequence capable of initiating and/or controlling transcription in a plant cell. This includes any promoter of plant origin and any promoter of non-plant origin capable of direction expression in a plant cell, for example, promoters of viral or bacterial origin such as 19S and 35S of CaMV (such as mentioned in patent application US20030175783, Hapster et al, 1988 *Mol. Gen. Genet.* 212, 182-190), bacteriophage promoter T7 and gene promoters present in T-DNA of *Agrobaterium*; tissue-specific or organ-specific promoters including, but not limited to, seed-specific promoters (WO8903887), primary organ specific promoters (such as those mentioned in patent application US20030175783, An et al., 1996 The Plant Cell 8, 15-30), stem specific promoters (such as those mentioned in patent application US20030175783, Keller et al., 1988 *EMBO J.* 7: 3625-3633), leaf specific promoters (such as those mentioned in patent application US20030175783, Hudspeth et al., 1989 *Plant Mol Biol* 12:579-589), mesophyll specific promoters, root specific promoters (such as those mentioned in patent application US20030175783, Keller et al., 1989 *Genes Devel.* 3:1639-1646), tubercle specific promoters (such as those mentioned in patent application US20030175783, Keil et al., 1989 *EMBO J.* 8: 1323:1330), vascular tissue specific promoters (such as those mentioned in patent application US20030175783, Peleman et al., 1989 Gene 84: 359-369), stamen specific promoters (WO8910396, WO9213956), dehiscence specific promoters (WO9713865); and the similar. Apart from the specific promoters, other endogenous plant promoters exist. These include, but are not limited to, the promoter of the small subunit of ribulose 1.6 biphosphate (RUBP), beta-conglycinin promoter, beta-phaseolin promoter, γ-kafirin promoter, beta-amylase, maize alcohol dehydrogenase, cruciferine (seed-specific), rubisco, RD2 tobacco gene, SAG *Arabidopsis* gene (leaves), polygalacturonase (fruit), patatin (tubercules), barley hordein, napin, rice actin, maize ubiquitin promoter, ADH promoter, GPAL2 promoter, GPAL3 promoter and thermal shock protein promoters, amongst others. The expression of silk in fibre-producing plants such as cotton, sisal, rush, palm, jute, cane, bamboo, agave and hemp, amongst others, may use the beta-tubulin, A1, A2, A4 and MYB (MYB-like transcription factor) cellulose synthetase gen promoters, amongst others (U.S. Pat. No. 6,608, 242). The invention preferentially includes cotton fibre gene promoters that include, but are not limited to, the E6, H6S, Rac13, LTP, ACP, expansin, CAP, anexin, FbL2A and actin 2 gene promoters.

In one of the aspects of the invention, the promoter is a promoter expressed in animals. As used herein, the term "promoter expressed in animals" means a DNA sequence capable of initiating and/or controlling transcription in an animal cell. This includes any promoter of animal origin and any promoter of non-animal origin capable of directing expression in an animal cell, for example, the milk beta-casein promoter (Invitrogen). The preferred promoters used in the invention direct the transcription of a protein in milk producing cells, such as, but not limited to, the promoters of the following genes: whey acid protein (WAP), alpha casein S1, alpha casein S2, beta casein, kappa casein, beta lactoglobulin, alpha lactalbumin, amongst others. Further preferred promoters of the invention direct the transcription of a protein in urine producing cells (e.g. a uroepithelial cell or a cell of the same nature); such promoters include, but are not limited to, the uroplakin gene promoter. Yet other preferred promoters of the invention direct transcription of a protein in an embryo cell.

Apart from the promoters described above, one of the embodiments of the present invention refers to the promoters expressed in bacteria, fungus and insects. As used herein, the term "promoter expressed in bacteria" means a DNA sequence capable of initiating and/or controlling transcription in a bacterial cell. As used herein, the term "promoter expressed in fungus" means a DNA sequence capable of initiating and/or controlling transcription in a fungal cell. As used herein, the term "promoter expressed in insects" means a DNA sequence capable of initiating and/or controlling transcription in an insect cell. A "leader sequence" or "signal sequence" in the present invention means a sequence of nucleic acid that, when operationally linked to a molecule of nucleic acid, allows the secretion of the product of the nucleic acid molecule. The leader sequence is preferentially located in the 5' region of the nucleic acid molecule. Preferentially, the leader sequence is obtained from the same gene than the promoter used to direct the transcription of the nucleic acid molecule, or is obtained from the same gene from which the nucleic acid molecule was derived. Preferentially, the present invention uses the signal sequence of α-coixin.

The transcription termination signal and the polyadenylation region of the present invention includes, but is not limited to, the SV40 termination signal, the HSV TK adenylation signal, the termination signal of the nopalin synthetase gene (NOS) of *Agrobacterium tumefaciens*, the octopin synthetase gene termination signal, the termination signal of the 19S and 35S genes of CaMV, the maize dehydrogenase alcohol gene termination signal, the manopine synthetase gene termination signal, the beta-phaseolin gene termination signal, the ssRUBISCO gene termination signal, the sucrose synthetase gene termination signal, the termination signal of the virus that attacks the *Trifolium subterranean* (SCSV), the termination signal of the trpC gene of *Aspergillus nidulans*, and other similar.

As described above, the term "expression vectors" may comprise an inducible promoter operationally linked to a nucleic acid sequence coding a spider web protein. "Inducible" promoters may direct the expression the expression of a polynucleotide with which they are operationally linked, in a tissue or specific stage of development or in response to environmental conditions. In one of the aspects of the invention, expression vectors comprise a strongly regulated inducible vector operationally linked to a nucleic acid molecule coding a spider web protein. This expression vector may further comprise a selection marker gene (e.g. a gene coding a protein that confers resistance to antibiotics) operationally linked to a constitutive promoter or a strongly regulated inducible promoter. Depending on the purpose, it may benefit the expression of a nucleic acid sequence coding a spider web protein through a pathogen inducible promoter. These promoters include those promoters derived from proteins related to pathogenesis (PR proteins) which are induced through infections by a pathogen, such as, for example, PR proteins, SAR proteins, beta glucanase 1.3, chitinase, etc. In an aspect of the present invention, it may be advantageous to use promoters that are expressed locally or close to the infection site of the pathogen. Furthermore, since many pathogens enter plants through wounds that are often the result of insect damage, a wound inducible promoter may be included amongst the expression vectors of the invention. Wound inducible promoters include, but are not limited to, the potato proteinase inhibitor gene (pinII) promoter, win 1 and win 2 gene promoters, systemine gene promoter, MN gene promoter.

The transcriptional activity of inducible promoters may also be regulated by various environmental factors including, but not limited to, temperature, anaerobic stress and light. Examples of inducible promoters include the Adh1 promoter (induced by hypoxia or cold stress), Hsp70 promoter (induced by heat stress) and PPDK promoter (induced by light).

The construction of vectors comprising promoters linked to nucleic acids is known in the state-of-the-art and may be found in Sambrook, et al. (Molecular Cloning, A Laboratory Manual, 2nd ed. (1989), Cold Spring Harbor Laboratory Press).

Expression vectors comprising spider web protein coding nucleic acid sequences are included in the scope of the present invention. The following are also included in the present invention: plant cells, recombinant seeds, recombinant plant embryos, recombinant plants, animal cells, recombinant animal embryos, recombinant animals, insect cells, recombinant insects and recombinant microorganisms comprising expression vectors coding the spider web proteins described herein.

A "transfected cell" or a "transformed cell" means a cell in which a molecule of the nucleic acid coding a polypeptide of the present invention has been inserted using recombinant DNA techniques. The cells may be from a host organism that include, but are not limited to, bacterial cells, fungus cells, insect cells, plant cells and animal cells. Preferentially, the cell is a eukaryote cell of a multicellular organism (e.g. plants and animals).

The expression vectors may be inserted into the genome of the intended host plant by a variety of conventional techniques. For example, they may be introduced directly into the genomic DNA of the plant cell using techniques such as electroporation and the microinjection of plant cell protoplasts or, otherwise, the expression vector may be directly introduced to the plant tissue using ballistic methods, such as the bombardment of DNA-coated particles.

Micro-injection techniques are known in the state-of-the-art and well described in scientific and patent literature. The introduction of expression vectors using polyethylene glycol precipitations is described by Paszkowski et al. *Embo J.* 3:2717-2722, 1984 (as mentioned in patent application US20020152501). The techniques of electroporation are described by From et al. *Proc. Natl. Acad. Sci. USA* 82:5824, 1985 (as mentioned in patent application US20020152501). Ballistic transformation techniques are described by Klein et al. *Nature* 327:70-73, 1987 (as mentioned in patent application US20020152501).

Alternatively, the expression vectors containing the recombinant nucleic acid molecule may be combined to appropriate T-DNA flanker regions and introduced in the conventional host vector *Agrobacterium tumefaciens*. The virulence function of the *Agrobacterium tumefaciens* host will direct the insertion of the recombinant nucleic acid molecules and the adjacent marker inside the DNA of the plant cell when this cell is infected by the bacteria. Transformation techniques mediated by *Agrobacterium tumefaciens*, including disarmament and the use of binary vectors, are well described in scientific literature (as mentioned in patent application US 20020152501, Horsch et al. *Science* 233:496-498, 1984; and Fraley et al. *Proc. Natl. Acad. Sci. USA* 80:4803, 1983).

The cells of transformed plants that are derived through any of the transformation techniques described above may be cultivated to regenerate an entire plant possessing a transformed genotype and thus the intended phenotype for the production of spider web proteins. These regeneration techniques rely on the manipulation of certain phytohormones in tissue culture growth medium and typically containing a biocide and/or herbicide marker that must be introduced together with the intended sequence of nucleotides. Preferentially, the present invention uses selective markers chosen from the antibiotic and herbicide resistant genes such as kanamycin, neomycin, ampicillin, chloranphenicol, streptomycin, hygromycin, geneticin, phosphinotrycin, glyphosate, gluphosinate ammonium, amongst others. The present invention also uses reporter genes to assess the transformation potential of the genes, such as AHAS, BAR and GUS. Regeneration of plants from protoplast cultures is described by Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985 (as mentioned in patent application US20020152501). Regeneration may also be obtained from the callus of plants, explants, organs, or parts of these. Such regeneration techniques are described overall by Klee et al., *Ann. Ver. of Plant Phys.* 38:467-486, 1987 1985 (as mentioned in patent application US20020152501) and may also be found in Clark, 1997 (Clark, M. S. eds., 1997. Plant Molecular Biology A laboratory Manual. Springer-Verlag, Berlin, Heidelberg); Maliga et al., 1995 (Maliga, P.; D. F. Flessing, A. R. Cashmore, W. Cruissem, J. E. Varner, eds., 1995. Methods in Plant Molecular Biology, A Laboratory Course Manual. Cold Spring Harbor Laboratory Press) and Martinez-Zapater & Salinas, 1998 (Martinez-Zapater, J. M. & J. Salinas, eds., 1998. Methods in Molecular Biology, v. 82: *Arabidopsis* Protocols. Humana Press, Totowa, N.J.).

The methodology for the maintenance and growth of microorganism cultures (bacteria, fungus, yeasts) is known to those versed in the matter. The description of such techniques may also be found in related technical manuals such as those by Gerhardt et al., 1994 (Gerhardt, P.; R. G. E. Murray; R. N. Costilow; E. W. Nester; W. A. Wood; N. R. Krieg & G. B. Phillips eds. Manual of Methods for General Bacteriology. *American Society for Microbiology*, Washington, D.C.) or Brock, 1989 (Brock, T. D. 1989. Biotechnology: A Textbook of Industrial Microbiology. Second edition, Sinauer Associates, Inc., Sunderland, Mass.).

An "embryonary cell" means a cell capable of being progenitor to all the cells of the somatic and germinative line of an organism. Examples of embryonary cells include trunk cells (ES cells) and fertilised ovocytes. Preferentially, the embryo cells of the invention are embryo cells of mammals.

"Germinative cell line" means a progenitor eukaryote cell, or the similar of a progenitor cell, that is the product of a meiotic cell division.

A "clone" or a "clonal cell population" is a population of cells derived from a simple cell or common ancestry through mitosis.

A "cell line" is a clone of a primary cell or cell population capable of stable in vitro growth for many generations.

"Plants" refers to photosynthetic organisms, both eukaryote or prokaryote, whereby the term "developed plants" refers specifically to eukaryote plants. The nucleic acid of the invention may be used to confer desirable traits to basically any plant. Thus, the invention is useful to various species of plants, including species of the genera *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna*, and *Zea*.

"Animals" refers to eukaryote organisms that may either belong to the phyla of vertebrates or invertebrates, whereby the term "superior animals" refers to the phyla of vertebrate animals. The nucleic acid of the invention may be used to confer desirable traits to basically any animal. Thus, the invention is useful to various species of vertebrate animals, including species of mammals that include, but are not limited to, primates, cetaceans, insectivores, dermopters, chiropters, rodents, lagomorphs, carnivores, perssodactyls, hyracoid, proboscides, artiodactyls, xenarthrans, folidotes, tubulidentatas, sirenias, marsupials and monotremates. Preferentially, the present invention concerns the use of the nucleic acids of the present invention in the species of mammals that include, but are not limited to the groups Afrotheria, Euarchontoglires, Laurasiatheria and Xenarthra. Preferentially, the present invention concerns the mammals selected among mice, bovines, ovines, caprines and equines.

The term "inferior animals" refers to the phyla of invertebrate animals. The invention is useful to various species of invertebrate animals, including species of arachnids that include, but are not limited to, Acari, Amblypygi, Araneae, Opiliones, Palpigradi, Pseudoscorpiones, Ricinulei, Scorpiones, Solifugae, Uropygi. Preferentially, the present invention concerns the use of the nucleic acids of the present invention in the species of spiders that include, but are not limited to the groups Araneomorphae, Mesothelae and Mygalomorphae.

"Microorganisms" refers to microscopic organisms such as bacteria, viruses, fungus and protozoa. Preferentially, the microorganisms of the present invention include the organisms selected from the bacteria and fungus groups. "Bacteria" refers to prokaryote organisms, with exception the cyanophyta. The nucleic acid of the invention may be used to confer desirable traits to basically any bacteria. Thus, the invention is useful to various species of bacteria that include, but are not limited to, the groups Actinobacteria, Aquificae, Bacteroidetes/group Chlorobi, Chlamydiae/group Verrucomicrobia, Chloroflexi, Chrysiogenetes, Cyanobacteria, Gloeobacteria, Nostocales, Oscillatoriales, Pleurocapsales, Prochlorales, Stigonematales, Deferribacteres, Deinococcus-Thermus, Dictyoglomi, Fibrobacteres/group Acidobacteria, Firmicutes, Fusobacteria, Gemmatimonadetes, Nitrospirae, Planctomycetes, Proteobacteria, Spirochaetes, Thermodesulfobacteria and Thermotogae. "Fungus" refers to organisms of the Fungi kingdom, that may either be unicellular or multicellular. The nucleic acid of the invention may be used to confer desirable traits to basically any fungus. Thus, the invention is useful to various species of funguses that include, but are not limited to, the groups Ascomycota and Basidiomycota. Preferentially, the present invention uses the species of microorganisms selected from the genus *Aspergillus, Bacillus, Escherichia, Pichia, Saccharomyces* or *Streptomyces*.

An "immune response" means any reaction occurring in response to an antigen, such as a viral antigen, in a host having a functional immune system. Immune responses may be humoral "in nature" (i.e. involving the production of immunoglobulins or antibodies) or cellular "in nature" that involve various types of "B" and "T" lymphocytes, dendritic and macrophage cells, antigen-bearing cells and the similar, or both types of responses. The immune response may also involve the production or generation of several effector molecules such as cytokines, lymphokines and the similar. Immune responses may be assessed in vitro or in animal cells and systems. These immune responses may be important to protect the host against diseases and may be used prophylactically and therapeutically.

A "derivate" of a spider web protein or fragment thereof means a polypeptide modified by a variation in the amino acid sequence of the protein (e.g. through the manipulation of the nucleic acids coding the protein or by an alteration to the protein itself). Such derivations of the natural amino acid sequence may involve the insertion, addition, deletion or substitution of one or more amino acids and may or not alter the essential activity of the spider web protein.

The term "native or natural spider web protein" refers to those proteins that are present in the webs produced by spiders. These proteins may be derived from the web itself through dissolution or from the specific web silk gland located in the abdomen of the spider before the silk is spun. The term may also be applied to spider web proteins produced using a variety of expression systems but which substantially comprise the same amino acid sequence as that produced by the spider.

The term "synthetic spider web protein" refers to a protein produced by an expression system having a sequence that may be based on the natural spider web protein sequence or an artificially produced nucleic acid sequence that encodes amino acid motives of spider web proteins.

The term "biofilament" means a fibrous protein that is normally produced and secreted by any of a variety of insects and arachnids. Biofilaments are composed of alternate crystalline and amorphous regions. Examples of biofilaments include spider webs, an externally woven fibrous protein secretion found in numerous arachnids (e.g. *Nephilengys cruentata, Avicularia juruensis* and *Parawixia bistriata*), and fibroin, an externally spun fibrous protein secretion found in a variety of insects (e.g. *Bombyx mori*). Preferably, when the biofilament is secreted in the form of a secretion subject to spinnert action and mechanical extension, it will have a polyalanine segment forming a crystal domain that undergoes a transition from helix to beta-sheet thus forming a (beta) crystal that stabilises this structure. Preferentially, the biofilament's amorphous domain forms a beta-type sheet where the spaces between the sheets are between 3 Ångströms and 8 Ångströms, and preferentially between 3.5 Ångströms and 7.5 Ångströms.

Preferentially, the biofilament has a C-terminal portion with a repeated amino acid motive being between 20 to 40 amino acids in length, more preferentially, being between 34 amino acids in length, and a consensus sequence between 35 to 55 amino acids in length, more preferentially, being between 47 amino acids in length. Preferentially, the biofilament has a repeated amino acid motive (creating both the amorphous and crystalline domains) having a sequence at least 50% identical to the sequences selected from the group SEQ ID N. 19-34), more preferentially, at least 70% identical, and yet more preferentially, at least 90% identical, to the sequences identified as SEQ ID N. 19-34). "Culture medium" means a medium that surrounds the cell and is responsible for its survival. If the cell is secreting a protein (e.g. a biofilament), the cell's culture medium shall contain the protein secreted by this cell.

The discovery of new spider silk proteins, as well as their characterisation and expression in different heterologous systems shall be of great use in numerous areas, such as medicine and industry.

Spider silks proteins may be obtained through synthetic polypeptides having amino acid sequences substantially similar to a consensus unit of the silk protein or through polypeptides expressed from nucleic acid sequences coding a natural or engineered silk protein, or derivates of these. Depending on the application for which the silk protein is required, it may be useful to form fibres from a single spider web protein or from a combination of different spider web proteins.

One aspect of the invention provides nucleic acid sequences coding new spider web proteins. The nucleic acid sequences of the present invention comprise SEQ ID Ns. 1-19.

One particular aspect of the invention provides nucleic acid sequences coding silk proteins principally related, but not limited to the Major Ampullate gland. Examples of the nucleic acid sequences related to this gland comprise SEQ ID Ns. 3, 17 and 18.

One particular aspect of the invention provides nucleic acid sequences coding silk proteins principally related, but not limited to the Minor Ampullate gland. Examples of the nucleic acid sequences related to this gland comprise SEQ ID Ns. 4, 5, 6 and 16.

One particular aspect of the invention provides nucleic acid sequences coding silk proteins principally related, but not limited to the Flagelliform gland. Examples of the nucleic acid sequences related to this gland comprise SEQ ID Ns. 1 and 15.

One particular aspect of the invention provides nucleic acid sequences coding silk proteins principally related, but not limited to the Tubuliform gland. An example of a nucleic acid sequence related to this gland comprises SEQ ID N. 2.

One particular aspect of the invention provides nucleic acid sequences coding silk proteins principally related, but not limited to the Aciniform gland. An example of a nucleic acid sequence related to this gland comprises SEQ ID N. 14.

The nucleic acid molecules coding polypeptides of the present invention may be prepared through two overall methods: either the artificial synthesis of nucleotides that encode the spider web protein or through the isolation of nucleotides originating from the spiders themselves. Both methods use protocols well described in the state-of-the-art. The information from the nucleotide sequence, such as the DNA sequences coding a synthetic or natural spider web protein, may be prepared from an isolated nucleic acid molecule of the invention through the synthesis of the oligonucleotide. The synthesis of oligonucleotides may be prepared by the phosphoramide method used by the DNA Synthesizer of Applied Biosystems 38A or similar equipment. The resulting construct may be used directly or purified in accordance with methods commonly used in the state-of-the-art, such as liquid chromatography (HPLC).

In accordance with the present invention, nucleic acids having appropriate sequence homology rates with the sequences coding a spider web protein may be identified through hybridization conditions and appropriate stringency wash. Such methods are useful for numerous purposes, including the triage of libraries comprising mutant sequences of nucleic acid coding a spider web protein. Hybridisations may be performed according to the methodologies described in Sambrook, et al. (Molecular Cloning, A Laboratory Manual, 2nd ed. (1989), Cold Spring Harbor Laboratory Press).

The invention also refers to molecules of new spider silk proteins. In a particular aspect of the invention, the spider silk proteins comprise the sequences SEQ ID Ns. 20-38.

One particular aspect of the invention provides amino acid sequences of the silk principally related, but not limited to the Major Ampullate gland. Examples of the amino acid sequences related to this gland comprise SEQ ID Ns. 22, 35 and 36.

One particular aspect of the invention provides amino acid sequences principally related, but not limited to the Minor Ampullate gland. Examples of the amino acid sequences related to this gland comprise SEQ ID Ns. 23, 24, 25 and 37.

One particular aspect of the invention provides amino acid sequences principally related, but not limited to the Flagelliform gland. Examples of the amino acid sequences related to this gland comprise SEQ ID Ns. 20 and 34.

One particular aspect of the invention provides amino acid sequences principally related, but not limited to the Tubuliform gland. An example of the amino acid sequence related to this gland comprises SEQ ID N. 21.

One particular aspect of the invention provides amino acid sequences principally related, but not limited to the Aciniform gland. An example of the amino acid sequence related to this gland comprises SEQ ID N. 33.

Another aspect of the present invention provides an isolated molecule of nucleic acid having a sequence selected from the group of SEQ ID Ns.: 1-19 and whereby the expression is controlled by means of specific or constitutive promoters and terminators having a polyadenylation region.

The present invention also describes a method for the production of bio filaments from spider silk proteins produced in prokaryote and eukaryote cells.

Yet another aspect of the invention provides host cells comprising at least one of the spider silk proteins encoded by nucleic acids. These host cells include, but are not limited to, bacterial cells, fungus cells, insect cells, mammal cells and plant cells. Host cells super expressing one or more spider silk proteins encoded by nucleic acids of the present invention provide useful reagents for diverse purposes including, but not limited to, the production of silk fibres comprising at least one silk protein that may be incorporated within a material to modulate the structural properties of that material.

The invention further relates to dermatological compositions characterized by comprising:
a) A recombinant spider silk protein;
b) a pharmaceutically acceptable vehicle.

The invention also describes microbicide compositions characterized by comprising:
a) A recombinant spider silk protein;
b) an agriculturally acceptable vehicle and, optionally,
c) additives.

Another object of the present invention is to provide prokaryote cells and prokaryote organisms containing DNA molecules of the present invention that may be any of the identified sequences from the group SEQ ID N. 1-19, or cells containing gene constructs capable of producing the proteins of the present invention (SEQ ID N. 20-38), or variants of these. The gene constructs may be stably incorporated in the genome of the prokaryote organism cells.

Another object of the present invention is to provide eukaryote cells and eukaryote organisms containing DNA molecules of the present invention that may be any of the identified sequences from the group SEQ ID N. 1-19, or cells containing gene constructs capable of producing the proteins of the present invention (SEQ ID N. 20-38), or variants of these. The gene constructs may be stably incorporated in the genome of the eukaryote organism cells.

In another aspect of the invention, the gene constructs may be provided with a DNA molecule capable of replicating in an autonomous manner in the cells of eukaryote organisms, such as viral vectors. The gene construct may also be arranged in a transitory manner in the cells of eukaryote organisms.

The present invention also describes a method for producing a genetically modified organism characterized by the fact of comprising the following stages:
a) transforming a cell, tissue, organ or embryo with a gene construct in accordance with any of the claims 3 to 11 or an expression vector in accordance with any of the claims 12 to 23;
b) selecting transformed cells, cell calluses, embryos or seeds;
c) regenerating mature plants, mature embryos or microorganisms of the transformed cells, cell calluses, embryos or seeds selected in stage (b);
d) selecting the mature plants, mature embryos or microorganisms cells of stage (c) containing the gene construct or expression vector with the nucleotide sequences that encode the spider silk protein.

The present invention also describes a method for the production of recombinant protein characterized by the fact of comprising the following stages:
a) transforming of a cell, tissue, organ or embryo with an expression vector in accordance with any of the claims 12 to 23;
b) selecting of transformed cells, cell calluses, embryos or seeds;
c) regenerating of mature plants, mature embryos or microorganisms of the transformed cells, cell calluses, embryos or seeds selected in stage (b);
d) selecting of the mature plants, mature embryos or microorganisms cells of stage (c) containing the expression vector with the nucleotide sequences that encode the spider silk protein.
e) extracting of the recombinant spider silk protein produced in the organisms selected in stage (d).

The production of large quantities of spider web proteins in viable prokaryote or eukaryote systems becomes feasible with the possibility of coding spider web proteins with nucleic acid molecules. For example, part or all of at least one DNA molecule coding a natural or synthetic spider web protein, such as a sequence of nucleic acid selected from the group of SEQ ID N. 1-19, may be inserted in a plasmidial vector adapted for the expression of bacteria cells, such as *E. coli*. Such vectors comprise regulatory elements necessary for the expression of the DNA in a host cell positioned in such a manner as to allow the expression of the DNA in that host cell. Such regulatory elements required for expression include promoter sequences, transcription initiation sequences and, optionally, enhancer sequences. Such methods may be used to assess constructs for the expression of spider web proteins, for example, in a bacterial system, thus providing a fast and real triage technique.

The spider web proteins produced through gene expression in a recombinant prokaryote or eukaryote system may be purified following methods known in the state-of-the-art. Preferentially, a commercially viable secretion/expression system may be used, whereby a recombinant protein is expressed and subsequently secreted by the host cell, in order to facilitate purification in a culture medium. If expression/secretion vectors are not used, an alternative technique involves purifying the recombinant protein of the lysed cells derived from the prokaryote or eukaryote cells from which the protein was expressed. Methods to handle such cell lysines are well known in the state-of-the-art. Recombinant proteins may be purified by affinity separation, such as through the immunological interaction with antibodies that specifically bind to the recombinant proteins or nickel columns for isolating the recombinant proteins tagged with 6-8 histidine residues at the N-terminal or C-terminal. Alternative tags consist either of FLAG epitope or hemaglutinin epitope. Such methods are well described in the state-of-the-art and are widely used by experts in the field.

Alternatively, standard purification strategies designed to isolate silk proteins differentially from plant homogenates may also be used to advantage. The purification of spider web proteins expressed in plants may be made easier due to their extreme stability under conditions that normally denature typical proteins such as, for example, high temperatures and low pH values. Protein purification strategies may generally be adapted to optimise the purification of spider web proteins from leaves. Above ground parts of transgenic plants may be picked and dried by normal methods. These dehydrated plant parts may be homogenised in an appropriate buffer followed by several treatments designed to eliminate contaminants differentially. The silk proteins recovered may be optimised following treatments in which the plant extracts are subjected to one or more combinations of the following steps: 1) boiling, either in the presence or absence of detergent; 2) differential centrifugation; 3) progressive decrease of pH, and; 4) precipitation with variable concentrations of urea or ammonium sulphate. These steps may vary in accordance with the intended optimisation of production and the purification efficiency of the spider web proteins in plants.

The spider web protein level may be determined by immunoblotting while the purity and concentration are determined by analysis of the amino acids. Purified spider web protein may be analysed through it's mechanical properties so as to ascertain that the recombinant protein possesses the intended characteristics. The spider web proteins prepared as described above may be analysed in accordance to standard procedures. For example, these proteins may be subjected to analyses of the amino acid sequences in accordance with known methods.

The spider web proteins of the present invention may be used as microbiocides against viral replication; as defensins against insects and pests; as cosmetics or dermatological compositions; in combination with other materials. They may also be introduced in cotton plants to be expressed jointly with cotton fibres in order to increase the resistance and flexibility of the fibre. The proteins of the present invention are also associated to the generation of new variations of the silks naturally produced by spiders and the production of new proteins, peptides and polypeptides having different physical and chemical properties.

EXAMPLES

The present invention is further defined by the following examples. It should be understood that while these examples indicate a part of the invention, they are merely provided in an illustrative form, and do not therefore place any limitation on the scope of the present inventions.

Common molecular biology techniques such as the transformation of bacteria and the electrophoresis of nucleic acids in agarose gel are referred to in the terms by which they are usually described. Details of the practices of these techniques, all well known in the state-of-the-art, are described in Sambrook, et al. (Molecular Cloning, A Laboratory Manual, 2nd ed. 1989, Cold Spring Harbor Laboratory Press). Several solutions, used in the experimental manipulations are referred to by their common names such as "lysing solution", "SSC", "SDS", etc. The composition of these solutions may be found in the above mentioned reference (Sambrook, et al.).

Example 1

Collection and Classification of Spiders and their Webs

Silks of the species of spiders *Argiope* sp., *Ephebopus* sp., *Nephila clavipes*, *Nephilengys cruentata*, *Avicularia juruensis* and *Parawixia bistriata* were collected from the Brazilian biodiversity, mainly from the Amazon region, Atlantic rainforest and corral. The silks were dried at ambient temperature and analysed through infrared microscopy (FTIR).

Significant differences were noted in the results for the alpha- and beta-sheets, mainly associated to the flexibility and resistance of the silks in relation to *Nephila clavipes*. The FTIR has recently been used as a method for determining the secondary structure of proteins in solid state and has proved most viable, especially for insoluble proteins such as those of the spider webs. The secondary structures of the proteins were quantified using the recognition of standards method developed by Forato et al., 1998. The spectrums of the spider webs and products of transgenic expression were obtained from samples prepared in KBr tablets, and was used for quantifying amide band I, between 1600 and 1800 cm-1.

TABLE 01

Percentage of secondary structures found through infra-red analysis of the different species of spiders collected.

| Species | α helix (%) | β-sheet (%) | Coils (%) | Others (%) |
|---|---|---|---|---|
| Argiope | 7 | 56 | 27 | 13 |
| Nephila clavipes | 16 | 43 | 24 | 13 |
| Ephebopus | 2 | 57 | 37 | 13 |
| Nephylengys cruentata | 6 | 53 | 32 | 11 |
| Parawixia bistriata | 17 | 47 | 32 | 12 |
| Avicularia juruensis | 5 | 58 | 32 | 12 |

Example 2

Obtaining Polynucleotide Sequences: Construction of cDNA Libraries, Sequencing

After collection, the silk producing glands of the spiders were isolated in laboratory, immediately frozen in liquid nitrogen and maintained at a temperature of −70° C. Following pulverisation, extraction of the Total RNA was performed using the reagent TRIZOL (Invitrogen), in accordance with the manufacturer's instructions. The Oligotex kit (Qiagen) was used for the purification of the mRNA used for the synthesis of the cDNA, preferentially through the use of the "SUPERSCRIPT II Plasmid System with GATEWAY Technology for cDNA Synthesis and Cloning" Kit (Invitrogen), following the manufacturer's guidelines. After synthesis and fractioning by size in chromatography columns, using Sepharose CL-2B resin (Pharmacia). Both large (1-5 Kb) and small (0.5-2 Kb) cDNA fragments were inserted in appropriate vectors such as pSPORT-1 (Life), pCMV-SPORT 6 or pTrueBlue (Genetix). The libraries thus obtained were introduced into host cells, preferentially by electroporation (25 mF, 200 W, 1.8 KV) in DH5α bacteria (Invitrogen).

The transformed bacteria were cultivated on 7.5 cm Petri plates containing LB (Luria-Bertani) medium with an appropriate selective agent (Sambrook et al., 1989). Those presenting an insert (white) were transferred to 96 well plates. A copy of each 96 well plate was made by means of a replicator and both replicas were maintained at a temperature of −70° C.

The DNA for sequencing was prepared from inoculums from one of the replica plates using the alkaline lysis method (Sambrook et al., 1989) modified for use with 96 well plates. The sequencing reactions were performed using the BigDye Terminator Cycle Sequencing Kit (Applied Biosystems). The primers used in the sequencing reactions were chosen in accordance with the vector in which the library was constructed. All clones were sequenced from the original 5' extremity of the mRNA molecule of the insert, and part of them were also sequenced from the 3' extremity The sequencing reactions were read in Applied Biosystems 3700 automatic sequencers. The resulting electropherograms were transferred to a centralised Data Base, located at the Laboratório de Bioinformática da Embrapa Recursos Genéticos e Biotecnologia [Bioinformatics Laboratory of Embrapa Genetic Resources and Biotechnology], for processing and analysis.

The sequences produced were deposited in the GenBank (Benson et al. 1999) and transferred to the BCCC (http://www.bcccenter.fcav.unesp.br) where they are at the disposal of the international scientific community. These sequences are also described in the Sequences List, SEQ. ID. N. 1 to SEQ. ID. N. 19.

The techniques of genetic engineering described herein are known to experts in the field and are also described in Sambrook et al., 1989 (Sambrook, 3., Fritsch, E. F. and Maniatis, T. 1989. Molecular Cloning: A Laboratory Manual—volumes 1, 2 and 3. Cold Spring Harbor Laboratory, Cold Spring Harbor, N.Y.), Silhavy et al., 1984 (Silhavy, T. J.; M. L. Bennan & L. W. Enquist. 1984. Experiments with Gene Fusions, Cold Spring Harbor Laboratory, Cold Spring Harbor, N.Y.) and Ausubel, et al., 1987. (Current Protocols in Molecular Biology, pub. by Greene Publishing Assoc. and Wiley-Interscience).

Example 3

Mechanical Analysis of the Silks from the Different Spiders Species

Collection of Silk—

Five samples of each species with lengths of approximately 5 cm were positioned on a mechanical trial card, as formerly described by Stauffer et al. (Stauffer S L, Coguil S L, Lewis R V. Comparison of physical properties of three silks from *Nephila clavipes* and *Araneus gemmoides*. The journal of Arachnology. 1994; 22:5-11).

Measurement of Fibre Diameters—

The fibres were analysed using a Nikon Eclipse E200 microscope equipped with a camera. Each silk was observed magnified 800 times and the images were visualised with the SPOT Basic software. The diameters were determined using the ImageJ software, version 1.32 (http://rsb.info.nih.gov/ij/), and the final value was obtained from the average of 5 measurements taken along the length of the fibres.

Mechanical Test—

Each fibre was tested with a Synergie 100 Mechanical Testing System (MTS), using a custom 10-g load cell. The fibres were stretched at a rate of 2 mm/min and the data was collected at a frequency of 35 Hz. Data collection was done using the Testworks 4 software (MTS Systems Corporation, Cary, N.C.). Stress x strain graphs were constructed using Microsoft Office Excel 2003 software.

The equations below were used to calculate the stress, strain and stiffness values.

$$\sigma \text{ (stress)} = F/A,$$

where F is the force applied and A the transversal section area.

$$\varepsilon \text{ (strain)} = \Delta L/L0,$$

where $\Delta L$ is the change in length of the fibre and L0 is the initial length.

$$Y(\text{stiffness or Young's modulus}) = \sigma/\varepsilon$$

| SPECIES | DIAMETER (μm) | STRAIN (%) | STRESS (GPa) | STIFFNESS (GPa) |
|---|---|---|---|---|
| *Avicularia juruensis* | 9.62 ± 3.92 | 7.54 ± 5.71 | 0.07 ± 0.03 | 0.017 ± 0.018 |
| *Nephilengys cruentata* | 4.82 ± 0.61 | 11.88 ± 2.97 | 0.81 ± 0.23 | 0.253 ± 0.306 |
| *Parawixia bistriata* | 7.56 ± 1.21 | 21.54 ± 5.01 | 0.76 ± 0.14 | 0.069 ± 0.024 |
| *Nephila clavipes* * | ? | 22.89 ± 3.58 | 9.53 ± 0.06 | 0.062 ± 0.019 |
| *Araneus diadematus* * | ? | 28.00 ± 4.00 | 1.08 ± 0.16 | 6.90 ± 1.22 |
| *Argiope aurantia* *** | ? | 24.14 ± 4.73 | 1.36 ± 0.58 | 0.202 ± 0.205 |
| *Lactrodectus geometricus* ** | 2.78 ± 0.24 | 14.00 ± 6.00 | 0.83 ± 0.19 | 12.91 ± 7.38 |

*Brooks AE, Steinkraus HB, Nelson SR, Lewis RV. An investigation of the divergence of major ampullate silk fibers from *Nephila clavipes* and *Argiope aurantia*. Biomacromolecules. 2005 Nov-Dec; 6(6): 3095-9.
**Motriuk-Smith D, Lewis RV. Brown Widow (*Latrodectus geometricus*) major ampullate silk protein and its material properties. *Biomed Sci Instrum*. 2004; 40: 64-9.
***Madsen B, Shao ZZ, Vollrath F. Variability in the mechanical properties of spider silks on three levels: interspecific, intraspecific and intraindividual. *Int J Biol Macromol*. 1999 Mar-Apr; 24(2-3): 301-6.

Example 4

Comparative of the Sequences of the Present Invention with the Existing Sequences in the State-of-the-Art In relation to SEQ ID N. 1 (Product of Gene: *Nephilengys cruentata*—NCFlag) a search in GenBank using the BLASTP software revealed the following 10 protein sequences as being the most similar described:
1. gi|7106228|gb|AAF36091.1
2. gi|7106224|gb|AAF36090.1
3. gi|2833649|gb|AAC38847.1
4. gi|13561982|gb|AAK30594.1
5. gi|2833647|gb|AAC38846.1
6. gi|70913024|gb|AAZ15322.1
7. gi|13562004|gb|AAK30605.1
8. gi|93138993|gb|ABE99838.1
9. gi|7106229|gb|AAF36092.1
10. gi|89276819|gb|ABD66603.1

As may be verified referring to Table 1, sequence number 9 (gi|7106229, highlighted by an asterisk on the table) is the one having the smallest percentage of amino acid discrepancies when aligned with SEQ ID N. 1. Of the total amino acids aligned between these two protein sequences, 23% are divergent. It is important to note that amino acids aligned with gaps are not included in this calculation, and that the alignment contemplated by this analysis is the multiple alignment between all eleven proteins. Observing the message "Error: Reference source not found" it is possible to note that the discrepancy would be even greater if the gaps were included in the calculation. The Table also confirms that several other previously described sequences (underlined values) present greater similarity levels between themselves rather than that observed between SEQ ID N. 1 and the previously described sequences.

TABLE 1

Percentage of amino acid discrepancies between the pair by pair alignments of 11 sequences relating to SEQ ID N. 1.

| | SI 1 | 1 | 2 | 3 | 4 | 5 | 6 | 7 | 8 | 9 |
|---|---|---|---|---|---|---|---|---|---|---|
| 1 | 44 | | | | | | | | | |
| 2 | 39 | 20 | | | | | | | | |
| 3 | 25 | 46 | 40 | | | | | | | |
| 4 | 42 | 47 | 43 | 43 | | | | | | |
| 5 | 42 | 10 | 27 | 45 | 47 | | | | | |
| 6 | 52 | 54 | 52 | 50 | 53 | 53 | | | | |
| 7 | 52 | 54 | 52 | 50 | 53 | 53 | 0 | | | |
| 8 | 53 | 57 | 55 | 52 | 55 | 55 | 16 | 16 | | |
| 9 | 23* | 40 | 41 | 8 | 43 | 37 | 51 | 51 | 54 | |
| 10 | 59 | 65 | 62 | 60 | 59 | 62 | 58 | 58 | 61 | 60 |

"SI 1" indicates the SEQ ID N. 1.
The numbers that identify lines and columns correspond to the numbers on the list of the sequences previously described in the state-of-the-art.
The number found at the intersection of a line with a column represents the percentage of discrepancy observed in the alignment of the two sequences.
The asterisk denotes the greatest similarity encountered between SEQ ID N. 1 and the previously described sequences.
The underlined values represent similarities between the previously described sequences greater than those found for SEQ ID N. 1.
Only half of the Table is filled out because the values are reciprocal.

FIG. 1 indicates an alignment between SEQ ID N. 1 and sequence number 9 (gi|7106229) which highlights identical amino acids between the two sequences. The numbers over the sequence identify the position in the alignment. The difference is due to the insertion of gaps to maintain the alignment.

In order to calculate the percentage of discrepancies, the sequence of the present invention was used in a comparative search of the GenBank CDS non-redundant protein sequences bank (Benson, D. A., Karsch-Mizrachi, I., Lipman, D. J., Ostell, J., Wheeler, D. L. (2006). GenBank. Nucleic Acids Res. 34 (Database issue): D16-20). The search was conducted without using a low complexity filter, with size 3 words, using a BLOSUM62 matrix, an 11 point penalty for the opening of gaps and 1 point per extended amino acid. The sequences with the 10 highest "scores" were used in a multiple alignment with the ClustalX (Thompson, J. D., Gibson, T. J., Plewniak, F., Jeanmougin, F. and Higgins, D. G. (1997). The ClustalX windows interface: flexible strategies for multiple sequence alignment aided by quality analysis tools. Nucleic Acids Research, 24: 4876-4882). The multiple alignments used a Gonnet 250 matrix penalising a gap opening by 10 points and according 0.20 to each extended amino acid. The pair by pair alignment used the "slow-precise" approach by lowering the gap extension penalty to 0.10 points. The result of the final multiple alignment was used in a pair by pair distance comparative, with the aid of the MEGA3 software (Kumar, S., Tamura, K. and Nei, M. (2004). MEGA3: Integrated software for Molecular Evolutionary Genetics Analysis and sequence alignment. Briefings in Bioinformatics 5: 150-163). The percentage of discrepancies was calculated by dividing the number of different amino acids by the total number of amino acids compared. The gaps in the alignment were retained in the analysis and eliminated pair by pair. The figure of the alignment was generated from an alignment between the two sequences under consideration, using the same parameters as for the single alignment. The alignment result was formatted using the ESPript software (Gouet, P., Courcelle, E., Stuart, D. I. and Metoz, F. (1999). ESPript: multiple sequence alignments in PostScript. Bioinformatics. 15: 305-8. http://espript.ibcp.fr/ESPript/ESPript/).

In relation to SEQ ID N. 2 (Product of Gene: *Nephilengys cruentata*—NCTuSp), the 10 most similar protein sequences already described are:
1. gi|83758427
2. gi|68342501
3. gi|89365776
4. gi|89365774
5. gi|63054329
6. gi|61387244
7. gi|70927654
8. gi|63054327
9. gi|61387237
10. gi|61387234

TABLE 2

Percentage of amino acid discrepancies between the pair by pair alignments of 11 sequences relating to SEQ ID N. 2.

| | SI 1 | 1 | 2 | 3 | 4 | 5 | 6 | 7 | 8 | 9 |
|---|---|---|---|---|---|---|---|---|---|---|
| 1 | 33 | | | | | | | | | |
| 2 | 33 | 7 | | | | | | | | |
| 3 | 36 | 45 | 45 | | | | | | | |
| 4 | 37 | 48 | 45 | 11 | | | | | | |
| 5 | 38 | 48 | 48 | 11 | 13 | | | | | |
| 6 | 37 | 22 | 20 | 47 | 47 | 49 | | | | |
| 7 | 47 | 51 | 51 | 40 | 40 | 41 | 53 | | | |
| 8 | 46 | 51 | 50 | 39 | 39 | 41 | 53 | 1 | | |
| 9 | 27* | 47 | 44 | 23 | 24 | 22 | 47 | 33 | 34 | |
| 10 | 39 | 46 | 45 | 10 | 06 | 14 | 47 | 47 | 47 | 21 |

"SI 2" indicates the SEQ ID N. 2.
The numbers that identify lines and columns correspond to the numbers on the above list.
The number found at the intersection of a line with a column represents the percentage of discrepancy observed in the alignment of the two sequences.
The asterisk denotes the greatest similarity encountered between SEQ ID N. 2 and the previously described sequences.
The underlined values represent similarities between the previously described sequences greater than those found for SEQ ID N. 2.
Only half of the Table is filled out since the values are reciprocal.

In relation to SEQ ID N. 3 (Product of Gene: *Nephilengys cruentata*—NCMaSp), the 10 most similar protein sequences already described are:
1. gi|83758427
2. gi|68342501
3. gi|89365776
4. gi|89365774
5. gi|63054329
6. gi|61387244

7. gi|70927654
8. gi|63054327
9. gi|61387237
10. gi|61387234

TABLE 3

Percentage of amino acid discrepancies between the pair by pair alignments of 11 sequences relating to SEQ ID N. 3.

| SI 3 | 1 | 2 | 3 | 4 | 5 | 6 | 7 | 8 | 9 |
|---|---|---|---|---|---|---|---|---|---|
| 1 | 7* | | | | | | | | |
| 2 | 15 | 7 | | | | | | | |
| 3 | 18 | 9 | 11 | | | | | | |
| 4 | 24 | 9 | 14 | 2 | | | | | |
| 5 | 22 | 10 | 13 | 2 | 4 | | | | |
| 6 | 17 | 10 | 10 | 1 | 1 | 1 | | | |
| 7 | 17 | 9 | 14 | 2 | 2 | 2 | 2 | | |
| 8 | 16 | 7 | 14 | 9 | 9 | 7 | 8 | 9 | |
| 9 | 22 | 10 | 13 | 2 | 3 | 2 | 2 | 2 | 10 |
| 10 | 11 | 8 | 5 | 1 | 1 | 0 | 0 | 1 | 6 | 1 |

"SI 3" indicates the SEQ ID N. 3.
The numbers that identify lines and columns correspond to the numbers on the above list.
The number found at the intersection of a line with a column represents the percentage of discrepancy observed in the alignment of the two sequences.
The asterisk denotes the greatest similarity encountered between SEQ ID N. 3 and the previously described sequences.
The underlined values represent similarities between the previously described sequences greater than those found for SEQ ID N. 3.
Only half of the Table is filled out since the values are reciprocal.

In relation to SEQ ID N. 4 (Product of Gene: *Nephilengys cruentata*—NCMaSp), the 10 most similar protein sequences already described are:
1. gi|2605800|
2. gi|85680899
3. gi|2605798|
4. gi|50363143
5. gi|50363141
6. gi|50363145
7. gi|2911274|
8. gi|50363137
9. gi|13561992
10. gi|50363139

TABLE 4

Percentage of amino acid discrepancies between the pair by pair alignments of 11 sequences relating to SEQ ID N. 4.

| SI 4 | 1 | 2 | 3 | 4 | 5 | 6 | 7 | 8 | 9 |
|---|---|---|---|---|---|---|---|---|---|
| 1 | 25* | | | | | | | | |
| 2 | 41 | 34 | | | | | | | |
| 3 | 50 | 34 | 8 | | | | | | |
| 4 | 45 | 50 | 54 | 54 | | | | | |
| 5 | 50 | 51 | 59 | 58 | 2 | | | | |
| 6 | 50 | 52 | 55 | 55 | 19 | 21 | | | |
| 7 | 51 | 53 | 59 | 57 | 4 | 7 | 19 | | |
| 8 | 47 | 52 | 57 | 55 | 1 | 1 | 18 | 4 | |
| 9 | 50 | 52 | 58 | 58 | 29 | 34 | 37 | 38 | 30 |
| 10 | 49 | 54 | 51 | 50 | 2 | 2 | 17 | 2 | 2 | 33 |

"SI 4" indicates the SEQ ID N. 4.
The numbers that identify lines and columns correspond to the numbers on the above list.
The number found at the intersection of a line with a column represents the percentage of discrepancy observed in the alignment of the two sequences.
The asterisk denotes the greatest similarity encountered between SEQ ID N. 4 and the previously described sequences.
The underlined values represent similarities between the previously described sequences greater than those found for SEQ ID N. 4.
Only half of the Table is filled out since the values are reciprocal.

In relation to SEQ ID N. 5 (Product of Gene: *Nephilengys cruentata*—NCMISp 06A01), the 10 most similar protein sequences already described are:
1. gi|2605798
2. gi|8572061
3. gi|765323
4. gi|27228959
5. gi|47007923
6. gi|47007963
7. gi|13561992
8. gi|108707764
9. gi|89276817
10. gi|2914731

TABLE 5

Percentage of amino acid discrepancies between the pair by pair alignments of 11 sequences relating to SEQ ID N. 5.

| SI 5 | 1 | 2 | 3 | 4 | 5 | 6 | 7 | 8 | 9 |
|---|---|---|---|---|---|---|---|---|---|
| 1 | 13* | | | | | | | | |
| 2 | 39 | 52 | | | | | | | |
| 3 | 39 | 47 | 2 | | | | | | |
| 4 | 46 | 47 | 49 | 49 | | | | | |
| 5 | 46 | 56 | 49 | 49 | 57 | | | | |
| 6 | 45 | 53 | 36 | 39 | 54 | 53 | | | |
| 7 | 53 | 58 | 60 | 60 | 58 | 65 | 59 | | |
| 8 | 47 | 51 | 48 | 48 | 56 | 53 | 52 | 59 | |
| 9 | 53 | 57 | 62 | 61 | 56 | 66 | 61 | 37 | 58 |
| 10 | 54 | 53 | 60 | 60 | 54 | 67 | 57 | 36 | 58 | 22 |

"SI 5" indicates the SEQ ID N. 5. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 5 and the previously described sequences.
The underlined values represent similarities between the previously described sequences greater than those found for SEQ ID N. 5.
Only half of the Table is filled out since the values are reciprocal.

In relation to SEQ ID N. 6 (Product of Gene: *Nephilengys cruentata*—NCMiSp 11F12), the 10 most similar protein sequences already described are:
1. gi|85680899
2. gi|2605798|
3. gi|89113992
4. gi|13562018
5. gi|63054333
6. gi|63054353
7. gi|63054329
8. gi|61387237
9. gi|13561994
10. gi|89365776

TABLE 6

Percentage of amino acid discrepancies between the pair by pair alignments of 11 sequences relating to SEQ ID N. 6.

| SI 6 | 1 | 2 | 3 | 4 | 5 | 6 | 7 | 8 | 9 |
|---|---|---|---|---|---|---|---|---|---|
| 1 | 67 | | | | | | | | |
| 2 | 64* | 8 | | | | | | | |
| 3 | 74 | 50 | 54 | | | | | | |
| 4 | 89 | 83 | 84 | 87 | | | | | |
| 5 | 82 | 77 | 77 | 78 | 78 | | | | |
| 6 | 87 | 76 | 80 | 76 | 79 | 60 | | | |
| 7 | 83 | 78 | 81 | 80 | 77 | 54 | 43 | | |
| 8 | 85 | 77 | 81 | 80 | 75 | 53 | 47 | 22 | |
| 9 | 77 | 74 | 76 | 81 | 75 | 63 | 74 | 69 | 69 |
| 10 | 83 | 79 | 81 | 80 | 80 | 54 | 42 | 11 | 22 | 69 |

"SI 6" indicates the SEQ ID N. 6. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 6 and the previously described sequences.
The underlined values represent similarities between the previously described sequences greater than those found for SEQ ID N. 6.
Only half of the Table is filled out since the values are reciprocal.

In relation to SEQ ID N. 7 (Product of Gene: *Nephilengys cruentata*—NCfibroin), the 10 most similar protein sequences already described are:
1. gi|63054331
2. gi|6984160|
3. gi|70905642

4. gi|89365776
5. gi|70905641
6. gi|63054329
7. gi|70905643
8. gi|14973269
9. gi|13562018
10. gi|8885520|

TABLE 7

Percentage of amino acid discrepancies between the pair by pair alignments of 11 sequences relating to SEQ ID N. 7.

| SI 7 | 1 | 2 | 3 | 4 | 5 | 6 | 7 | 8 | 9 |
|---|---|---|---|---|---|---|---|---|---|
| 1 | 80 | | | | | | | | |
| 2 | 77 | 72 | | | | | | | |
| 3 | 78 | 73 | 68 | | | | | | |
| 4 | 81 | 58 | 77 | 75 | | | | | |
| 5 | 78 | 73 | 68 | 3 | 75 | | | | |
| 6 | 81 | 61 | 73 | 74 | 11 | 74 | | | |
| 7 | 78 | 72 | 72 | 25 | 78 | 25 | 74 | | |
| 8 | 76* | 70 | 45 | 61 | 72 | 61 | 72 | 68 | |
| 9 | 84 | 77 | 78 | 72 | 79 | 72 | 79 | 74 | 72 |
| 10 | 79 | 72 | 51 | 65 | 75 | 65 | 74 | 66 | 33 | 76 |

"SI 7" indicates the SEQ ID N. 7. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 7 and the previously described sequences.
The underlined values represent similarities between the previously described sequences greater than those found for SEQ ID N. 7.
Only half of the Table is filled out since the values are reciprocal.

In relation to SEQ ID N.8 (Product of Gene: *Nephilengys cruentata*—NCdefensin), the 10 most similar protein sequences already described are:
1. gi|89512121
2. gi|41019463
3. gi|41019465
4. gi|77158011
5. gi|90192368
6. gi|33348850
7. gi|62275780
8. gi|57792507
9. gi|49458046
10. gi|49458052

TABLE 8

Percentage of amino acid discrepancies between the pair by pair alignments of 11 sequences relating to SEQ ID N. 8.

| SI 8 | 1 | 2 | 3 | 4 | 5 | 6 | 7 | 8 | 9 |
|---|---|---|---|---|---|---|---|---|---|
| 1 | 63* | | | | | | | | |
| 2 | 66 | 62 | | | | | | | |
| 3 | 67 | 63 | 11 | | | | | | |
| 4 | 67 | 62 | 1 | 11 | | | | | |
| 5 | 63 | 62 | 49 | 51 | 50 | | | | |
| 6 | 65 | 61 | 2 | 12 | 2 | 50 | | | |
| 7 | 64 | 60 | 0 | 10 | 0 | 48 | 0 | | |
| 8 | 67 | 63 | 17 | 15 | 17 | 51 | 18 | 15 | |
| 9 | 66 | 61 | 18 | 18 | 18 | 51 | 18 | 18 | 13 |
| 10 | 65 | 61 | 15 | 13 | 15 | 50 | 15 | 15 | 1 | 11 |

"SI 8" indicates the SEQ ID N. 8. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 8 and the previously described sequences.
The underlined values represent similarities between the previously described sequences greater than those found for SEQ ID N. 8.
Only half of the Table is filled out since the values are reciprocal.

In relation to SEQ ID N. 9 (*Avicularia juruensis* AJFibroin 1A), the 10 most similar protein sequences already described are:
1. gi|17536963
2. gi|50548483
3. gi|6580883
4. gi|52428273
5. gi|52209673
6. gi|71416355
7. gi|89276819
8. gi|13562018
9. gi|71654760
10. gi|109511662

TABLE 9

Percentage of amino acid discrepancies between the pair by pair alignments of 11 sequences relating to SEQ ID N. 9.

| SI 9 | 1 | 2 | 3 | 4 | 5 | 6 | 7 | 8 | 9 |
|---|---|---|---|---|---|---|---|---|---|
| 1 | 84 | | | | | | | | |
| 2 | 86 | 87 | | | | | | | |
| 3 | 82 | 83 | 86 | | | | | | |
| 4 | 82 | 83 | 86 | 1 | | | | | |
| 5 | 82 | 83 | 86 | 1 | 1 | | | | |
| 6 | 80 | 84 | 87 | 77 | 77 | 77 | | | |
| 7 | 76* | 81 | 83 | 87 | 87 | 87 | 80 | | |
| 8 | 76* | 85 | 87 | 86 | 86 | 86 | 84 | 84 | |
| 9 | 79 | 84 | 88 | 76 | 76 | 76 | 6 | 79 | 83 |
| 10 | 82 | 86 | 83 | 81 | 81 | 81 | 79 | 84 | 88 | 78 |

"SI 9" indicates the SEQ ID N. 9. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 9 and the previously described sequences.
The underlined values represent similarities between the previously described sequences greater than those found for SEQ ID N. 9.
Only half of the Table is filled out since the values are reciprocal.

In relation to SEQ ID N. 10 (*Avicularia juruensis* AFibroin 1B), the 10 most similar protein sequences already described are:
1. gi|68171564
2. gi|17536963
3. gi|89276819
4. gi|38197745
5. gi|13562020
6. gi|38197743
7. gi|83758429
8. gi|71416355
9. gi|70913022
10. gi|1263289

TABLE 10

Percentage of amino acid discrepancies between the pair by pair alignments of 11 sequences relating to SEQ ID N. 10.

| SI 10 | 1 | 2 | 3 | 4 | 5 | 6 | 7 | 8 | 9 |
|---|---|---|---|---|---|---|---|---|---|
| 1 | 88 | | | | | | | | |
| 2 | 83 | 91 | | | | | | | |
| 3 | 75 | 91 | 81 | | | | | | |
| 4 | 75 | 86 | 85 | 45 | | | | | |
| 5 | 76 | 90 | 84 | 76 | 70 | | | | |
| 6 | 74 | 88 | 85 | 44 | 0 | 68 | | | |
| 7 | 77 | 88 | 84 | 85 | 87 | 84 | 85 | | |
| 8 | 82 | 89 | 84 | 78 | 81 | 85 | 80 | 84 | |
| 9 | 76 | 88 | 83 | 41 | 50 | 72 | 50 | 82 | 78 |
| 10 | 73* | 88 | 83 | 30 | 45 | 70 | 45 | 85 | 78 | 49 |

"SI 10" indicates the SEQ ID N. 10. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 10 and the previously described sequences.
The underlined values represent similarities between the previously described sequences greater than those found for SEQ ID N. 10.
Only half of the Table is filled out since the values are reciprocal.

In relation to SEQ ID N. 11 (Product of Gene: *Avicularia juruensis* AJFibroin 2), the 10 most similar protein sequences already described are:

1. gi|1405387
2. gi|38197749
3. gi|38197751
4. gi|38197745
5. gi|50309199
6. gi|38197755
7. gi|38197759
8. gi|38197747
9. gi|50423563
10. gi|38197757

TABLE 11

Percentage of amino acid discrepancies between the pair by pair alignments of 11 sequences relating to SEQ ID N. 11.

| SI 11 | 1 | 2 | 3 | 4 | 5 | 6 | 7 | 8 | 9 |
|---|---|---|---|---|---|---|---|---|---|
| 1 | 66 | | | | | | | | |
| 2 | 41 | 76 | | | | | | | |
| 3 | 42 | 76 | 1 | | | | | | |
| 4 | 55 | 77 | 1 | 0 | | | | | |
| 5 | 68 | 83 | 83 | 83 | 86 | | | | |
| 6 | 33 | 75 | 8 | 10 | 10 | 81 | | | |
| 7 | 42 | 76 | 2 | 2 | 2 | 81 | 9 | | |
| 8 | 42 | 76 | 1 | 1 | 1 | 83 | 9 | 2 | |
| 9 | 76 | 86 | 87 | 88 | 89 | 68 | 86 | 86 | 87 |
| 10 | 32* | 77 | 17 | 17 | 17 | 82 | 8 | 17 | 18 | 84 |

"SI 11" indicates the SEQ ID N. 11. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 11 and the previously described sequences.
The underlined values represent similarities between the previously described sequences greater than those found for SEQ ID N. 11.
Only half of the Table is filled out since the values are reciprocal.

In relation to SEQ ID N. 12 (Product of Gene: *Avicularia juruensis* AJNegProtein 1), the 10 most similar protein sequences already described are:

1. gi|87133239
2. gi|87133241
3. gi|17539308
4. gi|72011370
5. gi|70913024
6. gi|68365042
7. gi|49871101
8. gi|110756487
9. gi|85111705
10. gi|39973263

TABLE 12

Percentage of amino acid discrepancies between the pair by pair alignments of 11 sequences relating to SEQ ID N. 12.

| SI 12 | 1 | 2 | 3 | 4 | 5 | 6 | 7 | 8 | 9 |
|---|---|---|---|---|---|---|---|---|---|
| 1 | 73* | | | | | | | | |
| 2 | 80 | 32 | | | | | | | |
| 3 | 89 | 90 | 93 | | | | | | |
| 4 | 91 | 92 | 89 | 93 | | | | | |
| 5 | 86 | 40 | 43 | 93 | 91 | | | | |
| 6 | 87 | 92 | 91 | 89 | 94 | 90 | | | |
| 7 | 84 | 79 | 77 | 91 | 92 | 83 | 88 | | |
| 8 | 90 | 93 | 93 | 92 | 91 | 93 | 91 | 92 | |
| 9 | 93 | 90 | 89 | 93 | 94 | 92 | 93 | 92 | 93 |
| 10 | 90 | 88 | 93 | 92 | 92 | 92 | 91 | 91 | 92 | 93 |

"SI 12" indicates the SEQ ID N. 12. The numbers that identify lines and columns correspond to the numbers on the above list The number found at the intersection of a line with a column represents the percentage of discrepancy observed in the alignment of the two sequences.
The asterisk denotes the greatest similarity encountered between SEQ ID N. 12 and the previously described sequences.
The underlined values represent similarities between the previously described sequences greater than those found for SEQ ID N. 12.
Only half of the Table is filled out since the values are reciprocal.

In relation to SEQ ID N. 13 (Product of Gene: *Avicularia juruensis* AJNegProtein 2), the 10 most similar protein sequences already described are:

1. gi|22074292
2. gi|15021422
3. gi|88713113
4. gi|55593156
5. gi|82539404
6. gi|109467082
7. gi|3236370
8. gi|6677817
9. gi|71992048
10. gi|62175305|

TABLE 13

Percentage of amino acid discrepancies between the pair by pair alignments of 11 sequences relating to SEQ ID N. 13.

| SI 13 | 1 | 2 | 3 | 4 | 5 | 6 | 7 | 8 | 9 |
|---|---|---|---|---|---|---|---|---|---|
| 1 | 72* | | | | | | | | |
| 2 | 72* | 0 | | | | | | | |
| 3 | 74 | 59 | 59 | | | | | | |
| 4 | 85 | 90 | 90 | 87 | | | | | |
| 5 | 90 | 91 | 91 | 91 | 94 | | | | |
| 6 | 83 | 85 | 85 | 83 | 64 | 93 | | | |
| 7 | 83 | 84 | 84 | 83 | 92 | 92 | 90 | | |
| 8 | 84 | 87 | 87 | 82 | 64 | 93 | 24 | 90 | |
| 9 | 75 | 58 | 58 | 56 | 88 | 87 | 84 | 80 | 84 |
| 10 | 80 | 77 | 77 | 80 | 90 | 92 | 90 | 87 | 90 | 72 |

"SI 13" indicates the SEQ ID N. 13. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 13 and the previously described sequences.
The underlined values represent similarities between the previously described sequences greater than those found for SEQ ID N. 13.
Only half of the Table is filled out since the values are reciprocal.

In relation to SEQ ID N. 14 (Product of Gene: *Parawixia bistriata*—PBAciniform), the 10 most similar protein sequences already described are:

1. gi|49871101
2. gi|89114010
3. gi|44980633
4. gi|40787372
5. gi|58864899
6. gi|82936154
7. gi|16741397
8. gi|7243103
9. gi|11596144
10. gi|45439370

TABLE 14

Percentage of amino acid discrepancies between the pair by pair alignments of 11 sequences relating to SEQ ID N. 14.

| SI 14 | 1 | 2 | 3 | 4 | 5 | 6 | 7 | 8 | 9 |
|---|---|---|---|---|---|---|---|---|---|
| 1 | 28* | | | | | | | | |
| 2 | 75 | 74 | | | | | | | |
| 3 | 89 | 90 | 91 | | | | | | |
| 4 | 89 | 89 | 91 | 90 | | | | | |
| 5 | 89 | 91 | 94 | 89 | 93 | | | | |
| 6 | 89 | 91 | 94 | 89 | 93 | 1 | | | |
| 7 | 91 | 93 | 96 | 89 | 93 | 0 | 0 | | |
| 8 | 89 | 91 | 94 | 89 | 93 | 1 | 2 | 1 | |
| 9 | 89 | 91 | 94 | 89 | 92 | 1 | 2 | 1 | 0 |
| 10 | 89 | 91 | 94 | 89 | 92 | 1 | 2 | 1 | 0 | 0 |

"SI 14" indicates the SEQ ID N. 14. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 14 and the previously described sequences.
The underlined values represent similarities between the previously described sequences greater than those found for SEQ ID N. 14.
Only half of the Table is filled out since the values are reciprocal.

In relation to SEQ ID N. 15 (Product of Gene: *Parawixia bistriata* PBFlag), the 10 most similar protein sequences already described are:
1. gi|62465589
2. gi|27228957
3. gi|13561980
4. gi|109500095
5. gi|47606845
6. gi|5921193
7. gi|51975245
8. gi|3236370
9. gi|109487472
10. gi|47219204

TABLE 15

Percentage of amino acid discrepancies between the pair by pair alignments of 11 sequences relating to SEQ ID N. 15.

| SI 15 | 1 | 2 | 3 | 4 | 5 | 6 | 7 | 8 | 9 |
|---|---|---|---|---|---|---|---|---|---|
| 1 | 20* | | | | | | | | |
| 2 | 20* | 0 | | | | | | | |
| 3 | 28 | 19 | 20 | | | | | | |
| 4 | 90 | 87 | 91 | 91 | | | | | |
| 5 | 38 | 35 | 35 | 37 | 91 | | | | |
| 6 | 82 | 90 | 84 | 85 | 92 | 84 | | | |
| 7 | 70 | 79 | 70 | 76 | 91 | 75 | 84 | | |
| 8 | 82 | 90 | 84 | 85 | 92 | 84 | 17 | 82 | |
| 9 | 81 | 90 | 83 | 84 | 92 | 84 | 16 | 83 | 7 |
| 10 | 83 | 90 | 85 | 86 | 91 | 85 | 60 | 84 | 58 | 59 |

"SI 15" indicates the SEQ ID N. 15. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 15 and the previously described sequences.
The underlined values represent similarities between the previously described sequences greater than those found for SEQ ID N. 15.
Only half of the Table is filled out since the values are reciprocal.

In relation to SEQ ID N. 16 (Product of Gene: *Parawixia bistriata*—PBMiSp), the 10 most similar protein sequences already described are:
1. gi|1405387
2. gi|88175701
3. gi|17507879
4. gi|55619549
5. gi|71026577
6. gi|50902080
7. gi|66805291
8. gi|71408138
9. gi|50931795
10. gi|55274106

TABLE 16

Percentage of amino acid discrepancies between the pair by pair alignments of 11 sequences relating to SEQ ID N. 16.

| SI 16 | 1 | 2 | 3 | 4 | 5 | 6 | 7 | 8 | 9 |
|---|---|---|---|---|---|---|---|---|---|
| 1 | 72 | | | | | | | | |
| 2 | 92 | 93 | | | | | | | |
| 3 | 72 | 0 | 93 | | | | | | |
| 4 | 81 | 87 | 92 | 87 | | | | | |
| 5 | 88 | 72 | 93 | 72 | 91 | | | | |
| 6 | 83 | 85 | 92 | 85 | 86 | 92 | | | |
| 7 | 94 | 93 | 92 | 93 | 92 | 90 | 93 | | |
| 8 | 82 | 82 | 93 | 82 | 91 | 89 | 88 | 94 | |
| 9 | 92 | 93 | 91 | 93 | 93 | 94 | 91 | 90 | 92 |
| 10 | 46* | 82 | 94 | 82 | 86 | 91 | 84 | 90 | 86 | 94 |

"SI 16" indicates the SEQ ID N. 16. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 16 and the previously described sequences.
The underlined values represent similarities between the previously described sequences greater than those found for SEQ ID N. 16.
Only half of the Table is filled out since the values are reciprocal.

In relation to SEQ ID N. 17 (Product of Gene: *Parawixia bistriata*—PBMaSp1), the 10 most similar protein sequences already described are:
1. gi|47569234
2. gi|32815671
3. gi|49329892
4. gi|51975246
5. gi|42782789
6. gi|109500095
7. gi|55274104
8. gi|55274084
9. gi|50363145
10. gi|1263285

TABLE 17

Percentage of amino acid discrepancies between the pair by pair alignments of 11 sequences relating to SEQ ID N. 17.

| SI 17 | 1 | 2 | 3 | 4 | 5 | 6 | 7 | 8 | 9 |
|---|---|---|---|---|---|---|---|---|---|
| 1 | 73 | | | | | | | | |
| 2 | 14* | 81 | | | | | | | |
| 3 | 74 | 14 | 81 | | | | | | |
| 4 | 74 | 15 | 80 | 14 | | | | | |
| 5 | 74 | 8 | 81 | 12 | 14 | | | | |
| 6 | 88 | 85 | 79 | 86 | 86 | 85 | | | |
| 7 | 20 | 83 | 20 | 83 | 83 | 84 | 78 | | |
| 8 | 23 | 80 | 19 | 80 | 79 | 81 | 84 | 2 | |
| 9 | 33 | 76 | 21 | 76 | 77 | 76 | 87 | 8 | 9 |
| 10 | 29 | 74 | 14 | 74 | 73 | 74 | 87 | 25 | 25 | 30 |

"SI 17" indicates the SEQ ID N. 17. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 17 and the previously described sequences.
The underlined values represent similarities between the previously described sequences greater than those found for SEQ ID N. 17.
Only half of the Table is filled out since the values are reciprocal.

In relation to SEQ ID N. 18 (Product of Gene: *Parawixia bistriata*—PBMaSp2), the 10 most similar protein sequences already described are:
1. gi|70913022
2. gi|32815671
3. gi|55274104
4. gi|55274080
5. gi|55274092

6. gi|55274136
7. gi|55274128
8. gi|55274086
9. gi|38197745
10. gi|55274082

TABLE 18

Percentage of amino acid discrepancies between the pair by pair alignments of 11 sequences relating to SEQ ID N. 18.

| SI 18 | 1 | 2 | 3 | 4 | 5 | 6 | 7 | 8 | 9 |
|---|---|---|---|---|---|---|---|---|---|
| 1 | 55 | | | | | | | | |
| 2 | 17* | 45 | | | | | | | |
| 3 | 22 | 42 | 23 | | | | | | |
| 4 | 31 | 46 | 21 | 2 | | | | | |
| 5 | 27 | 45 | 26 | 4 | 6 | | | | |
| 6 | 39 | 52 | 23 | 2 | 1 | 6 | | | |
| 7 | 31 | 47 | 21 | 2 | 2 | 6 | 3 | | |
| 8 | 26 | 44 | 21 | 2 | 0 | 2 | 1 | 0 | |
| 9 | 19 | 57 | 25 | 31 | 38 | 35 | 45 | 37 | 33 |
| 10 | 34 | 46 | 23 | 4 | 2 | 8 | 3 | 4 | 2 | 40 |

"SI 18" indicates the SEQ ID N. 18. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 18 and the previously described sequences.
The underlined values represent similarities between the previously described sequences greater than those found for SEQ ID N. 18.
Only half of the Table is filled out since the values are reciprocal.

In relation to SEQ ID N. 19 (Product of Gene: *Parawixia bistriata*—silk gland spidroin), the 10 most similar protein sequences already described are:

1. gi|1399945
2. gi|70913022
3. gi|17507879
4. gi|55274080
5. gi|55274086
6. gi|55274136
7. gi|55274128
8. gi|55274112
9. gi|55274138
10. gi|55274092

TABLE 19

Percentage of amino acid discrepancies between the pair by pair alignments of 11 sequences relating to SEQ ID N. 19.

| SI 19 | 1 | 2 | 3 | 4 | 5 | 6 | 7 | 8 | 9 |
|---|---|---|---|---|---|---|---|---|---|
| 1 | 78 | | | | | | | | |
| 2 | 54 | 79 | | | | | | | |
| 3 | 78 | 0 | 79 | | | | | | |
| 4 | 48 | 79 | 37 | 79 | | | | | |
| 5 | 47* | 77 | 37 | 77 | 0 | | | | |
| 6 | 48 | 77 | 37 | 77 | 1 | 1 | | | |
| 7 | 47* | 80 | 38 | 80 | 2 | 0 | 3 | | |
| 8 | 49 | 78 | 37 | 78 | 1 | 1 | 1 | 1 | |
| 9 | 49 | 78 | 37 | 78 | 2 | 2 | 2 | 2 | 1 |
| 10 | 51 | 80 | 42 | 80 | 8 | 8 | 8 | 8 | 6 | 7 |

"SI 19" indicates the SEQ ID N. 19. The numbers that identify lines and columns correspond to the numbers on the above list. The number found at the intersection of a line with a column represents the percentage of discrepancy observed in the alignment of the two sequences.
The asterisk denotes the greatest similarity encountered between SEQ ID N. 19 and the previously described sequences.
The underlined values represent similarities between the previously described sequences greater than those found for SEQ ID N. 19.
Only half of the Table is filled out since the values are reciprocal.

Example 5

Construction of Expression Vectors Containing Genes of Spider Silk Proteins in Plants The expression vectors used in the present invention contain at least one promoter sequence and one coding sequence for a spider silk protein selected from the group SEQ ID N. 1-19 and one polyadenilation sequence. The expression vector may further contain regulatory sequences responsible for the post-transcriptional processing and compartmentalisation of the heterologous proteins.

Figure 2:
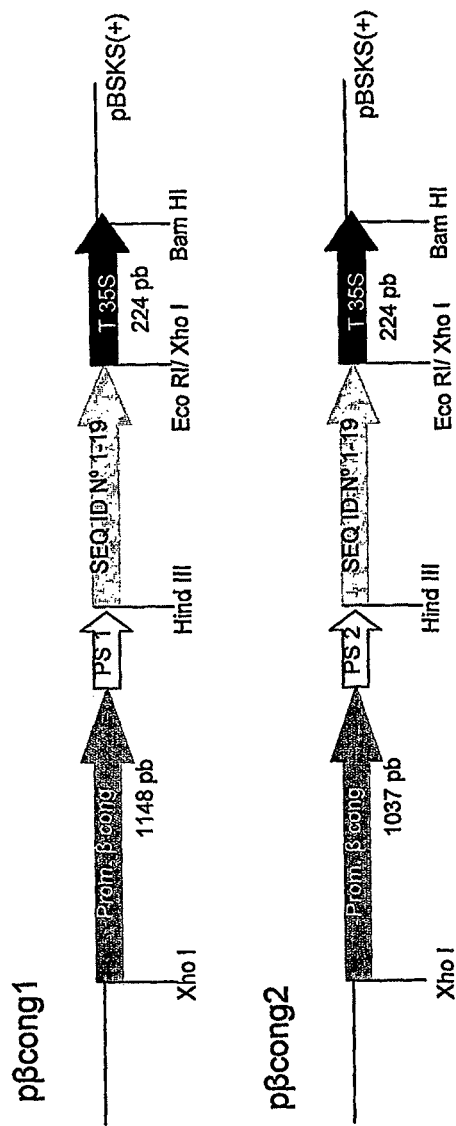
FIG. 2—Vectors containing signal peptide and beta-conglycinin promoter used for bombardment in transformation and co-transformation systems for soybean and cotton plants.

Expression vectors were constructed using standardised recombinant DNA manipulation methodologies (Sambrook, 3. Molecular Cloning: A Laboratory Manual (3-Volume Set) Cold Spring Harbor Laboratory Press; 3rd edition, 2001). Basically, the coding region relating to the fragments: in the case of soy bean, the coding sequences of the silk proteins were cloned under the control of the beta-conglycinin peptide signal and promoter (previously cloned in the Laboratório de Transferência de Genes [Gene Transfer Laboratory]—EMBRAPA) (FIG. 2). The intended alterations aimed adapting the fragment for the addition of the coding sequence of the plant peptide signal, thus allowing it to properly process the recombinant proteins. In the case of cotton, the coding sequences of the silk proteins were cloned under the control of the actin2 peptide signal and promoter of *Arabidopsis* (Aragão F. J. L., Vianna G. R., Carvalheira S. B. R., Rech E. L. (2005) Germ line genetic transformation in cotton (*Gossypium hirsutum* L.) by selection of transgenic meristematic cells with an herbicide molecule. *Plant Sci.* 168: 227-1233).

The gene and protein sequences of the present invention may be modified according to their intended use and still remain within the scope of the invention. For example, when it is intended that the fibre should have low elasticity, the sequence of alanine (Ala) repetitions should be removed and, to the contrary, when a high rate of elasticity is sought, the size of the poly-Ala portion may be increased. Furthermore, the constructs may possibly only include the repetitive modules of the sequences presented herein and, also, a combination of the different protein modules in order to achieve the intended characteristic.

Example 6

Figure 3:
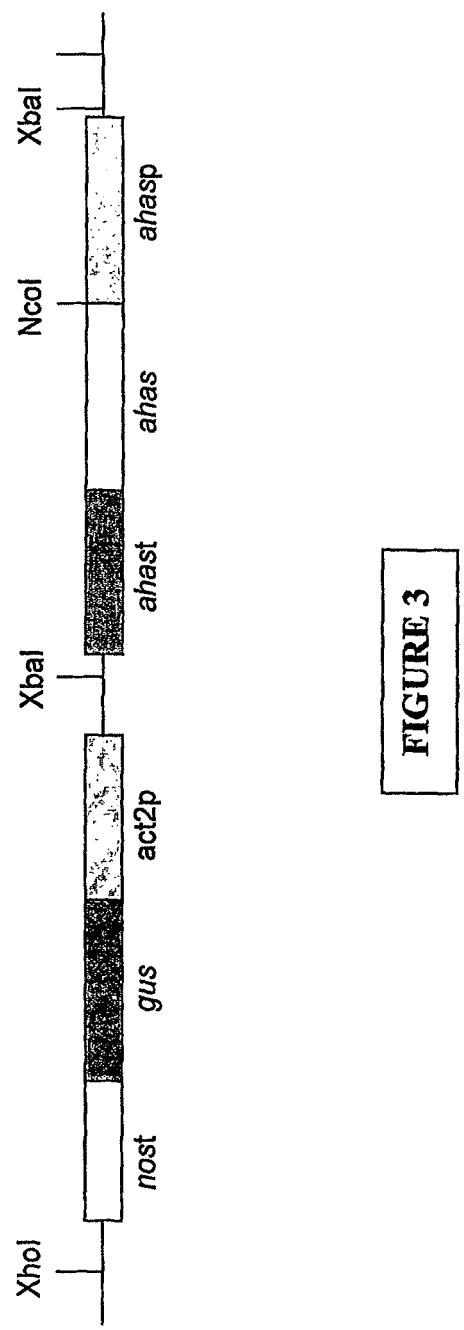
FIG. 3—Vector pAG1 used for bombardment in transformation and co-transformation systems for soybean and cotton plants.

Production of Soybean and Cotton Plants Containing Gene Sequences of Spider Silk Proteins The expression vectors obtained were used in transformation and co-transformation experiments with vector pAG1 (FIG. 3) containing the coding sequence of the ahas gene under control of the ahas gene promoter and NOS terminator. This vector allows the selection of transgenic soybean and cotton plants in vitro. When necessary, the GUS marker gene under control of the 35SCaMV promoter and nos terminator were cloned in pAG1. Transgenic soybean and cotton plants were developed through the bioballistic system developed by EMBRAPA and protected under patent PI9714887-3.

The transgenic plants produced were analysed by PCR (Dellaporta, S. L., Wood, J. and Hicks, J. B. (1983). A plant DNA minipreparation: version II. *Plant Molecular Biology Reports* 1:19-21; Aragão, F. J. L., Barros, L. M. G., Brasileiro, A. C. M., Ribeiro, S. G., Smith, F. D., Sanford, J. C. Rech E. L. (1996). Inheritance of foreign genes in transgenic bean (*Phaseolus vulgaris* L.) co-transformed via particle bombardment. *Theor Appl Genet* 93:142-150) and Southern blot (Dellaporta, S. L., Wood, J. and Hicks, J. B. (1983). A plant DNA minipreparation: version II. *Plant Molecular Biology Reports* 1:19-21; Sambrook J., Fritsch E. F., Maniatis T. (1989). Molecular cloning: a laboratory manual. Cold Spring Harbor Laboratory Press, Cold Spring Harbor, N.Y.) to detect the transgenes as well as by bio-chemical analyses and bioassays. Histochemical analyses were performed to detect the integration of heterologous genes.

Example 7

Use of Agroinfiltration and Viral Vectors for the Expression of Spider Proteins

The transitory expression of the spider genes was assessed by inoculation in planta of *Agrobacterium tumefaciens* strains containing the spider genes cloned in the binary vector pCambia 1300 (www.cambia.org), or in a viral vector based on Potato virus X (PVX). This viral vector, based on the vector pGR107 (Chapman S, Kavanagh T and Baucombe D (1992) Potato virus X as a vector for gene expression in plants. *Plant J* 2:549-557), presents a duplication of the protein sheath promoter and restriction sites for the cloning of exogenous genes. The sequence corresponding to PVX is cloned in a binary vector, under the control of the CaMV35S promoter, thus allowing inoculation through *Agrobacterium* (agroinoculation). The original vector, pGR107, was modified by the addition of the conversion cassette from the Gateway™ cloning system (Invitrogen), at the site SmaI. The resulting vector, PVXGW, is therefore compatible with the Gateway™ cloning system (Invitrogen), which allows the cloning of genes in a much faster and efficient manner when compared to the usual methods of restriction and linking. *Agrobacterium tumefaciens* strains with either binary or viral vectors containing the spider genes were inoculated on leaves of *Nicotiana benthamiana* and the transient expression was assessed after 4-6 days.

Example 8

Figure 4:
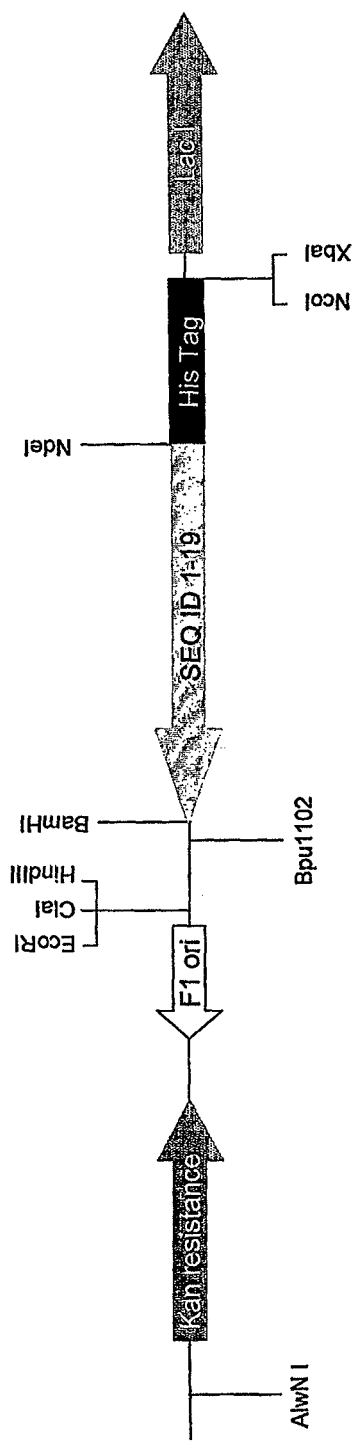
FIG. 4—Vector pET19b: SEQs. 1-19 used in the transformation of *E. coli* for the expression of silk proteins.

Construction of Expression Vectors Containing Genes of Spider Silk Proteins in Bacterial Vectors and Production of these Proteins in the Bacterial Expression System The expression vectors for bacteria used in the present invention were constructed using the pET system (Novagen). Repetitive modules of the spider silk protein coding sequences selected from the group SEQ ID N. 1-19 were synthesised and cloned in vector in vector pUC19 associated to restriction sites that allow multiplication of the repetitive units N times, according to the strategy described by Lewis et al. (Lewis R V, Hinman M, Kothakota S, Fournier M J. Expression and purification of a spider silk protein: A new strategy for producing repetitive proteins. PROTEIN EXPRESSION AND PURIFICATION 7 (4): 400-406 June 1996). The cassettes containing the repetitive modules were transferred to the pET19b vector (Novagen) (FIG. 4) under the control of promoter T7 and fused to a tail of N-terminal histidines. These resulting vectors were used to transform competent *E. coli* cells (strains BL21(DE3) and BL21(DE3) pLysS) by thermal shock. The recombinant bacteria containing the expression vector were inoculated in a culture medium containing the appropriate antibiotic and grown to a $OD_{600nm}$ between 0.8 and 0.9. Protein production was induced with IPTG at a concentration of 1 mM during 3 h at 37° C. under agitation. The culture was then centrifuged at 1500 g for 15 min and resuspended in a lyse buffer, as described by the system's manufacturer. Under these experimental conditions, cells BL21 (DE3) and BL21(DE3)pLysS induced the expression of the genes cited in this heterologous system, and the lysed extract was used to perform the purification by column chromatography using Ni-NTA His-Bind Resin (Qiagen) charged with 50 mM of NiSO4 and 5 mM of imidazole. The fraction containing the recombinant protein was eluted using an elution buffer containing 100 mM of imidazole, dialysed in distilled water over 2 days and then freeze-dried. The recuperation of the purified protein remained at between 0.2 mg/g and 10 mg/g of the dry cell weight.

Example 9

Construction of Expression Vectors Containing the Genes of the Spider Silk Proteins in a Vector of Mammal Cells and Production of these Proteins in the Mammal Expression System At least one of the sequences was used for cloning in the pCMV-Script® vector (Stratagene). This vector is for expression in mammal cells in culture, CHO (Chinese hamster ovary), using the Citomegalovirus promoter and the SV40 polyadenylation site, which allows large constitutive expression rates. The products are expressed from the purified culture supernatant and rested.

Figure 5:
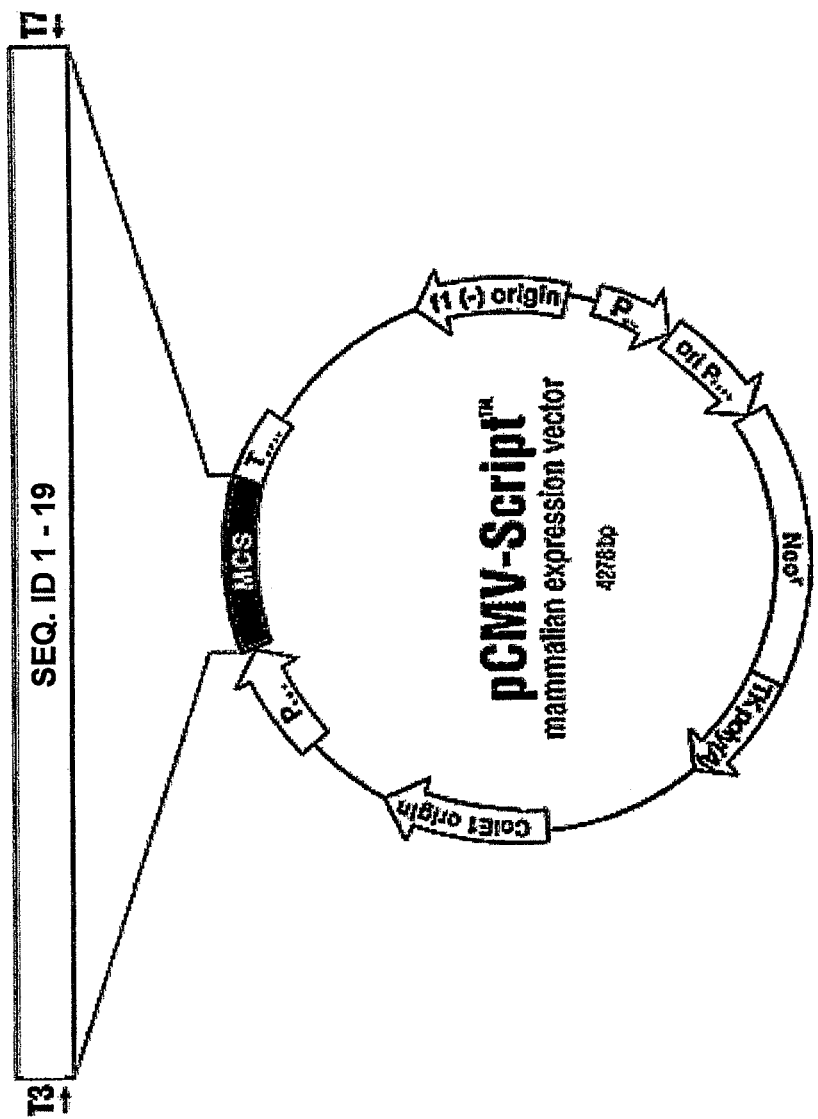
FIG. 5—Vector pCMV-Script containing sequences 1 to 19 for expression in mammal cells. MCS: multiple cloning site; cloning site containing 15 different enzymes with unique sites.

The sequence of the silk protein coding sequences selected from the group SEQ ID N. 1-19, as well as the modularly manipulated versions of these sequences, was inserted in a vector based on the early Cytomegalovirus promoter. The resulting vectors (FIG. 5) were used in the co-transfection of hamster ovary cells (CHO—Chinese hamster ovary) with the use of lipofectin and calcium phosphate, together with the reporter vectors pCMV-Gal (Promega) and pGFP/NEO (Promega). The integrity of the silk proteins under reducer or non-reducer conditions was assessed by Western Blotting. This technique is intended to detect proteins after separation by electrophoresis in polyacrylamide gel and transfer to nitrocellulose or nylon membranes. Detection is through antibodies that specifically react with the epitopes of the intended protein, followed by colorimetric or radiographic reactions.

The production of transgenic mice containing expression vectors having the spider web protein gene sequences was performed using the technique of pronuclear micro-injection. This technique is used for generating transgenic animals by addition. The technique further allows the introduction of long DNA sequences from different species in the genome of mammals conferring high expression levels and integration of the transgene in the germinative cells. Using a micromanipulator coupled to a high-resolution microscope, copies of the expression vectors containing the spider web protein gene sequences selected from the group SEQ ID N. 1-19 were directly injected in a freshly fertilised embryo pronucleus collected from the oviduct of superovulated female donors. The pronucleus is the maternal and paternal nuclei originating in the ovule and the spermatozoid, respectively, before they unite to become a single nucleus containing the genome of the new individual. Following the micro-injection, the embryo were transferred to the oviduct of a pseudo pregnant receptive female earlier mated with a vasectomised male that will bring to term the litter of possible transgenics later genotyped for the presence of the exogenous gene. Integration of the transgene by pronuclear micro-injection occurs in a random way in the genome and all the animal's cells are genetically modified, including the germinative ones which thus transmit the alteration to its descendants. The entire positive transgenic animal originating from a micro-injected embryo was classified as the founder of a single transgenic line that differs from another founder as to the insertion location and number of copies of the transgene in the genome. The detailed protocol for the manipulation of animals for addition of a gene is well described in the state-of-the-art and may be found in manuals and revisions in the literature (Hogan, B., Beddington, R., Costantini, F., Lacy, E. (1994). Manipulating the mouse embryo: A Laboratory Manual, Cold Spring Harbor Laboratory Press, Cold Spring Harbor; Godard, A. L. B., Guénet, J. (1999) Genética de Camundongos. Modelos animais de doenças humanas. *Biotecnologia, Ciência & Desenvolvimento* 9:96-100).

Figure 6:
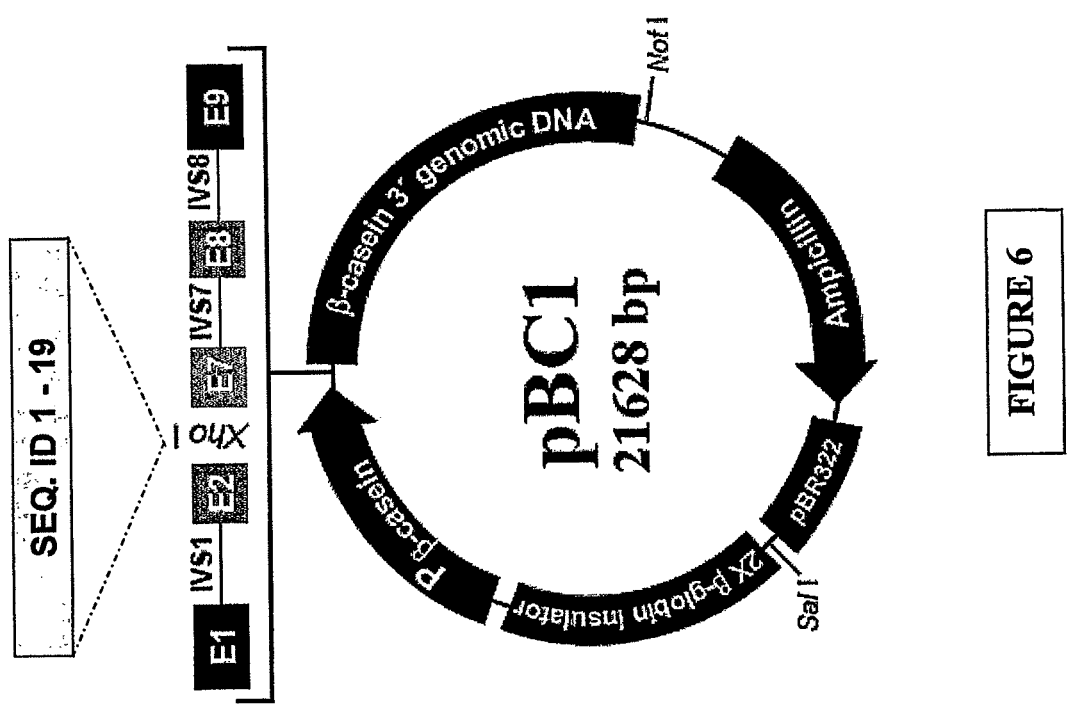
FIG. 6—Vector pBC1 containing sequences 1 to 19 for expression of web proteins in the milk of transgenic animals.

The production of transgenic bovines was used for the actual production of spider silk proteins in milk. The expression vectors used were derived from pBC1 vector (Invitrogen) for the expression of recombinant proteins in the milk of transgenic animals. Genes from the spider web proteins selected from the group SEQ ID N. 1-19 were cloned at site XhoI of these vectors (FIG. 6) with constitutions containing promoters that direct the expression of milk proteins, such as the beta-casein promoter and constitutive (Iguma L. T., Lisauskas S. EC., Melo E. O., Franco M. M., Pivato I., Vianna G. R., Sousa R. V., Dode M. A. N., Aragão F. J. L., Rech E. L., Rumpf R. (2005) Development of bovine embryos reconstructed by nuclear transfer of transfected and non-transfected adult fibroblast cells. *Genet. Mol. Res.* 4: 55-66; Oliveira R. R., Carvalho D. M. de, Lisauskas S., Mello E., Vianna G. R., Dode M. A. N., Rumpf R., Aragão F. J. L., Rech E. L. (2005) Effectiveness of liposomes to transfect livestock fibroblasts. *Genet. Mol. Res.* 4:185-196).

Example 10

Synthesis of the Spider Web Proteins

The spider web proteins of the present invention were synthesised using the technique of automatic synthesis in F-moc solid-phase in a Perseptive Biosystems Pioneer Synthesiser. The proteins were purified in Shimadzu Class VP and Akta Explorer liquid chromatographers using reverse phase columns. Proteins and peptides were analysed by MALDI-TOF mass spectroscopy and sequenced by MS/MS using Voyager DE STR spectrometers, 4700 Proteomics Analyser and Q-TOF, respectively. The liposomes of variable phospholipidic composition were prepared in accordance with the instructions of the commercially available GIBCO BRL (USA) kits.

Example 11

Analysis of the Spider Web Fibres by Electronic Scan Microscopes

A study with electronic scan microscopes was conducted to ascertain the ultrastructural details (thickness, length, external layout, disposal of protein layers, etc.) of the spider web fibres. For such, fibre samples were fixed, dehydrated to critical point, mounted on stub and metallised with different metal alloys, after which they were observed using a Zeiss DSM 962 microscope in accordance with the methodology adapted from Bozzola & Russel (Bozzola, J. J.; Russel, L. D. (1999). Electron microscopy: principles and techniques for biologists. Jones and Bartllet Publishers, Inc. (eds). London, UK. pp. 670-678).

Example 12

Isolation and Characterisation of the Spider Web Proteins by High Powered Liquid Chromatography (HPLC) and by Capillary Liquid Chromatography Coupled to a Mass Spectroscope (CapLC/Q-TOF/MS/MS; TOF-TOF/MS/MS)

The protein extracts of interest were fractioned in a HPLC system and the fractions obtained were enzymatically digested, submitted to capillary liquid chromatography coupled to a mass spectroscope. This process provided the internal sequences of the isolated proteins which were then identified, characterised physically and chemically and used for searches in data bases (Pegah R., Dass J. C. (2004). Proteome analysis in the bovine adrenal medulla using liquid chromatography with tandem mass spectrometry. Rapid Conmmun. Mass Spectrom. 18:1877-1884).

Example 13

Evaluation and Quantification of the Spider Silk Protein Purity

The purity of the proteins was evaluated using HPLC and amino acid composition. The identity of the proteins was confirmed by Western Blot.

The purified material was quantified using the extinction and coefficient method (at 280 nm) and ELISA, with polyclonal antibodies.

Example 14

Preparation and Polymerisation of the Biopolymers

Figure 8:
FIG. 8—Silk produced in vitro

Samples of spider web gland proteins expressed in *E. coli*, purified, dialysed and freeze-dried were prepared for polymerisation and extrusion. Between 60-90 mg of protein were solubilised in 200 µl of hexafluoroisopropanol (HFIP), isopropanol or ethanol and maintained overnight under constant agitation at ambient temperature. The insoluble material was removed by centrifugation and the supernatant was placed in a syringe adapted to a tube used for HPLC having a diameter of 4-300 µl. After removal of all air from the syringe apparatus, an extrusion was made in a coagulation bath in a container holding isopropanol/methanol or ethanol and other organic solvents, which produced fibres similar to the natural fibres (see example in FIG. 8: silk produced in vitro). This process was adapted from the methodology described by Seidel (Seidel A. (1998) Artificial spinning of spider silk. *Macromolecules* 31:6733-6736).

Example 15

Test of the Biopolymers

A quasi static mechanical test was performed using Instron 55R4201 equipment, at 23° C. and 50% relative humidity. The mechanical properties were determined using Instron series IX software specific for the test of materials. The high load tests used the Hopkinson Tension equipment which was defined as being the most appropriate for the sensitivity analyses of the different materials (Shim V. P. W.

(2001) Dynamic mechanical properties of fabric armor. *Int. J. of Impact Eng.* 25:1-15; Huh H., Kang W. J., Han S. S. (2002). A tension split Hopkinson bar for investigating dynamic behaviour of sheets metals. *Exp. Mechanics* 42:8-17). The filaments were aligned and pre-tensioned to ensure uniformity of distribution during the trials.

Example 16

Recombinant Proteins of the Silk Producing Gland of Spiders Used as Defensins, Antimicrobial Peptides and Microbicides Recombinant proteins of spider silks were used to inhibit the replication of several viruses and other pathogenic microorganisms in plants and animals. This may occur due to various mechanisms such as the linking of negatively charged recombinant proteins of the silk gland to charges of the protein sheath of different viruses, thus inhibiting their replication and acting as microbiocides (Scordi-Bello I. A., Mosoian A., He C., Chen Y., Jarvis, Marla G. A., Keller J., Hogarty K., Waller D. P., Profy A. T., Herold B. C., Klotman M. E. 2005. Candidate Sulfonated and Sulfated Topical Microbicides: Comparison of Anti-Human immunodeficiency Virus activities and Mechanisms of Action. ANTI-MICROBIAL AGENTS AND CHEMOTHERAPY, 49: 3607-3615), defensins (Thevissen K., Francois I. E. J. A., Alberts A. M., Cammue B. P. A. (2005) Fungal sphingolipids as targets for the development of selective antifungical therapeutics. *Current Drugs Targ.* 6:923-928) and antimicrobial peptides or polypeptides (Prates M. V., Sforça M. L., Regis W. C. B., Leite J. R. S. A., Silva L. P., Pertinhez H. A., Araujo A. L. T., Azevedo R. B., Spisni A., Bloch C. Jr. (2004) The NMR-derived Solution Structure of a New Cationic Antimicrobial Peptide from the Skin Secretion of the *Anuran Hyla punctata*. *Biol. Chemistry* 279:13018-13026). Therefore, the proteins of the silk producing glands were expressed and tested for this type of activity, showing positive results for the inhibition of viral, fungal and bacterial growth.

Example 17

Molecular Modelling of the Spider Web Proteins

Prediction of the three-dimensional structures of the spider web glands was done by homology modelling or "comparative protein modelling", which is based on the observation that the homology between amino acid sequences implies structural and functional similarities and that homologous proteins present conserved internal regions (mainly formed by secondary structure α-helix and β-sheet elements).

The modelling of these proteins by homology basically followed four successive steps:

Identification and selection of template proteins with a known three-dimensional structure directly from the PDB (Protein Data Bank). A systematic search was conducted using BLAST[36] for one or more adequate using the protein primary sequence as bait in a data base of primary structures derived from proteins with confirmed tertiary structures deposited in the PDB.

Alignment of the amino acid residue sequences. The objective of the alignment is to align structurally equivalent residues taking into account common structural characteristics, such as secondary structure elements. It thus becomes possible to recognise structurally conserved regions and variable regions.

Model construction. This stage deals with modelling the structurally conserved regions, modelling the loop regions and modelling the lateral chains. This was done using the Blue Star Sting software (Goran Neshich, Ivan Mazoni, Stanley R. M. Oliveira, Michel E. B. Yamagishi, Paula R. Kuser-Falcão, Luiz C. Borro, Douglas U. Morita, Kassyus R. R. Souza, Gustavo V. Almeida, Diego N. Rodrigues, José G. Jardine, Roberto C. Togawa, Adauto L. Mancini, Roberto H. Higa, Sérgio A. B. Cruz, Fábio D. Vieira, Edgard H. dos Santos, Raquel C. de Melo and Marcelo M. Santoro. The Star STING server: A multiplatform environment for protein structure analysis. *Genet. Mol. Res.* 5 (2) 2006).

Model Validation. An adequately modelled protein should have a satisfactory tertiary structure. Its quality depends on the protein selected as a template and the alignment calculated. It is important to verify if any major unexplained conformance differences exist between the secondary structure elements (conserved regions) of the template-structure and the model-structure. This example was validated using the PROCIIECK software (Laskowski, R. A.; MacArthur, M. W.; Moss, D. S.; Thornton, J. M.; *J. Appl. Crystallogr.* 1993, 26, 283).

Figure 7:
FIG. 7—Model of the protein structure obtained for SEQ ID N. 1 (Product of the Gene: *Nephilengys cruentata*—NCFlag). A. represents a horizontal view of the structure and B. represents a view of the upper end from one of the extremities.

These steps were followed for SEQ ID N. 1 (Product of Gene: *Nephilengys cruentata*—NCFlag), and the model obtained may be seen in FIG. 7.

As the silk proteins and modular structures have no known atomic structure as yet, the geometries shall be constructed ab initio (prediction of the three-dimensional structures of the proteins derived from their primary structures), based on the contents of the secondary structures and the hypotheses relating to the doubling of the proteins. Portions such as the N-terminus and C-terminus that do not contain modular sequence blocks shall have their structure determined by x-ray crystallography. The purified proteins shall be crystallised through optimisation of the matrix results. As they possess characteristics of new proteins, the structures shall be determined using either multiple isoform replacements (MIR) after treatment of the atoms or through anomalous dispersion of the crystals containing selenomethionine.

The invention claimed is:

1. A composition useful for modulating structural properties of material comprising: a host cell comprising at least one functionally expressed molecule of a spider nucleic acid operably linked to at least one regulatory element necessary for the expression of the molecule, wherein the spider nucleic acid encodes a protein from *Nephilengys cruentata*, and wherein the sequence of the molecule of spider nucleic acid is SEQ ID No. 1; and wherein the host cell is selected from the group consisting of bacterial cells, fungus cells, insect cells, mammal cells, and plant cells.

2. A chimeric gene comprising the molecule of claim 1.

3. A chimeric gene comprising: a) a promoter optionally linked to a leader sequence and operationally linked to; b) a coding sequence having the sequence of SEQ ID No: 1.

4. An expression vector comprising the chimeric gene in accordance with claim 2.

5. The expression vector of claim 4 wherein the promoter contains enhancer elements.

6. An isolated transformed cell comprising the expression vector of claim 4, wherein the cell is selected from the group consisting of a bacterial cell, a fungus cell, an insect cell, a mammal cell, and a plant cell.

7. A plant or a propagule or progeny thereof, comprising the expression vector of claim 4.

8. A non-human, non-arachnid animal or a progeny thereof, comprising the expression vector of claim 4.

9. A microorganism comprising the expression vector of claim 4.

10. An isolated transformed cell comprising the chimeric gene of claim 2, wherein the cell is selected from the group consisting of a bacterial cell, a fungus cell, an insect cell, a mammal cell, and a plant cell.

11. A plant or a propagule or progeny thereof, comprising the chimeric gene of claim 2.

12. A non-human, non-arachnid animal or a progeny thereof, comprising the chimeric gene of claim 2.

13. A microorganism comprising the chimeric gene of claim 2.

14. A method for producing a genetically modified non-human organism comprising:
a) transforming a non-human cell, tissue, organ, embryo or microorganism with the chimeric gene of claim 2 or the expression vector of claim 4 to create transformed cells, cell calluses, embryos, seeds or microorganisms;
b) selecting transformed cells, cell calluses, embryos, seeds or microorganisms;
c) generating mature plants, mature embryos seeds or microorganisms of from the transformed cells, cell calluses, embryos, of seeds or microorganisms selected in stage (b); and
d) selecting mature plants, mature embryos, seeds or microorganisms cells of stage (c) containing the chimeric gene of claim 2 or the expression vector of claim 4 and which express SEQ ID No: 1.

15. A method for the production of a recombinant protein encoded by SEQ ID No: 1 comprising:
a) transforming a non-human cell, tissue, organ, embryo or microorganism with the expression vector of claim 4;
b) selecting transformed cells, cell calluses, embryos, seeds or microorganisms;
c) generating mature plants, mature embryos seeds or microorganisms of the transformed cells, cell calluses, embryos or seeds selected in (b);
d) selecting mature plants, mature embryos seeds or microorganisms cells of stage-(c) that express SEQ ID No: 1 and
e) extracting the recombinant protein encoded by SEQ ID No: 1 produced in the mature plants, mature embryos, seeds or microorganisms selected in (d).

16. The chimeric gene of claim 3 wherein the promoter contains enhancer elements.

17. The chimeric gene of claim 3 wherein said promoter is selected from the group consisting of constitutives, inducibles and tissue-specific promoters.

18. The chimeric gene of claim 17 wherein the tissue-specific promoter is selected from cotton fiber gene promoters.

19. The chimeric gene in accrdense with of claim 18 wherein said cotton fibre gene promoters are selected from the group consisting of E6, H6S, Rac13, LTP, ACP, expansin, CAP, anexin, FbL2A and actin 2 promoters.

20. The chimeric gene of claim 3 wherein said promoter may be expressed in plants, animals, fungus or insects.

21. The chimeric gene of claim 3 wherein the leader sequence is obtained from the same gene as the promoter.

22. An expression vector comprising: a) a promoter optionally linked to a leader sequence and operationally linked to; b) a coding sequence having the sequence of SEQ ID No: 1 operationally linked to; c) a termination signal; d) an origin of replication; e) a selective marker; and f) a cloning site.

23. The expression vector of claim 22 wherein the promoter is selected from the group consisting of constitutives, inducibles and tissue-specific promoters.

24. The expression vector of claim 23 wherein the tissue-specific promoter is selected from cotton fibre gene promoters.

25. The expression vector of claim 24 wherein the cotton fibre gene promoters are selected from the group consisting of E6, H6S, Rac13, LTP, ACP, expansin, CAP, anexin, FbL2A and actin 2 promoters.

26. The expression vector of claim 22 wherein said leader sequence is obtained from the same gene as the.

27. The expression vector of claim 22 wherein the promoter directs expression of SEQ ID No: 1 in plants, animals, fungus or insects.

28. The expression vector of claim 22 wherein the transcription termination signal is selected from the group consisting of SV40 termination signal, *Agrobacterium tumefaciens* nopaline synthetase (NOS) termination signal, octopine synthetase termination signal, cauliflower mosaic virus (CaMV) 19S termination signal, CaMV 35S termination signal, maize alcohol dehydrogenase termination signal, manopine synthetase termination signal, beta-phaseolin termination signal, ssRUBISCO termination signal, sucrose synthetase termination signal, and *Aspergillus nidulans* trpC termination signal.

29. The expression vector of claim 22 wherein the selective marker is selected from the group consisting of sequences that confer resistance to antibiotics and visual markers.

30. The expression vector of claim 29 wherein said selective marker is selected from the group of sequences conferring resistance to kanamycin, neomycin, ampicillin, chloramphenicol, streptomycin, hygromycin, geneticin, phosphinotrycin, glyphosate, ammonium gluphosinate, AHAS, BAR and β-glucuronidase (GUS).

31. The expression vector of claim 22, further comprising a polyadenylation region.

32. The expression vector of claim 31, wherein the polyadenylation region is a herpes simplex virus TK (HSV-TK) polyadenylation signal.

* * * * *